(12) United States Patent
Clarke et al.

(10) Patent No.: US 9,751,915 B2
(45) Date of Patent: Sep. 5, 2017

(54) MUTANT PORES

(75) Inventors: James Clarke, Oxford (GB); Andrew John Heron, Oxford (GB); Lakmal Jayasinghe, Oxford (GB); Elizabeth Jayne Wallace, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 449 days.

(21) Appl. No.: 13/984,628

(22) PCT Filed: Feb. 10, 2012

(86) PCT No.: PCT/GB2012/050301
§ 371 (c)(1),
(2), (4) Date: Feb. 27, 2014

(87) PCT Pub. No.: WO2012/107778
PCT Pub. Date: Aug. 16, 2012

(65) Prior Publication Data
US 2014/0186823 A1   Jul. 3, 2014

Related U.S. Application Data

(60) Provisional application No. 61/441,718, filed on Feb. 11, 2011.

(51) Int. Cl.
| | |
|---|---|
| A61K 39/04 | (2006.01) |
| A61K 39/02 | (2006.01) |
| A61K 39/00 | (2006.01) |
| C07K 14/35 | (2006.01) |
| C12Q 1/68 | (2006.01) |

(52) U.S. Cl.
CPC .............. *C07K 14/35* (2013.01); *A61K 39/04* (2013.01); *C12Q 1/6869* (2013.01); *A61K 39/00* (2013.01)

(58) Field of Classification Search
CPC ........ A61K 39/00; A61K 39/02; A61K 39/04; G01N 24/00; G01N 27/00
USPC ............................................ 424/234.1, 248.1
See application file for complete search history.

(56) References Cited

U.S. PATENT DOCUMENTS

| | | | |
|---|---|---|---|
| 5,386,373 A | 1/1995 | Keeler et al. | |
| 5,561,043 A | 10/1996 | Cantor et al. | |
| 5,777,078 A | 7/1998 | Bayley et al. | |
| 5,795,782 A | 8/1998 | Church et al. | |
| 5,817,771 A | 10/1998 | Bayley et al. | |
| 5,985,834 A | 11/1999 | Engel et al. | |
| 6,015,714 A | 1/2000 | Baldarelli et al. | |
| 6,123,819 A | 9/2000 | Peeters | |
| 6,127,166 A | 10/2000 | Bayley et al. | |
| 6,251,610 B1 | 6/2001 | Gupte et al. | |
| 6,362,002 B1 | 3/2002 | Denison et al. | |
| 6,426,231 B1 | 7/2002 | Bayley et al. | |
| 6,451,563 B1 | 9/2002 | Wittig et al. | |
| 6,627,067 B1 | 9/2003 | Branton et al. | |
| 6,824,659 B2 | 11/2004 | Bayley et al. | |
| 6,863,833 B1 | 3/2005 | Bloom et al. | |
| 6,916,665 B2 | 7/2005 | Bayley et al. | |
| 6,927,070 B1 | 8/2005 | Bayley et al. | |
| 7,087,729 B1 | 8/2006 | Prive | |
| 7,155,344 B1 | 12/2006 | Parce et al. | |
| 7,189,503 B2 | 3/2007 | Akeson et al. | |
| 8,105,846 B2 | 1/2012 | Bayley et al. | |
| 8,785,211 B2 | 7/2014 | Bayley et al. | |
| 8,822,160 B2 | 9/2014 | Bayley et al. | |
| 8,828,208 B2 | 9/2014 | Canas et al. | |
| 9,127,313 B2 | 9/2015 | Brown et al. | |
| 9,222,082 B2 | 12/2015 | Jayasinghe et al. | |
| 2002/0028458 A1 | 3/2002 | Lexow | |
| 2002/0094526 A1 | 7/2002 | Bayley et al. | |
| 2002/0168725 A1 | 11/2002 | Kobayashi et al. | |
| 2003/0044816 A1 | 3/2003 | Denison et al. | |
| 2003/0087232 A1 | 5/2003 | Christians et al. | |
| 2003/0099951 A1 | 5/2003 | Akeson et al. | |
| 2003/0108902 A1 | 6/2003 | Abarzua | |
| 2003/0118595 A1 | 6/2003 | Niemeyer et al. | |
| 2003/0166137 A1 | 9/2003 | Zuker et al. | |
| 2003/0211502 A1 | 11/2003 | Sauer et al. | |
| 2003/0215881 A1 | 11/2003 | Bayley et al. | |
| 2004/0214177 A1 | 10/2004 | Bension | |
| 2004/0229315 A1 | 11/2004 | Lee et al. | |
| 2005/0053961 A1 | 3/2005 | Akeson et al. | |
| 2005/0260655 A1 | 11/2005 | Liu et al. | |
| 2006/0063171 A1 | 3/2006 | Akeson et al. | |
| 2006/0105461 A1 | 5/2006 | Tom-Moy et al. | |
| 2007/0015182 A1 | 1/2007 | Abarzua | |
| 2007/0122885 A1 | 5/2007 | Reeves et al. | |
| 2007/0218471 A1 | 9/2007 | Kim et al. | |

(Continued)

FOREIGN PATENT DOCUMENTS

| | | |
|---|---|---|
| CA | 2381139 A1 | 3/2001 |
| GB | 2130219 | 5/1984 |

(Continued)

OTHER PUBLICATIONS

Butler, T.Z. et al. PNAS, vol. 105, No. 52, pp. 20647-20652, Dec. 2008.*
Stoddart, David et al., "Single-nucleotide discrimination in immobilized DNA oligonucleotides with a biological nanopore," PNAS, vol. 106(19):7702-7707 (2009).
Sutherland, Todd C. et al., "An analysis of mismatched duplex DNA unzipping through a bacterial nanopore," Biochem. Cell Biol., vol. 82:407-412 (2004).
Tadey, Tanya et al., "Capillary electrophoretic separation of nucleotide isomers via complexation with cyclodextrin and borate," Journal of Chromatography B, vol. 657:365-372 (1994).
Thomas, Kirk R. et al., "Processivity of DNA Exonucleases," The Journal of Biological Chemistry, vol. 253(2):424-429 (1978).

(Continued)

*Primary Examiner* — Rodney P Swartz
(74) *Attorney, Agent, or Firm* — Wolf, Greenfield & Sacks, P.C.

(57) ABSTRACT

The invention relates to mutant forms of Msp. The invention also relates to nucleic acid characterization using Msp.

26 Claims, 20 Drawing Sheets

(56) References Cited

U.S. PATENT DOCUMENTS

| | | |
|---|---|---|
| 2008/0069739 A1 | 3/2008 | Ludwig |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2010/0196203 A1 | 8/2010 | Sanghera et al. |
| 2010/0221212 A1 | 9/2010 | Stagliano et al. |
| 2010/0297638 A1 | 11/2010 | Bayley et al. |
| 2011/0019186 A1 | 1/2011 | Himmelhaus et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2013/0143802 A1 | 6/2013 | Chilkoti |
| 2013/0195908 A1 | 8/2013 | Leonetti et al. |
| 2014/0001056 A1 | 1/2014 | Bayley et al. |
| 2014/0051069 A1 | 2/2014 | Jayasinghe et al. |
| 2014/0206842 A1 | 7/2014 | Majeed et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0175663 A1 | 6/2015 | Yokoi et al. |
| 2015/0346149 A1 | 12/2015 | Brown et al. |

FOREIGN PATENT DOCUMENTS

| | | |
|---|---|---|
| GB | 2430763 | 4/2007 |
| GB | 2453377 | 4/2009 |
| JP | 11-137260 | 5/1999 |
| WO | 99/05167 A1 | 2/1999 |
| WO | 00/28312 A1 | 5/2000 |
| WO | 01/16327 A1 | 3/2001 |
| WO | 01/40516 A2 | 6/2001 |
| WO | 01/42782 A1 | 6/2001 |
| WO | 01/59453 A2 | 8/2001 |
| WO | 02/25934 A2 | 3/2002 |
| WO | 02/42496 A2 | 5/2002 |
| WO | 03/095669 A1 | 11/2003 |
| WO | 2005/056750 A2 | 6/2005 |
| WO | WO 2005/124888 | 12/2005 |
| WO | 2006/020575 A2 | 2/2006 |
| WO | 2006/028508 A2 | 3/2006 |
| WO | 2006/100484 A2 | 9/2006 |
| WO | 2007/005547 A1 | 1/2007 |
| WO | 2007/057668 A1 | 5/2007 |
| WO | 2007/075987 A2 | 7/2007 |
| WO | 2007/084103 A2 | 7/2007 |
| WO | 2008/045575 A2 | 4/2008 |
| WO | 2008/083554 A1 | 7/2008 |
| WO | 2008/102120 A1 | 8/2008 |
| WO | 2008/102121 A1 | 8/2008 |
| WO | 2008/124107 A1 | 10/2008 |
| WO | 2009/022152 A1 | 2/2009 |
| WO | 2009/024775 A1 | 2/2009 |
| WO | 2009/035647 A1 | 3/2009 |
| WO | 2009/044170 A1 | 4/2009 |
| WO | 2009/077734 A2 | 6/2009 |
| WO | 2009/143425 A1 | 11/2009 |
| WO | 2010/004265 A1 | 1/2010 |
| WO | 2010/004273 A1 | 1/2010 |
| WO | 2010/034018 A2 | 3/2010 |
| WO | 2010/055307 A1 | 5/2010 |
| WO | 2010/062913 A2 | 6/2010 |
| WO | 2010/086602 A1 | 8/2010 |
| WO | 2010/086603 A1 | 8/2010 |
| WO | 2010/086622 A1 | 8/2010 |
| WO | 2010/109107 A1 | 9/2010 |
| WO | 2010/122293 A1 | 10/2010 |
| WO | 2011/067559 A1 | 6/2011 |
| WO | 2012/042226 A2 | 4/2012 |
| WO | 2012/095660 A2 | 7/2012 |
| WO | 2012/164270 A1 | 12/2012 |

OTHER PUBLICATIONS

Tohda, Koji et al., "Channel Mimetic Sensing Membranes for Nucleotides Based on Multitopic Hydrogen Bonding," Israel Journal of Chemistry, vol. 37:267-275 (1997).

Travers, Kevin J. et al., "A flexible and efficient template format for circular consensus sequencing and SNP detection," Nucleic Acids Research, vol. 38(15):e159, doi:10.1093/nar/gkq543 (2010).

Tung, Ching-Hsuan, "Preparation and Applications of Peptide-Oligonucleotide Conjugates," Bioconjugate Chemistry, vol. 11(5):605-618 (2000).

Van De Goor, Tom A., "Nanopore Detection: Threading DNA Through a Tiny Hole," PharmaGenomics, vol. 4 (3):28-30 (2004).

Walker, Barbara et al., "Key Residues for Membrane Binding, Oligomerization and Pore Forming Activity of Staphylococcal alpha-Hemolysin Identified by Cysteine Scanning Mutagenesis and Targeted Chemical Modification," The Journal of Biological Chemistry, vol. 270 (39):23065-23071 (1995).

Wang, Qian et al., "Bioconjugation by Copper(I)-Catalyzed Azide-Alkyne [3 + 2] Cycloaddition," J. Am. Chem. Soc., vol. 125:3192-3193 (2003).

Wang, Hui et al., "Nanopores with a spark for single-molecule detection," Nature Biotechnology, vol. 19:622-623 (2001).

Wanunu, Meni et al., "DNA Translocation Governed by Interactions with Solid-State Nanopores," Biophysical Journal, vol. 95:4716-4725 (2008).

Weinstein, J.N. et al., "Liposome-cell interaction: transfer and intracellular release of a trapped fluorescent marker," Science, vol. 195(4277):489-492 (1977).

Wemmer, David E. et al., "Preparation and melting of single strand circular DNA loops," Nucleic Acids Research, vol. 13(23):8611-8621 (1985).

Winters-Hilt, Stephen et al., "Highly Accurate Classification of Watson-Crick Basepairs on Termini of Single DNA Molecules," Biophysical Journal, vol. 84:967-976 (2003).

Wolfe, Aaron J. et al., "Catalyzing the Translocation of Polypeptides through Attractive Interactions," J. Am. Chem. Soc., vol. 129:14034-14041 (2007).

Wong, C.T.A. et al., "Polymer capture by electro-osmotic flow of oppositely charged nanopores," The Journal of Chemical Physics, vol. 126:164903-1-164903-6 (2007).

Wu, Hai-Chen et al., "Protein Nanopores with Covalently Attached Molecular Adapters," J. Am. Chem. Soc., vol. 129:16142-16148 (2007).

Xie, Hongzhi et al., "Single-Molecule Observation of the Catalytic Subunit of cAMP-Dependent Protein Kinase Binding to an Inhibitor Peptide," Chemistry & Biology, vol. 12:109-120 (2005).

Yamagata, Atsushi et al., "Overexpression, purification and characterization of RecJ protein from Thermus thermophilus HB8 and its core domain," Nucleic Acids Research, vol. 29(22):4617-4624 (2001).

U.S. Appl. No. 12/093,610, filed Jul. 28, 2008, Hagan Bayley.
U.S. Appl. No. 12/681,643, filed Jun. 15, 2010, John Hagan Bayley.
U.S. Appl. No. 13/002,709, filed May 13, 2011, Lakmal Jayasinghe.
U.S. Appl. No. 13/968,778, filed Aug. 16, 2013, Lakmal Jayasinghe.
U.S. Appl. No. 13/002,717, filed Mar. 30, 2011, James Clarke.
U.S. Appl. No. 13/129,278, filed Aug. 26, 2011, Giovanni Maglia.
U.S. Appl. No. 14/144,573, filed Nov. 26, 2013, James Clarke.
U.S. Appl. No. 13/147,171, filed Nov. 10, 2011, Ruth Moysey.
U.S. Appl. No. 14/071,731, filed Nov. 5, 2013, Ruth Moysey.
U.S. Appl. No. 13/147,159, filed Nov. 15, 2011, Brian McKeown.
U.S. Appl. No. 13/147,176, filed Nov. 18, 2011, Lakmal Jayasinghe.
U.S. Appl. No. 13/260,178, filed Jan. 17, 2012, David Stoddart.
U.S. Appl. No. 13/512,937, filed Sep. 6, 2012, Clive Gavin Brown.

(56) References Cited

OTHER PUBLICATIONS

U.S. Appl. No. 13/979,584, filed Sep. 19, 2013, John Hagan Pryce Bayley.
U.S. Appl. No. 12/093,610, office action dated Sep. 27, 2011, Stephen Thomas Kapushoc.
U.S. Appl. No. 12/093,610, office action dated filed Apr. 4, 2011, Stephen Thomas Kapushoc.
U.S. Appl. No. 12/093,610, office action dated Sep. 29, 2010, Stephen Thomas Kapushoc.
U.S. Appl. No. 12/093,610, office action dated Jan. 22, 2010, Stephen Thomas Kapushoc.
U.S. Appl. No. 12/093,610, office action dated Oct. 6, 2009, Stephen Thomas Kapushoc.
U.S. Appl. No. 12/681,643, office action dated Nov. 6, 2013, Ruixiang Li.
U.S. Appl. No. 12/681,643, office action dated Mar. 8, 2013, Ruixiang Li.
U.S. Appl. No. 12/681,643, office action dated Jul. 10, 2012, Ruixiang Li.
U.S. Appl. No. 12/681,643, office action dated Dec. 21, 2011, Ruixiang Li.
U.S. Appl. No. 12/681,643, office action dated Sep. 6, 2011, Ruixiang Li.
U.S. Appl. No. 13/002,709, office action dated Jun. 27, 2013, Marianne P. Allen.
U.S. Appl. No. 13/002,709, office action dated Dec. 21, 2012, Sandra L. Wegert.
U.S. Appl. No. 13/002,717, office action dated Dec. 20, 2012, Sandra L. Wegert.
U.S. Appl. No. 13/129,278, office action dated Jun. 11, 2013, Ruixiang Li.
U.S. Appl. No. 13/129,278, office action dated Feb. 27, 2013, Ruixiang Li.
U.S. Appl. No. 13/147,171, office action dated May 6, 2013, Nashaat T. Nashed.
U.S. Appl. No. 13/147,171, office action dated Jan. 3, 2013, Nashaat T. Nashed.
U.S. Appl. No. 13/147,159, office action dated May 28, 2013, Joseph G. Dauner.
U.S. Appl. No. 13/147,159, office action dated Jan. 25, 2013, Joseph G. Dauner.
U.S. Appl. No. 13/260,178, office action dated May 9, 2013, Robert Thomas Crow.
U.S. Appl. No. 13/260,178, office action dated Feb. 20, 2013, Robert Thomas Crow.
Akeson, Mark et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77:3227-3233 (1999).
Amblard, Franck et al., "The Cu(I)-catalyzed Huisgen azide-alkyne 1,3-dipolar cycloaddition reaction in nucleotide and oligonucleotide chemistry," Chem. Rev., vol. 109(9):4207-4220 (2009).
Ashkenasy, Nurit et al., "Recognizing a Single Base in an Individual DNA Strand: A Step Toward DNA Sequencing in Nanopores," Angew. Chem. Int. Ed., vol. 44:1401-1404 (2005).
Ashkenasy, Nurit et al., "Single Nucleobase Sensitivity of a-Hemolysin (a-HL) Transmembrane Protein Pore: Toward Single DNA Sequencing," ACS National Meeting, vol. 45(13), Abstract No. 74 (2005).
Astier, Yann et al., "Stochastic Detection of Motor Protein-RNA Complexes by Single-Channel Current Recording," ChemPhysChem, vol. 8:2189-2194 (2007).
Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecule Adapter," J. Am. Chem. Soc., vol. 128(5):1705-1710 (2006).
Bayley, H., "Membrane-protein structure: Piercing insights," Nature, vol. 459(7247):651-652 (2009).
Bayley, Hagan, "Sequencing single molecules of DNA," Current Opinion in Chemical Biology, vol. 10:628-637 (2006).
Bayley, Hagan et al., "Stochastic sensors inspired by biology," Nature, vol. 413:226-230 (2001).
Bayely, H. et al., "Wrestling with native chemical ligation," ACS Chem. Biol., vol. 4(12):983-985 (2009).
Benner, Seico et al., "Sequence-specific detection of individual DNA polymerase complexes in real time using a nanopore," Nature Nanotechnology, vol. 2:718-724 (2007).
Braha, Orit et al., "Carriers versus Adapters in Stochastic Sensing," ChemPhysChem, vol. 6:889-892 (2005).
Braha, Orit et al., "Designed protein pores as components for biosensors," Chemistry & Biology, vol. 4:497-505 (1997).
Branton, Daniel et al., "The potential and challenges of nanopore sequencing," Nat. Biotechnol., vol. 26 (10):1146-1153 (2008).
Braslavsky, Ido et al., "Sequence information can be obtained from single DNA molecules," PNAS, vol. 100 (7):3960-3964 (2003).
Breyton, C. et al., "Hemifluorinated surfactants: a non-dissociating environment for handling membrane proteins in aqueous solutions?" FEBS Letters, vol. 564(3):312-318 (2004).
Budanova, Natalia et al., "Heptakis(6-amino-6-deoxy)-beta-cyclodextrin as a chiral selector for the separation of anionic analyte enantiomers by capillary electrophoresis," Electrophoresis, vol. 25:2795-2800 (2004).
Busam, Robert D., "Structure of *Escherichia coli* exonuclease I in complex with thymidine 5'-monophosphate," Acta Cryst., vol. D64:206-210 (2008).
Butler, Tom Z. et al., "Determination of RNA Orientation during Translocation through a Biological Nanopore," Biophysical Journal, vol. 90:190-199 (2006).
Butler, Tom Z. et al., "Single-molecule DNA detection with an engineered MspA protein nanopore," PNAS, vol. 105 (52):20647-20652 (2008).
Chabaud, E. et al., "Stabilization of integral membrane proteins in aqueous solution using fluorinated surfactants," Biochimie, vol. 80(5-6):515-530 (1998).
Chan, Eugene Y., "Advances in sequencing technology," Mutation Research, vol. 573:13-40 (2005).
Cheley, Stephen et al., "A functional protein pore with a 'retro' transmembrane domain," Protein Science, vol. 8:1257-1267 (1999).
Cheley, Stephen et al., "A Genetically Encoded Pore for the Stochastic Detection of a Protein Kinase," ChemBioChem, vol. 7:1923-1927 (2006).
Cheley, Stephen et al., "Spontaneous oligomerization of a staphylococcal alpha-hemolysin conformationally constrained by removal of residues that form the transmembrane beta-barrel," Protein Engineering, vol. 10 (12):1433-1443 (1997).
Cheley, Stephen et al., "Stochastic Sensing of Nanomolar Inositol 1,4,5-Triphosphate with an Engineered Pore," Chemistry & Biology, vol. 9:829-838 (2002).
Chen, Peng et al., "Atomic Layer Deposition to Fine-Tune the Surface Properties and Diameters of Fabricated Nanopores," Nano Letters, vol. 4(7):1333-1337 (2004).
Chen, Min et al., "Outer membrane protein G: Engineering a quiet pore for biosensing," PNAS, vol. 105 (17):6272-6277 (2008).
Clarke, James et al., "Continuous base identification for single-molecule nanopore DNA sequencing," Nature Nanotechnology, vol. 4:265-270 (2009).
Cockroft, Scott L. et al., "A Single-Molecule Nanopore Device Detects DNA Polymerase Activity with Single-Nucleotide Resolution," J.Am. Chem. Soc., vol. 130:818-820 (2008).
Colas, J.C. et al., "Microscopical investigations of nisin-loaded nanoliposomes prepared by Mozafari method and their bacterial targeting," Micron, vol. 38(8):841-847 (2007).
Comai, Massimiliano et al., "Protein engineering modulates the transport properties and ion selectivity of the pores formed by staphylococcal y-haemolysins in lipid membranes," Molecular Microbiology, vol. 44(5):1251-1267 (2002).
Cudic, Predrag et al., "Binding of Nucleotides in Water by Phenathridinium Bis(intercaland) Receptor Molecules," J. Chem. Soc., Chem. Commun., pp. 1073-1075 (1995).
Dapprich, Johannes, "Single-Molecule DNA Digestion by Lambda-Exonuclease," Cytometry, vol. 36:163-168 (1999).

(56) References Cited

OTHER PUBLICATIONS

Deamer, David W. et al., "Characterization of Nucleic Acids by Nanopore Analysis," Ac. Chem. Res., vol. 35:817-825 (2002).
Deamer, David W. et al., "Nanopores and nucleic acids: prospects for ultrarapid sequencing," TIBTECH, vol. 18:147-151 (2000).
Deck, Kathryn M. et al., "Triisopropyltriazacyclononane Copper(II): An Efficient Phosphodiester Hydrolysis Catalyst and DNA Cleavage Agent," Inorganic Chemistry, vol. 41(4):669-677 (2002).
Derrington, Ian M. et al., "A Novel DNA Sensing Technique Using Nanopore MSPA," 54th Annual Meeting of the Biophysical Society, Poster 2182-Plat, 2 pages (2010).
Derrington, Ian M. et al., "Nanopore DNA sequencing with MspA," PNAS, vol. 107(37):16060-16065 (2010).
Dorre, Klaus et al., "Techniques for single molecule sequencing," Bioimaging, vol. 5:139-152 (1997).
Eid, John et al., "Real-Time DNA Sequencing from Single Polymerase Molecules," Science, vol. 323:133-138 (2009).
Eliseev, Alexey V. et al., "Aminocyclodextrins as Selective Hosts with Several Binding Sites for Nucleotides," Angew. Chem. Int. Ed. Engl., vol. 32(9):1331-1333 (1993).
Eliseev, Alexey V. et al., "Molecular Recognition of Nucleotides, Nucleosides, and Sugars by Aminocyclodextrins," J. Am. Chem. Soc., vol. 116:6081-6088 (1994).
Engelhardt, Harald et al., "A Tetrameric Porin Limits the Cell Wall Permeability of Mycobacterium smegmatis," The Journal of Biological Chemistry, vol. 277(40):37567-37572 (2002).
Erie, Dorothy et al., "A Dumbell-Shaped, Double-Hairpin Structure of DNA: A Thermodynamic Investigation," Biochemistry, vol. 26:7150-7159 (1987).
Eroglu, Ali et al., "Intracellular trehalose improves the survival of cryopreserved mammalian cells," Nature Biotechnology, vol. 18:163-167 (2000).
Faller, Michael et al., "The Structure of a Mycobacterial Outer-Membrane Channel," Science, vol. 303:1189-1192 (2004).
Flomembom, O. et al., Single stranded DNA translocation through a nanopore: A master equation approach, Physical Review E, vol. 68:041910, DOI: 10.1103/PhysRevE.68.041910, 7 pages, (2003).
Flusberg, Benjamin A. et al., "Direct detection of DNA methylation during single-molecule, real-time sequencing," Nature Methods, vol. 7(6):461-465 (2010).
Genschel, Jochen et al., "Interaction of E. coli Single-Stranded DNA Binding Protein (SSB) with Exonuclease I. The Carboxy-Terminus of SSB Is the Recognition Site fo the Nuclease," Biol, Chem., vol. 381:183-192 (2000).
U.S. Appl. No. 14/122,573, filed Apr. 16, 2014, James Clarke.
U.S. Appl. No. 14/455,394, filed Aug. 8, 2014, Lakmal Jayasinghe.
U.S. Appl. No. 14/334,285, filed Jul. 7, 2014, Giovanni Maglia.
U.S. Appl. No. 14/302,303, filed Jun. 11, 2014, Clive Gavin Brown.
U.S. Appl. No. 12/681,643, filed Jun. 15, 2010, John Hagan Bayley, office action dated Apr. 24, 2014.
U.S. Appl. No. 13/002,709, filed May 13, 2011, Lakmal Jayasinghe, office action dated Mar. 10, 2014.
U.S. Appl. No. 13/002,717, filed Mar. 30, 2011, James Clarke, office action dated Jul. 21, 2015.
U.S. Appl. No. 13/002,717, filed Mar. 30, 2011, James Clarke, office action dated Mar. 17, 2015.
U.S. Appl. No. 13/002,717, filed Mar. 30, 2011, James Clarke, office action dated Mar. 12, 2014.
U.S. Appl. No. 13/002,717, filed Mar. 30, 2011, James Clarke, office action dated Apr. 3, 2014.
U.S. Appl. No. 13/129,278, filed Aug. 26, 2011, Giovanni Maglia, office action dated Feb. 18, 2014.
U.S. Appl. No. 13/147,159, filed Nov. 15, 2011, Brian McKeown, office action dated Mar. 20, 2015.
U.S. Appl. No. 13/147,159, filed Nov. 15, 2011, Brian McKeown, office action dated Jul. 17, 2014.
U.S. Appl. No. 13/147,159, filed Nov. 15, 2011, Brian McKeown, office action dated Dec. 18, 2013.
U.S. Appl. No. 13/147,176, filed Nov. 18, 2011, Lakmal Jayasinghe, office action dated May 8, 2015.
U.S. Appl. No. 13/147,176, filed Nov. 18, 2011, Lakmal Jayasinghe, office action dated Oct. 20, 2014.
U.S. Appl. No. 13/147,176, filed Nov. 18, 2011, Lakmal Jayasinghe, office action dated Mar. 14, 2014.
U.S. Appl. No. 13/260,178, filed Jan. 17, 2012, David Stoddart, office action dated Feb. 26, 2015.
U.S. Appl. No. 13/260,178, filed Jan. 17, 2012, David Stoddart, office action dated Jan. 14, 2014.
U.S. Appl. No. 13/512,937, filed Sep. 6, 2012, Clive Gavin Brown, office action dated May 8, 2015.
U.S. Appl. No. 13/512,937, filed Sep. 6, 2012, Clive Gavin Brown, office action dated Nov. 7, 2014.
U.S. Appl. No. 13/968,778, filed Aug. 16, 2013, Lakmal Jayasinghe, office action dated Mar. 20, 2015.
U.S. Appl. No. 13/968,778, filed Aug. 16, 2013, Lakmal Jayasinghe, office action dated Jul. 9, 2014.
U.S. Appl. No. 14/334,285, filed Jul. 17, 2014, Giovanni Maglia, office action dated Feb. 9, 2015.
U.S. Appl. No. 14/455,394, filed Aug. 8, 2014, Lakmal Jayasinghe, office action dated May 8, 2015.
Gershow, Marc et al., "Recapturing and trapping single molecules with a solid-state nanopore," Nature Nanotechnology, vol. 2:775-779 (2007).
Ghosal, Sandip, "Electrokinetic-flow-induced viscous drag on a tethered DNA inside a nanopore," Physical Review E, vol. 76:061916, DOI: 10.1103/PhysRevE.76.061916, 3 pages, (2007).
Gonzalez-Perez, Alfredo et al., "Biomimetic Triblock Copolymer Membrane Arrays: A Stable Template for Functional Membrane Proteins," Langmuir, vol. 25(18):10447-10450 (2009).
Gu, Li-Qun et al., "Capture of a Single Molecule in a Nanocavity," Science, vol. 291:636-640 (2001).
Gu, Li-Qun et al., "Electroosmotic enhancement of the binding of a neutral molecule to a transmembrane pore," PNAS, vol. 100(26):15498-15503 (2003).
Gu, Li-Qun et al., "Interaction of the Noncovalent Molecular Adapter, beta-Cyclodextrin, with the STaphylococcal alpha-Hemolysin Pore," Biophysical Journal, vol. 79:1967-1975 (2000).
Gu, Li-Qun et al., "Prolonged Residence Time of a Noncovalent Molecular Adapter, beta-Cyclodextrin, within the Lumen of Mutant alpha-Hemolysin Pores," J. Gen. Physiol., vol. 118:481-493 (2001).
Gu, Li-Qun et al., "Reversal of charge selectivity in transmembrane protein pores by using noncovalent molecular adapters," PNAS, vol. 97(8):3959-3964 (2000).
Gu, Li-Qun et al., "Stochastic sensing of organic analytes by a pore-forming protein containing a molecular adapter," Nature, vol. 398:686-690 (1999).
Guan, Xiyun et al., "Stochastic Sensing of TNT with a Genetically Engineered Pore," ChemBioChem, vol. 6:1875-1881 (2005).
Hall, Adam R. et al., "Hybrid pore formation by directed insertion of alpha hemolysin into solid-state nanopores," Nat. Nanotechnol., vol. 5(12):874-877 (2010).
Han, Jongyoon et al., "Characterization and Optimization of an Entropic Trap for DNA Separation," Anal. Chem., vol. 74:394-401 (2002).
Han, Eugene S. et al., "RecJ exonuclease: substrates, products and interaction with SSB," Nucleic Acids Research, vol. 34(4):1084-1091 (2006).
Hein, Christopher D. et al., "Click Chemistry, a Powerful Tool for Pharmaceutical Sciences," Pharm. Res., vol. 25 (10):2216-2230 (2008).
Heinz, Christian et al., "The Core of the Tetrameric Mycobacterial Porin MspA Is an Extremely Stable beta-Sheet Domain," The Journal of Biological Chemistry, vol. 278(10):8678-8685 (2003).
Helicos BioSciences Corporation, "Helicos Genetic Analysis System," Specification Sheet retrieved online at: www.helicosbio.com/Portals/0/Documents/Helicos_SalesSpec.pdf, 4 pages (2008).
Henrickson, Sarah E. et al., "Driven DNA Transport into an Asymmetric Nanometer-Scale Pore," Physical Review Letters, vol. 85(14):3057-3060 (2000).
Heron, A.J. et al., "Direct detection of membrane channels from gels using water-in-oil droplet bilayers," J. Am. Chem. Soc., vol. 129(51):16042-16047 (2007).

(56) References Cited

OTHER PUBLICATIONS

Hillmann, Dietmar et al., "Expression of the Major Porin Gene msp4 Is Regulated in *Mycobacterium smegmatis*," Journal of Bacteriology, vol. 189(3):958-967 (2007).

Holden, Matthew A. et al., "Direct Introduction of Single Protein Channels and Pores into Lipid Bilayers," J. Am. Chem. Soc., vol. 127:6502-6503 (2005).

Holden, Matthew A. et al., "Functional Bionetworks from Nanoliter Water Droplets," J. Am. Chem. Soc., vol. 129:8650-8655 (2007).

Hornblower, Breton et al., "Single-molecule analysis of DNA-protein complexes using nanopores," Nature Methods, vol. 4(4):315-317 (2007).

Howorka, Stefan et al., "DNA Duplex Formation of Individual DNA Strands within a Single Protein Pore," Biophysical Journal, vol. 82(1, pt. 2):508a, No. 2482-Plat (2002).

Howorka, S. et al., "Improved Protocol for High-Throughput Cysteine Scanning Mutagenesis," Biotechniques, vol. 25(5):764-766 (1998).

Howorka, Stefan et al., "Kinetics of duplex formation for individual DNA strands within a single protein nanopore," PNAS, vol. 98(23):12996-13001 (2001).

Howarka, Stefan et al., "Probing Distance and Electrical Potential within a Protein Pore with Tethered DNA," Biophysical Journal, vol. 83:3202-3210 (2002).

Howorka, Stefan et al., "Sequence-specific detection of individual DNA strands using engineered nanopores," Nature Biotechnology, vol. 19:636-639 (2001).

Hu, Tao et al., "Theory of DNA translocation through narrow ion channels and nanopores with charged walls," Physical Review E, vol. 78:032901, DOI: 10.1103/PhysRevE.78.032901, 3 pages, (2008).

Hwang, William L. et al., "Electrical Behavior of Droplet Interface Bilayer Networks: Experimental Analysis and Modeling," J. Am. Chem. Soc., vol. 129:11854-11864 (2007).

Inman, J.T. et al., "A high-throughput distributed DNA sequence analysis and database system," IBM Systems Journal, vol. 40(2):464-486 (2001).

Jayasinghe, Lakmal et al., "The leukocidin pore: Evidence for an octamer with four LukF subunits and four LukS subunits alternating around a central axis," Protein Science, vol. 14:2550-2561 (2005).

Jung, Yuni et al., "The Internal Cavity of the Staphylococcal alpha-Hemolysin Pore Accommodates ~175 Exogenous Amino Acid Residues," Biochemistry, vol. 44(25):8919-8929 (2005).

Kalisch, Bernd W. et al., "Covalently linked sequencing primer linkers (splinkers) for sequence analysis of restriction fragments (Recombinant DNA; hairpin ligation; synthetic oligodeoxynucleotides; dideoxynucleotides)," Gene, vol. 44:263-270 (1986).

Kang, Xiao-feng et al., "Single Protein Pores Containing Molecular Adapters at High Temperatures," Angew. Chem. Int. Ed., vol. 44:1495-1499 (2005).

Kartmann, Bettina et al., "Porins in the Cell Wall of *Mycobacterium tuberculosis*," Journal of Bacteriology, vol. 181 (20):6543-6546 (1999).

Kasianowicz, John J. et al., "Characterization of individual polynucleotide molecules using a membrane channel," Proc. Natl. Acad. Sci. USA, vol. 93:13770-13773 (1996).

Khulbe, Pramod K. et al., "DNA translocation through a-hemolysin nanopores with potential application to macromolecular data storage," Journal of Applied Physics, vol. 97(104317):1-7 (2005).

Kocalka, Petr et al., "Rapid and Efficient DNA Strand Cross-Linking by Click Chemistry," ChemBioChem, vol. 9:1280-1285 (2008).

Kolb, Hartmuth C. et al., "Click Chemistry: Diverse Chemical Function from a Few Good Reactions," Angew. Chem. Int. Ed., vol. 40:2004-2021 (2001).

Kovall, Rhett et al., "Toroidal Structure of Lambda-Exonuclease," Science, vol. 277:1824-1827 (1997).

Li, Jiali et al., "DNA molecules and configurations in a solid-state nanopore microscope," Nature, vol. 2:611-615 (2003).

Lieberman, Kate R. et al., "Processive Replication of Single DNA Molecules in an Nanopore Catalyzed by phi29 DNA Polymerase," J. Am. Chem. Soc., vol. 132:17961-17972 (2010).

Lovett, Susan T. et al., "Identification and purification of a single-stranded-DNA-specific exonuclease encoded by the recJ gene of *Escherichia coli*," Proc. Natl. Acad. Sci. USA, vol. 86:2627-2631 (1989).

Lovrinovic, Marina et al., "Rapid synthesis of DNA-cysteine conjugates for expressed protein ligation," Biochemical and Biophysical Research Communications, vol. 335:943-948 (2005).

Luo, Kaifu et al., "Influence of Polymer-Pore Interactions on Translocation," Physical Review Letters, vol. 99:148102, DOI: 10.1103/PhysRev Lett. 99.148102, 4 pages, (2007).

Lutz, Jean-Francois et al., "Efficient construction of therapeutics, bioconjugates, biomaterials and bioactive surfaces using azide-alkyne 'click' chemistry," Advanced Drug Delivery Reviews, vol. 60:958-970 (2008).

Maglia, G. et al., "DNA strands from denatured duplexes are translocated through engineered protein nanopores at alkaline pH," Nano Letters, vol. 9(11):3831-3836 (2009).

Maglia, Giovanni et al., "Enhanced translocation of single DNA molecules through alpha-hemolysin nanopores by manipulation of internal charge," PNAS, vol. 105(50):19720-19725 (2008).

Mahfoud, Maysa et al., "Topology of the Porin MspA in the Outer Membrane of *Mycobacterium smegmatis*," Journal of Biological Chemistry, vol. 281(9):5908-5915 (2006).

Mailaender, Claudia et al., "The MspA porin promotes growth and increases antibiotic susceptibility of both *Mycobacterium bovis* BCG and *Mycobacterium tuberculosis*," Microbiology, vol. 150:853-864 (2004).

Manrao, Elizabeth A. et al., "Nucleotide Discrimination with DNA Immobilized in the MspA Nanopore," PLoS One, vol. 6(10):e25723, 7 pages (2011).

Manrao, Elizabeth A. et al., "Single Nucleotide Discrimination in Single Stranded DNA Immobilized within Biological Nanopre MSPA," 54th Annual Meeting of the Biophysical Society, 3 pages (2010).

Martin, Hugh et al., "Nanoscale Protein Pores Modified with PAMAM Dendrimers," J. Am. Chem. Soc., vol. 129:9640-9649 (2007).

Martínez, Javier et al., "The mRNA Cap Structure Stimulates Rate of Poly(A) Removal and Amplifies Processivity of Degradation," The Journal of Biological Chemistry, vol. 276(30):27923-27929 (2001).

Marziali, Andre et al., "New DNA Sequencing Methods," Annu. Rev. Biomed. Eng., vol. 3:195-223 (2001).

Mathé, Jeéôme et al., "Orientation discrimination of a single-stranded DNA inside the a-hemolysin membrane channel," PNAS, vol. 102(35):12377-12382 (2005).

Matsuura, Shun-ichi et al., "Real-time observation of a single DNA digestion by I exonuclease under a fluorescence microscope field," Nucleic Acids Research, vol. 29(16):1-5 (2001).

Meller, Amit, "Dynamics of polynucleotide transport through nanometre-scale pores," Journal of Physics: Condensed Matter, vol. 15:R581-R607 (2003).

Meller, Amit et al., "Rapid nanopore discrimination between single polynucleotide molecules," PNAS, vol. 97 (3):1079-1084 (2000).

Meller, Amit et al., "Single molecule measurements of DNA transport through a nanopore," Electrophoresis, vol. 23: 2583-2591 (2002).

Merzlyak, Petr G. et al., "Conductance and Ion Selectivity of a Mesoscopic Protein Nanopore Probed with Cysteine Scanning Mutagenesis," Biophysical Journal, vol. 89:3059-3070 (2005).

Miles, George et al., "Properties of Bacillus cereus hemolysin II: A heptameric transmembrane pore," Protein Science, vol. 11:1813-1824 (2002).

Mitchell, Nick et al., "Chemical Tags Facilitate the Sensing of Individual DNA Strands with Nanopores," Angew. Chem. Int. Ed., vol. 47:5565-5568 (2008).

Mohammad, Mohammad M. et al., "Controlling a Single Protein in a Nanopore through Electrostatic Traps," J. Am. Chem. Soc., vol. 130:4081-4088 (2008).

(56) References Cited

OTHER PUBLICATIONS

Mol, Clifford D. et al., "Structure and function of the multifunctional DNA-repair enzyme exonuclease III," Nature, vol. 374:381-386 (1995).
Moreau, C.J. et al., "Coupling ion channels to receptors for biomolecule sensing," Nat. Nanotechnol., vol. 3 (10):620-625 (2008).
Movileanu, Llviu et al., "Detecting protein analytes that modulate transmembrane movement of a polymer chain within a single protein pore," Nature Biotechnology, vol. 18:1091-1095 (2001).
Movileanu, Liviu et al., "Location of a Construction in the Lumen of a Transmembrane Pore by Targeted Covalent Attachment of Polymer Molecules," J. Gen. Physiol., vol. 117:239-251 (2001).
Muller, Joachim et al., "DNA-directed assembly of artificial multienzyme complexes," Biochemical and Biophysical Research Communications, vol. 377:62-67 (2008).
Nakane, Jonathan et al., "A Nanosensor for Transmembrane Capture and Identification of Single Nucleic Acid Molecules," Biophysical Journal, vol. 87:615-621 (2004).
Nakane, Jonathan J. et al., "Nanopore sensors for nucleic acid analysis," J. Phys.: Condens. Matter, vol. 15:R1365-R1393 (2003).
Niederweis, Michael et al., "Cloning of the mspA gene encoding a porin from *Mycobacterium smegmatis*," Molecular Microbiology, vol. 33(5):933-945 (1999).
Niederweis, Michael, "Mycobacterial porins—new channel proteins in unique outer membranes," Molecular Microbiology, vol. 49(5):1167-1177 (2003).
Niemeyer, Christof M. et al., "DNA-Directed Assembly of Bienzymic Complexes from In Vivo Biotinylated NAD(P)H: FMN Oxidoreductase and Luciferase," ChemBioChem., vol. 3:242-245 (2002).
Nwe, Kido et al., "Growing Applications of 'Click Chemistry' for Bioconjugation in Comtemporary Biomedical Research," Cancer Biotherapy and Radiopharmaceuticals, vol. 24(3):289-302 (2009).
Palchevskyy, S.S. et al., "Chaperoning of insertion of membrane proteins into lipid bilayers by hemifluorinated surfactants: applications to diphtheria toxin," Biochemistry, vol. 45(8):2629-2635 (2006).
Paner, Teodoro M. et al., "Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14)," Biopolymers, vol. 32(7):881-892 (1992).
Paner, Teodoro M. et al., "Studies of DNA Dumbells. VI. Analysis of Optical Melting Curves of Dumbells with a Sixteen-Base Pair Duplex Stem and End-Loops of Variable Size and Sequence," Biopolymers, vol. 39:779-793 (1996).
Park, Kyu-Ho et al., "Fluorinated and hemifluorinated surfactants as alternatives to detergents for membrane protein cell-free synthesis," Biochem. J., vol. 403:183-187 (2007).
Phoenix, David A. et al., "OmpF-LPP Signal Sequence Mutants with Varying Charge Hydrophobicity Ratios Provide Evidence for a Phosphatidylglycerol-Signal Sequence Interaction during Protein Translocation across the *Escherichia coli* Inner Membrane," The Journal of Biological Chemistry, vol. 268(23):17069-17073 (1993).
Plugge, B. et al., "A potassium channel protein encoded by chlorella virus PBCV-1," Science, vol. 287 (5458):1641-1644 (2000).
Posokhov, Yevgen O. et al., "FCS Study of the Thermodynamics of Membrane Protein Insertion into the Lipid Bilayer Chaperoned by Fluorinated Surfactants," Biophysical Journal: Biophysical Letters, vol. 95:L54-L56 (2008).
Purnell, Robert F. et al., "Nucleotide Identificaiton and Orientation Discrimination of DNA Homopolymers Immobilized in a Protein Nanopore," Nano Letters, vol. 8(9):3029-3034 (2008).
Raychaudhuri, P. et al., "Fluorinated amphiphiles control the insertion of alpha-hemolysin pores into lipid bilayers," Biochemistry, vol. 50(10):1599-1606 (2011).
Rhee, Minsoung et al., "Nanopore sequencing technology: research trends and applications," Trends in Biotechnology, vol. 24(12):580-586 (2006).

Rodnin, Mykola V. et al., "Interactions of Fluorinated Surfactants with Diphtheria Toxin T-Domain: Testing New Media for Studies of Membrane Proteins," Biophysical Journal, vol. 94:4348-4357 (2008).
Russo, M.J. et al., "Reversible permeabilization of plasma membranes with an engineered switchable pore," Nature Biotechnology, vol. 15(3):278-282 (1997).
Sanchez-Quesada, Jorge et al., "Cyclic Peptides as Molecular Adapters for a Pore-Forming Protein," Journal of the American Chemical Society, vol. 122(48):11757-11766 (2000).
Sanchez-Quesada, Jorge et al., "Single DNA Rotaxanes of a Transmembrane Pore Protein," Angew. Chem. Int. Ed., vol. 43:3063-3067 (2004).
Sanderson, Katherine, "Standard and Pores. Could the next generation of genetic sequencing machines be built froma collection of miniscule holes?" Nature News, vol. 456(7218):23-25 (2008).
Sauer-Budge, Alexis F. et al., "Unzipping Kinetics of Double-Stranded DNA in a Nanopore," Phys. Rev. Letters, vol. 90(23):238101-1-238101-4 (2003).
Seeman, Nadrian C., "Nucleic Acid Junctions and Lattices," J. theor. Biol., vol. 99:237-247 (1982).
Seo, Tae Seok et al., "Click Chemistry to Construct Fluorescent Oligonucleotides for DNA Sequencing," J. Org. Chem., vol. 68:609-612 (2003).
Seol, Yeonee, Stretching of Homopolymeric RNA Reveals Single-Stranded Helices and Base-Stacking, Physical Review Letters, vol. 98:158103, DOI: 10.1103/PhysRevLett.98.158103, 4 pages, (2007).
Shank, Lalida P. et al., "Redesigning Channel-Forming Peptides: Amino Acid Substitutions that Enhance Rates of Supramolecular Self-Assembly and Raise Ion Transport Activity," Biophysical Journal, vol. 90:2138-2150 (2006).
Shin, Seong-Ho et al., "Kinetics of a Reversible Covalent-Bond-Forming Reaction Observed at the Single-Molecule Level," Angew. Chem. Int Ed., vol. 41(19):3707-3709 (2002).
Smeets, Ralph M.M. et al., "Salt Dependence of Ion Transport and DNA Translocation through Solid-State Nanopores," Nano Letters, vol. 6(1):89-95 (2006).
Song, Langzhou et al., "Structure of Staphylococcal alpha-Hemolysin, a Heptameric Transmembrane Pore," Science, vol. 274:1859-1866 (1996).
Stahl, Claudia et al., "MspA provides the main mydrophilic pathway through the cell wall of *Mycobacterium smegmatis*," Molecular Microbiology, vol. 40(2):451-464 (2001).
Stoddart, David et al., "Multiple base-recognition sites in a biological nanopore—two heads are better than one," Angew. Chem. Int Ed. Engl., vol. 49(3):556-559 (2010).
U.S. Appl. No. 13/338,794, filed Dec. 28, 2011, Hagan Bayley.
U.S. Appl. No. 14/858,138, filed Sep. 18, 2015, Lakmal Jayasinghe.
U.S. Appl. No. 14/812,510, filed Jul. 29, 2015, Clive Gavin Brown.
U.S. Appl. No. 13/338,794, filed Dec. 28, 2011, Hagan Bayley, office action dated Mar. 13, 2014.
U.S. Appl. No. 13/338,794, filed Dec. 28, 2011, Hagan Bayley, office action dated Mar. 5, 2013.
U.S. Appl. No. 13/338,794, filed Dec. 28, 2011, Hagan Bayley, office action dated Sep. 24, 2012.
U.S. Appl. No. 13/338,794, filed Dec. 28, 2011, Hagan Bayley, office action dated Jul. 19, 2012.
U.S. Appl. No. 14/455,394, filed Aug. 8, 2014, Lakmal Jayasinghe, office action dated Oct. 2, 2015.
U.S. Appl. No. 14/334,285, filed Jul. 17, 2014, Giovanni Maglia, office action dated Dec. 3, 2015.
U.S. Appl. No. 14/334,285, filed Jul. 17, 2014, Giovanni Maglia, office action dated Aug. 21, 2015.
U.S. Appl. No. 13/147,159, filed Nov. 15, 2011, Brian Mckeown, office action dated Oct. 20, 2015.
U.S. Appl. No. 13/147,176, filed Nov. 18, 2011, Lakmal Jayasinghe, office action dated Aug. 31, 2015.
U.S. Appl. No. 13/260,178, filed Jan. 17, 2012, David Stoddart, office action dated Aug. 18, 2015.
Dani, Raj Kumar et al., "MspA Porin-Gold Nanoparticle Assemblies: Enhanced Binding through a Controlled Cysteine Mutation," Nano Letters, vol. 8(4) pp. 1229-1236 (2008).

(56) References Cited

OTHER PUBLICATIONS

Altschul et al., Basic local alignment search tool. J Mol Biol. Oct. 5, 1990;215(3):403-10.
Altschul, A protein alignment scoring system sensitive at all evolutionary distances. J Mol Evol. Mar. 1993;36(3):290-300.
Aoki et al., Single channel properties of lysenin measured in artificial lipid bilayers and their applications to biomolecule detection. Proc Jpn Acad Ser B Phys Biol Sci. 2010;86(9):920-5.
Avrameas, Coupling of enzymes to proteins with glutaraldehyde. Use of the conjugates for the detection of antigens and antibodies. Immunochemistry. Jan. 1969;6(1):43-52.
Bowie et al., Deciphering the message in protein sequences: tolerance to amino acid substitutions. Science. Mar. 16, 1990;247(4948):1306-10.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
De Colibus et al., Structures of lysenin reveal a shared evolutionary origin for pore-forming proteins and its mode of sphingomyelin recognition. Structure. Sep. 5, 2012;20(9):1498-507. doi:10.1016/j.str.2012.06.011. Epub Jul. 19, 2012.
Devereux et al., A comprehensive set of sequence analysis programs for the VAX. Nucleic Acids Res. Jan. 11, 1984;12(1 Pt 1):387-95.
Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.
Grant et al., A facile method for attaching nitroxide spin labels at the 5' terminus of nucleic acids. Nucleic Acids Res. 2007;35(10):e77. Epub May. 21, 2007.
Henikoff et al., Amino acid substitution matrices from protein blocks. Proc Natl Acad Sci U S A. Nov. 15, 1992;89(22):10915-9.
Ide et al., Lysenin forms a voltage-dependent channel in artificial lipid bilayer membranes. Biochem Biophys Res Commun Jul. 21, 2006;346(1):288-92. Epub May 26, 2006.
Ivanov et al., DNA tunneling detector embedded in a nanopore. Nano Lett. Jan. 12, 2011;11(1):279-85. doi: 10.1021/nl103873a. Epub Dec. 6, 2010.

Karlin et al., Applications and statistics for multiple high-scoring segments in molecular sequences. Proc Natl Acad Sci U S A. Jun. 15, 1993;90(12):5873-7.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Lazar et al., Transforming growth factor alpha: mutation of aspartic acid 47 and leucine 48 results in different biological activities. Mol Cell Biol. Mar. 1988;8(3):1247-52.
Liu et al., Adding new chemistries to the genetic code. Annu Rev Biochem. 2010;79:413-44. doi: 10.1146/annurev.biochem.052308.105824.
Montal et al., Formation of bimolecular membranes from lipid monolayers and a study of their electrical properties. Proc Natl Acad Sci U S A. Dec. 1972;69(12):3561-6.
Nikolov et al., Behavior of giant vesicles with anchored DNA molecules. Biophys J. Jun. 15, 2007;92(12):4356-68. Epub Mar. 23, 2007.
Pfeiffer et al., Bivalent cholesterol-based coupling of oligonucleotides to lipid membrane assemblies. J Am Chem Soc. Aug. 25, 2004;126(33):10224-5.
Skocaj et al., The sensing of membrane microdomains based on pore-forming toxins. Curr Med Chem. 2013;20(4):491-501.
Soni et al., Synchronous optical and electrical detection of biomolecules traversing through solid-state nanopores. Rev Sci Instrum. Jan. 2010;81(1):014301. doi: 10.1063/1.3277116.
Troutt et al., Ligation-anchored PCR: a simple amplification technique with single-sided specificity. Proc Natl Acad Sci U S A. Oct. 15 1992;89(20):9823-5. Erratum in: Proc Natl Acad Sci U S A Apr. 15, 1993;90(8):3775.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Yamaji et al., Lysenin, a novel sphingomyelin-specific binding protein. J Biol Chem. Feb. 27, 1998;273(9):5300-6.
Yoshina-Ishii et al., Arrays of mobile tethered vesicles on supported lipid bilayers. J Am Chem Soc. Apr. 2, 2003;125(13):3696-7.

* cited by examiner

SEQUENCE LISTING

<160> NUMBER OF SEQ ID NOS: 33

<210> SEQ ID NO 1
<211> LENGTH: 558
<212> TYPE: DNA
<213> ORGANISM: Artificial Sequence
<220> FEATURE:
<223> OTHER INFORMATION: NNN-RRK mutant MspA monomer

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial Sequence
<220> FEATURE:
<223> OTHER INFORMATION: Mature form of NNN-RRK mutant of the MspA monomer

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 1830
<212> TYPE: DNA
<213> ORGANISM: Bacillus subtilis phage Phi29

<400> SEQUENCE: 3

```
atgaaacaca tgccgcgtaa aatgtatagc tgcgcgtttg aaaccacgac caaagtggaa      60
gattgtcgcg tttgggccta tggctacatg aacatcgaag atcattctga atacaaaatc     120
ggtaacagtc tggatgaatt tatggcatgg gtgctgaaag ttcaggcgga tctgtacttc     180
cacaacctga atttgatgg cgcattcatt atcaactggc tggaacgtaa tggctttaaa     240
tggagcgcgg atggtctgcc gaacacgtat aataccatta tctctcgtat gggccagtgg     300
tatatgattg atatctgcct gggctacaaa ggtaaacgca aaattcatac cgtgatctat     360
gatagcctga aaaaactgcc gtttccggtg aagaaaattg cgaaagattt caaactgacg     420
gttctgaaag cgatattga ttatcacaaa gaacgtccgg ttggttacaa aatcaccccg     480
gaagaatacg catacatcaa aaacgatatc cagatcatcg cagaagcgct gctgattcag     540
tttaaacagg gcctggatcg catgaccgcg ggcagtgata gcctgaaagg tttcaaagat     600
atcatcacga ccaaaaaatt caaaaaagtg ttcccgacgc tgagcctggg tctggataaa     660
gaagttcgtt atgcctaccg cggcggtttt acctggctga cgatcgtttt caaagaaaaa     720
gaaattggcg agggtatggt gtttgatgtt aatagtctgt atccggcaca gatgtacagc     780
cgcctgctgc cgtatggcga accgatcgtg ttcgagggta aatatgtttg ggatgaagat     840
tacccgctgc atattcagca catccgttgt gaatttgaac tgaaagaagg ctatattccg     900
accattcaga tcaaacgtag tcgcttctat aagggtaacg aatacctgaa aagctctggc     960
ggtgaaatcg cggatctgtg gctgagtaac gtggatctgg aactgatgaa agaacactac    1020
```

```
gatctgtaca acgttgaata catcagcggc ctgaaattta aagccacgac cggtctgttc    1080
aaagatttca tcgataaatg gacctacatc aaaacgacct ctgaaggcgc gattaaacag    1140
ctggccaaac tgatgctgaa cagcctgtat ggcaaattcg cctctaatcc ggatgtgacc    1200
ggtaaagttc gtacctgaa agaaaatggc gcactgggtt ttcgcctggg cgaagaagaa     1260
acgaaagatc cggtgtatac cccgatgggt gttttcatta cggcctgggc acgttacacg    1320
accatcaccg cggcccaggc atgctatgat cgcattatct actgtgatac cgattctatt    1380
catctgacgg gcaccgaaat cccggatgtg attaagata tcgttgatcc gaaaaaactg      1440
ggttattggg cccacgaaag tacgtttaaa cgtgcaaaat acctgcgcca gaaaacctac    1500
atccaggata tctacatgaa agaagtggat ggcaaactgg ttgaaggttc tccggatgat    1560
tacaccgata tcaaattcag tgtgaaatgc gccggcatga cggataaaat caaaaaagaa    1620
gtgaccttcg aaaacttcaa agttggtttc agccgcaaaa tgaaaccgaa accggtgcag    1680
gttccgggcg gtgtggttct ggtggatgat acgtttacca ttaaatctgg cggtagtgcg    1740
tggagccatc cgcagttcga aaaaggcggt ggctctggtg gcggttctgg cggtagtgcc    1800
tggagccacc cgcagtttga aaataataa                                      1830

<210> SEQ ID NO 4
<211> LENGTH: 608
<212> TYPE: PRT
<213> ORGANISM: Bacillus subtilis phage Phi29

<400> SEQUENCE: 4

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220
```

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
            245                 250                 255

Gln Met Tyr Ser Arg Leu Leu Pro Tyr Gly Glu Pro Ile Val Phe Glu
        260                 265                 270

Gly Lys Tyr Val Trp Asp Glu Asp Tyr Pro Leu His Ile Gln His Ile
    275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
        340                 345                 350

Phe Lys Ala Thr Thr Gly Leu Phe Lys Asp Phe Ile Asp Lys Trp Thr
    355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
        420                 425                 430

Ile Thr Ala Trp Ala Arg Tyr Thr Thr Ile Thr Ala Ala Gln Ala Cys
    435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
        500                 505                 510

Leu Val Glu Gly Ser Pro Asp Asp Tyr Thr Asp Ile Lys Phe Ser Val
    515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
            565                 570                 575

Gly Gly Ser Ala Trp Ser His Pro Gln Phe Glu Lys Gly Gly Gly Ser
        580                 585                 590

Gly Gly Gly Ser Gly Gly Ser Ala Trp Ser His Pro Gln Phe Glu Lys
    595                 600                 605

<210> SEQ ID NO 5
<211> LENGTH: 1390
<212> TYPE: DNA
<213> ORGANISM: Escherichia coli

<400> SEQUENCE: 5

```
atgatgaacg atggcaaaca gcagagcacc ttcctgtttc atgattatga aaccttcggt    60
acccatccgg ccctggatcg tccggcgcag tttgcggcca ttcgcaccga tagcgaattc   120
aatgtgattg gcgaaccgga agtgttttat tgcaaaccgg ccgatgatta tctgccgcag   180
ccgggtgcgg tgctgattac cggtattacc ccgcaggaag cgcgcgcgaa aggtgaaaac   240
gaagcggcgt ttgccgcgcg cattcatagc ctgtttaccg tgccgaaaac ctgcattctg   300
ggctataaca atgtgcgctt cgatgatgaa gttacccgta atatctttta tcgtaacttt   360
tatgatccgt atgcgtggag ctggcagcat gataacagcc gttgggatct gctggatgtg   420
atgcgcgcgt gctatgcgct cgcccggaa ggcattaatt ggccggaaaa cgatgatggc   480
ctgccgagct ttcgtctgga acatctgacc aaagccaacg gcattgaaca tagcaatgcc   540
catgatgcga tggccgatgt ttatgcgacc attgcgatgg cgaaactggt taaaacccgt   600
cagccgcgcc tgtttgatta tctgtttacc caccgtaaca aacacaaact gatggcgctg   660
attgatgttc cgcagatgaa accgctggtg catgtgagcg cgatgttggg cgcctggcgc   720
ggcaacacca gctgggtggc cccgctggcc tggcacccgg aaaatcgtaa cgccgtgatt   780
atggttgatc tggccggtga tattagcccg ctgctggaac tggatagcga tacccctgcgt   840
gaacgcctgt ataccgccaa aaccgatctg ggcgataatg ccgccgtgcc ggtgaaactg   900
gttcacatta caaatgcccc ggtgctggcc caggcgaaca ccctgcgccc ggaagatgcg   960
gatcgtctgg gtattaatcg ccagcattgt ctggataatc tgaaaatcct gcgtgaaaac  1020
ccgcaggtgc gtgaaaaagt ggtggcgatc ttcgcggaag cggaaccgtt cacccccgagc  1080
gataacgtgg atgcgcagct gtataacggc ttctttagcg atgccgatcg cgcggcgatg  1140
aaaatcgttc tggaaaccga accgcgcaat ctgccggcgc tggatattac ctttgttgat  1200
aaacgtattg aaaaactgct gtttaattat cgtgcgcgca attttccggg taccctggat  1260
tatgccgaac agcagcgttg gctggaacat cgtcgtcagg ttttcaccccc ggaatttctg  1320
cagggttatg cggatgaact gcagatgctg gttcagcagt atgccgatga taaagaaaaa  1380
gtggcgctgc                                                         1390
```

<210> SEQ ID NO 6
<211> LENGTH: 485
<212> TYPE: PRT
<213> ORGANISM: Escherichia coli

<400> SEQUENCE: 6

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp

```
                115                 120                 125
    Gln His Asp Asn Ser Arg Trp Asp Leu Leu Asp Val Met Arg Ala Cys
        130                 135                 140
    Tyr Ala Leu Arg Pro Glu Gly Ile Asn Trp Pro Glu Asn Asp Asp Gly
    145                 150                 155                 160
    Leu Pro Ser Phe Arg Leu Glu His Leu Thr Lys Ala Asn Gly Ile Glu
                    165                 170                 175
    His Ser Asn Ala His Asp Ala Met Ala Asp Val Tyr Ala Thr Ile Ala
                180                 185                 190
    Met Ala Lys Leu Val Lys Thr Arg Gln Pro Arg Leu Phe Asp Tyr Leu
                195                 200                 205
    Phe Thr His Arg Asn Lys His Lys Leu Met Ala Leu Ile Asp Val Pro
        210                 215                 220
    Gln Met Lys Pro Leu Val His Val Ser Gly Met Phe Gly Ala Trp Arg
    225                 230                 235                 240
    Gly Asn Thr Ser Trp Val Ala Pro Leu Ala Trp His Pro Glu Asn Arg
                    245                 250                 255
    Asn Ala Val Ile Met Val Asp Leu Ala Gly Asp Ile Ser Pro Leu Leu
                260                 265                 270
    Glu Leu Asp Ser Asp Thr Leu Arg Glu Arg Leu Tyr Thr Ala Lys Thr
                275                 280                 285
    Asp Leu Gly Asp Asn Ala Ala Val Pro Val Lys Leu Val His Ile Asn
        290                 295                 300
    Lys Cys Pro Val Leu Ala Gln Ala Asn Thr Leu Arg Pro Glu Asp Ala
    305                 310                 315                 320
    Asp Arg Leu Gly Ile Asn Arg Gln His Cys Leu Asp Asn Leu Lys Ile
                    325                 330                 335
    Leu Arg Glu Asn Pro Gln Val Arg Glu Lys Val Val Ala Ile Phe Ala
                340                 345                 350
    Glu Ala Glu Pro Phe Thr Pro Ser Asp Asn Val Asp Ala Gln Leu Tyr
                355                 360                 365
    Asn Gly Phe Phe Ser Asp Ala Asp Arg Ala Ala Met Lys Ile Val Leu
        370                 375                 380
    Glu Thr Glu Pro Arg Asn Leu Pro Ala Leu Asp Ile Thr Phe Val Asp
    385                 390                 395                 400
    Lys Arg Ile Glu Lys Leu Leu Phe Asn Tyr Arg Ala Arg Asn Phe Pro
                    405                 410                 415
    Gly Thr Leu Asp Tyr Ala Glu Gln Gln Arg Trp Leu Glu His Arg Arg
                420                 425                 430
    Gln Val Phe Thr Pro Glu Phe Leu Gln Gly Tyr Ala Asp Glu Leu Gln
                435                 440                 445
    Met Leu Val Gln Gln Tyr Ala Asp Lys Glu Lys Val Ala Leu Leu
        450                 455                 460
    Lys Ala Leu Trp Gln Tyr Ala Glu Glu Ile Val Ser Gly Ser Gly His
    465                 470                 475                 480
    His His His His His
                    485

<210> SEQ ID NO 7
<211> LENGTH: 804
<212> TYPE: DNA
<213> ORGANISM: Escherichia coli

<400> SEQUENCE: 7
```

```
atgaaatttg tctcttttaa tatcaacggc ctgcgcgcca gacctcacca gcttgaagcc    60
atcgtcgaaa agcaccaacc ggatgtgatt ggcctgcagg agacaaaagt tcatgacgat   120
atgtttccgc tcgaagaggt ggcgaagctc ggctacaacg tgttttatca cgggcagaaa   180
ggccattatg gcgtggcgct gctgaccaaa gagacgccga ttgccgtgcg tcgcggcttt   240
cccggtgacg acgaagaggc gcagcggcgg attattatgg cggaaatccc ctcactgctg   300
ggtaatgtca ccgtgatcaa cggttacttc ccgcagggtg aaagccgcga ccatccgata   360
aaattcccgg caaaagcgca gttttatcag aatctgcaaa actacctgga aaccgaactc   420
aaacgtgata tccggtact gattatgggc gatatgaata tcagccctac agatctggat   480
atcggcattg gcgaagaaaa ccgtaagcgc tggctgcgta ccggtaaatg ctctttcctg   540
ccggaagagc gcgaatggat ggacaggctg atgagctggg ggttggtcga taccttccgc   600
catgcgaatc cgcaaacagc agatcgtttc tcatggtttg attaccgctc aaaaggtttt   660
gacgataacc gtggtctgcg catcgacctg ctgctcgcca gccaaccgct ggcagaatgt   720
tgcgtagaaa ccggcatcga ctatgaaatc cgcagcatgg aaaaaccgtc cgatcacgcc   780
cccgtctggg cgaccttccg ccgc                                          804
```

<210> SEQ ID NO 8
<211> LENGTH: 268
<212> TYPE: PRT
<213> ORGANISM: Escherichia coli

<400> SEQUENCE: 8

```
Met Lys Phe Val Ser Phe Asn Ile Asn Gly Leu Arg Ala Arg Pro His
1               5                   10                  15
Gln Leu Glu Ala Ile Val Glu Lys His Gln Pro Asp Val Ile Gly Leu
                20                  25                  30
Gln Glu Thr Lys Val His Asp Asp Met Phe Pro Leu Glu Glu Val Ala
            35                  40                  45
Lys Leu Gly Tyr Asn Val Phe Tyr His Gly Gln Lys Gly His Tyr Gly
        50                  55                  60
Val Ala Leu Leu Thr Lys Glu Thr Pro Ile Ala Val Arg Arg Gly Phe
65                  70                  75                  80
Pro Gly Asp Asp Glu Glu Ala Gln Arg Arg Ile Ile Met Ala Glu Ile
                85                  90                  95
Pro Ser Leu Leu Gly Asn Val Thr Val Ile Asn Gly Tyr Phe Pro Gln
            100                 105                 110
Gly Glu Ser Arg Asp His Pro Ile Lys Phe Pro Ala Lys Ala Gln Phe
        115                 120                 125
Tyr Gln Asn Leu Gln Asn Tyr Leu Glu Thr Glu Leu Lys Arg Asp Asn
    130                 135                 140
Pro Val Leu Ile Met Gly Asp Met Asn Ile Ser Pro Thr Asp Leu Asp
145                 150                 155                 160
Ile Gly Ile Gly Glu Glu Asn Arg Lys Arg Trp Leu Arg Thr Gly Lys
                165                 170                 175
Cys Ser Phe Leu Pro Glu Glu Arg Glu Trp Met Asp Arg Leu Met Ser
            180                 185                 190
Trp Gly Leu Val Asp Thr Phe Arg His Ala Asn Pro Gln Thr Ala Asp
        195                 200                 205
Arg Phe Ser Trp Phe Asp Tyr Arg Ser Lys Gly Phe Asp Asp Asn Arg
    210                 215                 220
Gly Leu Arg Ile Asp Leu Leu Leu Ala Ser Gln Pro Leu Ala Glu Cys
```

```
                225                 230                 235                 240
            Cys Val Glu Thr Gly Ile Asp Tyr Glu Ile Arg Ser Met Glu Lys Pro
                                245                 250                 255

Ser Asp His Ala Pro Val Trp Ala Thr Phe Arg Arg
                            260                 265

<210> SEQ ID NO 9
<211> LENGTH: 1275
<212> TYPE: DNA
<213> ORGANISM: Thermus thermophilus

<400> SEQUENCE: 9
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac     120 ggcgactatg atgcggatgg cctgaccggc accgcgatcc tggttcgtgg tctggccgcc    180
ctgggtgcgg atgttcatcc gtttatcccg caccgcctgg aagaaggcta tggtgtcctg    240
atggaacgcg tcccggaaca tctggaagcc tcggacctgt ttctgaccgt tgactgcggc    300
attaccaacc atgcggaact gcgcgaactg ctggaaaatg cgtggaagt cattgttacc     360 gatcatcata cgccgggcaa aacgccgccg ccgggtctgg tcgtgcatcc ggcgctgacg    420
ccggatctga agaaaaaacc gaccggcgca ggcgtggcgt ttctgctgct gtgggcactg    480
catgaacgcc tgggcctgcc gccgccgctg gaatacgcgg acctggcagc cgttggcacc    540
attgccgacg ttgccccgct gtggggttgg aatcgtgcac tggtgaaaga aggtctggca    600
cgcatcccgg cttcatcttg ggtgggcctg cgtctgctgg ctgaagccgt gggctatacc    660
ggcaaagcgg tcgaagtcgc tttccgcatc gcgccgcgca tcaatgcggc ttcccgcctg    720
ggcgaagcgg aaaaagccct gcgcctgctg ctgacggatg atgcggcaga agctcaggcg    780
ctggtcggcg aactgcaccg tctgaacgcc cgtcgtcaga ccctggaaga agcgatgctg    840
cgcaaactgc tgccgcaggc cgacccggaa gcgaaagcca tcgttctgct ggacccggaa    900
ggccatccgg tgttatggg tattgtggcc tctcgcatcc tggaagcgac cctgcgcccg    960
gtctttctgg tggcccaggg caaaggcacc gtgcgttcgc tggctccgat tccgccgtc   1020 gaagcactgc gcagcgcgga agatctgctg ctgcgttatg gtggtcataa agaagcggcg   1080
ggtttcgcaa tggatgaagc gctgtttccg gcgttcaaag cacgcgttga gcgtatgcc    1140 gcacgtttcc cggatccggt tcgtgaagtg gcactgctgg atctgctgcc ggaaccgggc   1200
ctgctgccgc aggtgttccg tgaactggca ctgctggaac cgtatggtga aggtaacccg   1260
gaaccgctgt tcctg                                                     1275

<210> SEQ ID NO 10
<211> LENGTH: 425
<212> TYPE: PRT
<213> ORGANISM: Thermus thermophilus

<400> SEQUENCE: 10

Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
                20                  25                  30

Gln Gly Lys Arg Ile Arg Val His Gly Asp Tyr Asp Ala Asp Gly Leu
            35                  40                  45

Thr Gly Thr Ala Ile Leu Val Arg Gly Leu Ala Ala Leu Gly Ala Asp
        50                  55                  60
```

Val His Pro Phe Ile Pro His Arg Leu Glu Glu Gly Tyr Gly Val Leu
 65                  70                  75                  80

Met Glu Arg Val Pro Glu His Leu Glu Ala Ser Asp Leu Phe Leu Thr
                 85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 11
<211> LENGTH: 738
<212> TYPE: DNA
<213> ORGANISM: Bacteriophage lambda

<400> SEQUENCE: 11
tccggaagcg gctctggtag tggttctggc atgacaccgg acattatcct gcagcgtacc      60

-continued

```
gggatcgatg tgagagctgt cgaacagggg gatgatgcgt ggcacaaatt acggctcggc      120
gtcatcaccg cttcagaagt tcacaacgtg atagcaaaac cccgctccgg aaagaagtgg      180
cctgacatga aaatgtccta cttccacacc ctgcttgctg aggtttgcac cggtgtggct      240
ccggaagtta acgctaaagc actggcctgg ggaaaacagt acgagaacga cgccagaacc      300
ctgtttgaat tcacttccgg cgtgaatgtt actgaatccc cgatcatcta tcgcgacgaa      360
agtatgcgta ccgcctgctc tcccgatggt ttatgcagtg acggcaacgg ccttgaactg      420
aaatgcccgt ttacctcccg ggatttcatg aagttccggc tcggtggttt cgaggccata      480
aagtcagctt acatggccca ggtgcagtac agcatgtggg tgacgcgaaa aaatgcctgg      540
tactttgcca actatgaccc gcgtatgaag cgtgaaggcc tgcattatgt cgtgattgag      600
cgggatgaaa agtacatggc gagttttgac gagatcgtgc cggagttcat cgaaaaaatg      660
gacgaggcac tggctgaaat tggttttgta tttggggagc aatggcgatc tggctctggt      720
tccggcagcg gttccgga                                                   738
```

<210> SEQ ID NO 12
<211> LENGTH: 226
<212> TYPE: PRT
<213> ORGANISM: Bacteriophage lambda

<400> SEQUENCE: 12

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

```
<210> SEQ ID NO 13
<211> LENGTH: 134
<212> TYPE: DNA
<213> ORGANISM: Artificial Sequence
<220> FEATURE:
<223> OTHER INFORMATION: Sequence used in Example 2

<400> SEQUENCE: 13
cccccccccc cccccccccc cccccccccc cacccccccc cccccccccc cctaaagcta     60
catcgtcaac gttatatttt gatagtttga cggttaatgc tggtaatggt ggttttcttc    120
aaaatttgtt agcc                                                      134

<210> SEQ ID NO 14
<211> LENGTH: 84
<212> TYPE: DNA
<213> ORGANISM: Artificial Sequence
<220> FEATURE:
<223> OTHER INFORMATION: Sequence used in Example 2

<400> SEQUENCE: 14
ggctaacaaa ttttgaagaa aaccaccatt accagcatta accgtcaaac tatcaaaata     60
taacgttgac gatgtagctt tagg                                            84

<210> SEQ ID NO 15
<211> LENGTH: 100
<212> TYPE: DNA
<213> ORGANISM: Artificial Sequence
<220> FEATURE:
<223> OTHER INFORMATION: Sequence used in Example 2

<400> SEQUENCE: 15
cccccccccc ccccccaccc cccccccccc ccccctattc tgtttatgtt tcttgtttgt     60
tagccttttg gctaacaaac aagaaacata aacagaatag                          100

<210> SEQ ID NO 16
<211> LENGTH: 184
<212> TYPE: PRT
<213> ORGANISM: Mycobacterium smegmatis

<400> SEQUENCE: 16

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
```

```
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 17
<211> LENGTH: 184
<212> TYPE: PRT
<213> ORGANISM: Mycobacterium smegmatis

<400> SEQUENCE: 17

```
Gly Leu Asp Asn Glu Leu Ser Leu Val Asp Gly Gln Asp Arg Thr Leu
1               5                   10                  15
Thr Val Gln Gln Trp Asp Thr Phe Leu Asn Gly Val Phe Pro Leu Asp
                20                  25                  30
Arg Asn Arg Leu Thr Arg Glu Trp Phe His Ser Gly Arg Ala Lys Tyr
            35                  40                  45
Ile Val Ala Gly Pro Gly Ala Asp Glu Phe Glu Gly Thr Leu Glu Leu
        50                  55                  60
Gly Tyr Gln Ile Gly Phe Pro Trp Ser Leu Gly Val Gly Ile Asn Phe
65                  70                  75                  80
Ser Tyr Thr Thr Pro Asn Ile Leu Ile Asp Asp Gly Asp Ile Thr Gly
                85                  90                  95
Pro Pro Phe Gly Leu Glu Ser Val Ile Thr Pro Asn Leu Phe Pro Gly
                100                 105                 110
Val Ser Ile Ser Ala Asp Leu Gly Asn Gly Pro Gly Ile Gln Glu Val
            115                 120                 125
Ala Thr Phe Ser Val Asp Val Ser Gly Pro Ala Gly Gly Val Ala Val
        130                 135                 140
Ser Asn Ala His Gly Thr Val Thr Gly Ala Ala Gly Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 18
<211> LENGTH: 183
<212> TYPE: PRT
<213> ORGANISM: Mycobacterium smegmatis

<400> SEQUENCE: 18

```
Val Asp Asn Gln Leu Ser Val Val Asp Gly Gln Gly Arg Thr Leu Thr
1               5                   10                  15
Val Gln Gln Ala Glu Thr Phe Leu Asn Gly Val Phe Pro Leu Asp Arg
                20                  25                  30
Asn Arg Leu Thr Arg Glu Trp Phe His Ser Gly Arg Ala Thr Tyr His
            35                  40                  45
Val Ala Gly Pro Gly Ala Asp Glu Phe Glu Gly Thr Leu Glu Leu Gly
        50                  55                  60
Tyr Gln Val Gly Phe Pro Trp Ser Leu Gly Val Gly Ile Asn Phe Ser
65                  70                  75                  80
Tyr Thr Thr Pro Asn Ile Leu Ile Asp Gly Gly Asp Ile Thr Gln Pro
                85                  90                  95
Pro Phe Gly Leu Asp Thr Ile Ile Thr Pro Asn Leu Phe Pro Gly Val
```

```
                    100                 105                 110
Ser Ile Ser Ala Asp Leu Gly Asn Gly Pro Gly Ile Gln Glu Val Ala
            115                 120                 125

Thr Phe Ser Val Asp Val Lys Gly Ala Lys Gly Ala Val Ala Val Ser
        130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 19
<211> LENGTH: 454
<212> TYPE: DNA
<213> ORGANISM: Artificial Sequence
<220> FEATURE:
<223> OTHER INFORMATION: Sequence used in the Examples
<220> FEATURE:
<221> NAME/KEY: modified_base
<222> LOCATION: (1)..(4)
<223> OTHER INFORMATION: 2'-O-Methyl-Uracil

<400> SEQUENCE: 19 nnnnttttt  tttttttttt  tttttttttt  tttttttttt  tttttttttt  ttttggttgt      60
ttctgttggt  gctgatattg  cttttgatgc  cgaccctaaa  ttttttgcct  gtttggttcg     120
ctttgagtct  tcttcggttc  cgactaccct  cccgactgcc  tatgatgttt  atccttgaa     180 tggtcgccat  gatggtggtt  attataccgt  caaggactgt  gtgactattg  acgtccttcc    240
ccgtacgccg  ggcaataacg  tttatgttgg  tttcatggtt  tggtctaact  ttaccgctac    300
taaatgccgc  ggattggttt  cgctgaatca  ggttattaaa  gagattattt  gtctccagcc    360
acttaagtga  ggtgatttat  gtttggtgct  attgctggcg  gtattgcttc  tgctcttgct    420
ggtggcgcca  tgtctaaatt  gtttggaggc  ggtc                                  454

<210> SEQ ID NO 20
<211> LENGTH: 57
<212> TYPE: DNA
<213> ORGANISM: Artificial Sequence
<220> FEATURE:
<223> OTHER INFORMATION: Sequence used in the Examples

<400> SEQUENCE: 20
gcaatatcag  caccaacaga  aacaaccttt  tttttttttt  tttttttttt  ttttttt        57

<210> SEQ ID NO 21
<211> LENGTH: 139
<212> TYPE: DNA
<213> ORGANISM: Artificial Sequence
<220> FEATURE:
<223> OTHER INFORMATION: Sequence used in the Examples

<400> SEQUENCE: 21 ttttttttt  tttttttttt  tccccccccc  cccctattc  tgtttatgtt  tcttgtttgt       60 tagcccccctt  tgataagaca  aatacaaaga  acaaacaatc  ggccctttag  tggagcgagt   120
gcgagaggcg  agcggtcaa                                                     139

<210> SEQ ID NO 22
<211> LENGTH: 120
<212> TYPE: DNA
```

```
<213> ORGANISM: Artificial Sequence
<220> FEATURE:
<223> OTHER INFORMATION: Sequence used in the Examples

<400> SEQUENCE: 22
gtatctccat cgctgttgac cgctcgcctc tcgcactcgc tccactaaag ggccgattgt    60
ttgttctttg tatttgtctt atcaaagggg gctaacaaac aagaaacata aacagaatag   120

<210> SEQ ID NO 23
<211> LENGTH: 15
<212> TYPE: DNA
<213> ORGANISM: Artificial Sequence
<220> FEATURE:
<223> OTHER INFORMATION: Sequence used in the Examples

<400> SEQUENCE: 23
cagcgatgga gatac                                                     15

<210> SEQ ID NO 24
<211> LENGTH: 60
<212> TYPE: DNA
<213> ORGANISM: Artificial Sequence
<220> FEATURE:
<223> OTHER INFORMATION: Sequence used in the Examples

<400> SEQUENCE: 24
cccccccccc ccccccaccccc cccccccccc ccccuauuc uguuuauguu ucuuguuugu    60

<210> SEQ ID NO 25
<211> LENGTH: 60
<212> TYPE: DNA
<213> ORGANISM: Artificial Sequence
<220> FEATURE:
<223> OTHER INFORMATION: Sequence used in the Examples

<400> SEQUENCE: 25
uauucuguuu auguuucuug uuuguuagcc cccuugaua agacaaauac aaagaacaaa     60

<210> SEQ ID NO 26
<211> LENGTH: 44
<212> TYPE: DNA
<213> ORGANISM: Artificial Sequence
<220> FEATURE:
<223> OTHER INFORMATION: Sequence used in the Examples

<400> SEQUENCE: 26
agaaacataa acagaataac aaacaagaaa cataaacaga atag                     44

<210> SEQ ID NO 27
<211> LENGTH: 120
<212> TYPE: DNA
<213> ORGANISM: Artificial Sequence
<220> FEATURE:
<223> OTHER INFORMATION: Sequence used in the Examples

<400> SEQUENCE: 27
cccccccccc ccccccaccccc cccccccccc ccccuauuc uguuuauguu ucuuguuugu    60
uauucuguuu auguuucuug uuuguuagcc cccuugaua agacaaauac aaagaacaaa    120

<210> SEQ ID NO 28
<211> LENGTH: 1176
<212> TYPE: DNA
<213> ORGANISM: Artificial Sequence
<220> FEATURE:
<223> OTHER INFORMATION: Dimer of NNN-RRK in Example 14
```

<400> SEQUENCE: 28

```
atgggtctgg ataatgaact gagcctggtg gacggtcaag atcgtaccct gacggtgcaa      60
caatgggata ccttttctgaa tggcgttttt ccgctggatc gtaatcgcct gacccgtgaa    120
tggtttcatt ccggtcgcgc aaaatatatc gtcgcaggcc cgggtgctga cgaattcgaa    180
ggcacgctgg aactgggtta tcagattggc tttccgtggt cactgggcgt tggtatcaac    240
ttctcgtaca ccacgccgaa tattctgatc aacaatggta acattaccgc accgccgttt    300
ggcctgaaca gcgtgattac gccgaacctg tttccgggtg ttagcatctc tgcccgtctg    360
ggcaatggtc cgggcattca agaagtggca acctttagtg tgcgcgtttc cggcgctaaa    420
ggcggtgtcg cggtgtctaa cgcccacggt accgttacgg gcgcggccgg cggtgtcctg    480
ctgcgtccgt tcgcgcgcct gattgcctct accggcgaca cgttacgac ctatggcgaa    540
ccgtggaata tgaactcggg ttcaggatcc ggagatgacg atgatgacga cgatgactcc    600
ggatcgggtt cttccatggg tctggataat gaactgagcc tggtgacgg tcaagatcgt    660
accctgacgg tgcaacaatg ggatacccttt ctgaatggcg ttttccgct ggatcgtaat    720
cgcctgaccc gtgaatggtt tcattccggt cgcgcaaaat atatcgtcgc aggcccgggt    780
gctgacgaat tcgaaggcac gctggaactg ggttatcaga ttggctttcc gtggtcactg    840
ggcgttggta tcaacttctc gtacaccacg ccgaatattc tgatcaacaa tggtaacatt    900
accgcaccgc cgtttggcct gaacagcgtg attacgccga acctgtttcc gggtgttagc    960
atctctgccc gtctgggcaa tggtccgggc attcaagaag tggcaacctt tagtgtgcgc   1020
gtttccggcg ctaaaggcgg tgtcgcggtg tctaacgccc acggtaccgt tacgggcgcg   1080
gccggcggtg tcctgctgcg tccgttcgcg cgcctgattg cctctaccgg cgacagcgtt   1140
acgacctatg gcgaaccgtg gaatatgaac taatag                               1176
```

<210> SEQ ID NO 29
<211> LENGTH: 390
<212> TYPE: PRT
<213> ORGANISM: Artificial Sequence
<220> FEATURE:
<223> OTHER INFORMATION: Dimer of NNN-RRK used in Example 14

<400> SEQUENCE: 29

```
Met Gly Leu Asp Asn Glu Leu Ser Leu Val Asp Gly Gln Asp Arg Thr
  1               5                  10                  15

Leu Thr Val Gln Gln Trp Asp Thr Phe Leu Asn Gly Val Phe Pro Leu
             20                  25                  30

Asp Arg Asn Arg Leu Thr Arg Glu Trp Phe His Ser Gly Arg Ala Lys
         35                  40                  45

Tyr Ile Val Ala Gly Pro Gly Ala Asp Glu Phe Glu Gly Thr Leu Glu
     50                  55                  60

Leu Gly Tyr Gln Ile Gly Phe Pro Trp Ser Leu Gly Val Gly Ile Asn
 65                  70                  75                  80

Phe Ser Tyr Thr Thr Pro Asn Ile Leu Ile Asn Asn Gly Asn Ile Thr
                 85                  90                  95

Ala Pro Pro Phe Gly Leu Asn Ser Val Ile Thr Pro Asn Leu Phe Pro
            100                 105                 110

Gly Val Ser Ile Ser Ala Arg Leu Gly Asn Gly Pro Gly Ile Gln Glu
        115                 120                 125

Val Ala Thr Phe Ser Val Arg Val Ser Gly Ala Lys Gly Gly Val Ala
    130                 135                 140
```

```
Val Ser Asn Ala His Gly Thr Val Thr Gly Ala Ala Gly Gly Val Leu
145                 150                 155                 160

Leu Arg Pro Phe Ala Arg Leu Ile Ala Ser Thr Gly Asp Ser Val Thr
            165                 170                 175

Thr Tyr Gly Glu Pro Trp Asn Met Asn Ser Gly Ser Gly Ser Gly Asp
        180                 185                 190

Asp Asp Asp Asp Asp Asp Ser Gly Ser Gly Ser Ser Met Gly Leu
        195                 200                 205

Asp Asn Glu Leu Ser Leu Val Asp Gly Gln Asp Arg Thr Leu Thr Val
210                 215                 220

Gln Gln Trp Asp Thr Phe Leu Asn Gly Val Phe Pro Leu Asp Arg Asn
225                 230                 235                 240

Arg Leu Thr Arg Glu Trp Phe His Ser Gly Arg Ala Lys Tyr Ile Val
            245                 250                 255

Ala Gly Pro Gly Ala Asp Glu Phe Glu Gly Thr Leu Glu Leu Gly Tyr
        260                 265                 270

Gln Ile Gly Phe Pro Trp Ser Leu Gly Val Gly Ile Asn Phe Ser Tyr
        275                 280                 285

Thr Thr Pro Asn Ile Leu Ile Asn Asn Gly Asn Ile Thr Ala Pro Pro
290                 295                 300

Phe Gly Leu Asn Ser Val Ile Thr Pro Asn Leu Phe Pro Gly Val Ser
305                 310                 315                 320

Ile Ser Ala Arg Leu Gly Asn Gly Pro Gly Ile Gln Glu Val Ala Thr
            325                 330                 335

Phe Ser Val Arg Val Ser Gly Ala Lys Gly Gly Val Ala Val Ser Asn
        340                 345                 350

Ala His Gly Thr Val Thr Gly Ala Ala Gly Gly Val Leu Leu Arg Pro
        355                 360                 365

Phe Ala Arg Leu Ile Ala Ser Thr Gly Asp Ser Val Thr Thr Tyr Gly
        370                 375                 380

Glu Pro Trp Asn Met Asn
385                 390

<210> SEQ ID NO 30
<211> LENGTH: 81
<212> TYPE: DNA
<213> ORGANISM: Artificial Sequence
<220> FEATURE:
<223> OTHER INFORMATION: Sequence used in Example 16
<220> FEATURE:
<221> NAME/KEY: modified_base
<222> LOCATION: (9)..(9)
<223> OTHER INFORMATION: 5-methylcytosine
<220> FEATURE:
<221> NAME/KEY: modified_base
<222> LOCATION: (27)..(27)
<223> OTHER INFORMATION: 5-methylcytosine

<400> SEQUENCE: 30 tttttttnt tttttttctt tttttngtt tttttcgtt tttttgtat ctccatcgct    60 gccccctttt tccccctttt t                                          81

<210> SEQ ID NO 31
<211> LENGTH: 34
<212> TYPE: DNA
<213> ORGANISM: Artificial Sequence
<220> FEATURE:
<223> OTHER INFORMATION: Sequence used in Example 16
```

```
<400> SEQUENCE: 31
ggcagcgatg gagatacttg aggcgagcgg tcaa                                34

<210> SEQ ID NO 32
<211> LENGTH: 15
<212> TYPE: DNA
<213> ORGANISM: Artificial Sequence
<220> FEATURE:
<223> OTHER INFORMATION: Sequence used in Example 16

<400> SEQUENCE: 32
ttgaccgctc gcctc                                                     15

<210> SEQ ID NO 33
<211> LENGTH: 20
<212> TYPE: PRT
<213> ORGANISM: Artificial Sequence
<220> FEATURE:
<223> OTHER INFORMATION: Sequence used in the Examples

<400> SEQUENCE: 33

Ser Gly Ser Gly Ser Gly Asp Asp Asp Asp Asp Asp Asp Ser Gly
1               5                   10                  15

Ser Gly Ser Ser
            20
```

MUTANT PORES

RELATED APPLICATIONS

This Application is a national stage filing under U.S.C. §371 of PCT International Application PCT/GB2012/050301, with an international filing date of Feb. 10, 2012, which claims the benefit under 35 U.S.C. §119(e) to U.S. Provisional Application No. 61/441,718, filed on Feb. 11, 2011, the contents of each of which are herein incorporated by reference in their entireties.

FIELD OF THE INVENTION

The invention relates to mutant forms of Msp. The invention also relates to nucleic acid characterisation using Msp.

BACKGROUND OF THE INVENTION

Nanopore sensing is an approach to sensing that relies on the observation of individual binding events between analyte molecules and a receptor. Nanopore sensors can be created by placing a single pore of nanometer dimensions in an insulating membrane and measuring voltage-driven ionic transport through the pore in the presence of analyte molecules. The identity of an analyte is revealed through its distinctive current signature, notably the duration and extent of current block and the variance of current levels.

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required.

Two of the essential components of sequencing nucleic acids using nanopore sensing are (1) the control of nucleic acid movement through the pore and (2) the discrimination of nucleotides as the nucleic acid polymer is moved through the pore. In the past, to achieve nucleotide discrimination the nucleic acid has been passed through a mutant of hemolysin. This has provided current signatures that have been shown to be sequence dependent. It has also been shown that a large number of nucleotides contribute to the observed current, making a direct relationship between observed current and nucleic acid sequence challenging.

While the current range for nucleotide discrimination has been improved through mutation of the hemolysin pore, a sequencing system would have higher performance if the current differences between nucleotides could be improved further. In addition, it has been observed that when the nucleic acids are moved through a pore, some current states show high variance. It has also been shown that some mutant hemolysin pores exhibit higher variance than others. While the variance of these states may contain sequence specific information, it is desirable to produce pores that have low variance to simplify the system. It is also desirable to reduce the number of nucleotides that contribute to the observed current.

The different forms of Msp are porins from *Mycobacterium smegmatis*. MspA is a 157 kDa octameric porin from *Mycobacterium smegmatis*. The structure of MspA has been well documented by researchers (Gundlach, Proc Natl Acad Sci USA. 2010 Sep. 14; 107(37):16060-5. Epub 2010 Aug. 26). Some key residues have been identified and modified to enhance the properties of the pore. These mutations have been performed to allow DNA to transition through the MspA pore. MspB, C and D are also known forms of Msp.

SUMMARY OF THE INVENTION

The inventors have surprisingly demonstrated that novel mutants of Msp display improved properties for estimating the characteristics, such as the sequence of nucleic acids. The mutants surprisingly display improved nucleotide discrimination. In particular, the mutants surprisingly display an increased current range, which makes it easier to discriminate between different nucleotides, and a reduced variance of states, which increases the signal-to-noise ratio. In addition, the number of nucleotides contributing to the current as the nucleic acid moves through the pore is decreased. This makes it easier to identify a direct relationship between the observed current as the nucleic acid moves through the pore and the nucleic acid sequence.

The inventors have also surprisingly shown that Msp shows improved sequencing properties when the movement of the nucleic acid through the pore is controlled by a Phi29 DNA polymerase. In particular, the coupling of Msp and Phi29 DNA polymerase results in three unexpected advantages. First, the nucleic acid moves through the pore at a rate that is commercially viable yet allows effective sequencing. Second, an increased current range is observed as the nucleic acid moves through the pore allowing the sequence to be determined more easily. Third, a decreased current variance is observed thereby increasing the signal-to-noise ratio.

Accordingly, the invention provides a mutant Msp monomer comprising a variant of the sequence shown in SEQ ID NO: 2, wherein the variant comprises at least one of the following mutations:
  (a) asparagine (N), serine (S), glutamine (Q) or threonine (T) at position 88;
  (b) serine (S), glutamine (Q) or tyrosine (Y) at position 90;
  (c) leucine (L) or serine (S) at position 105;
  (d) arginine (R) at position 126;
  (e) serine (S) at position 75;
  (f) serine (S) at position 77;
  (g) arginine (R) at position 59;
  (h) glutamine (Q), asparagine (N) or threonine (T) at position 75;
  (i) glutamine (Q), asparagine (N) or threonine (T) at position 77;
  (j) leucine (L) at position 78;
  (k) asparagine (N) at position 81;
  (l) asparagine (N) at position 83;
  (m) serine (S) or threonine (T) at position 86;
  (n) phenylalanine (F), valine (V) or leucine (L) at position 87;
  (o) tyrosine (Y), phenylalanine (F), valine (V), arginine (R), alanine (A), glycine (G) or cysteine (C) at position 88;
  (p) phenylalanine (F), valine (V) or leucine (L) at position 89;
  (q) leucine (L), phenylalanine (F), tryptophan (W), histidine (H), threonine (T), glycine (G), alanine (A), valine (V), arginine (R), lysine (K), asparagine (N) or cysteine (C) at position 90;
  (r) serine (S), glutamine (Q), leucine (L), methionine (M), isoleucine (I), alanine (A), valine (V), glycine (G), phenylalanine (F), tryptophan (W), tyrosine (Y), histidine (H), threonine (T), arginine (R), lysine (K), asparagine (N) or cysteine (C) at position 91;
(s) alanine (A) or serine (S) at position 92;
(t) serine (S), alanine (A), threonine (T), glycine (G) at position 93;
(u) leucine (L) at position 94;
(v) valine (V) at position 95;
(w) arginine (R), aspartic acid (D), valine (V), asparagine (N), serine (S) or threonine (T) at position 96;
(x) serine (S) at position 97;
(y) serine (S) at position 98;
(z) serine (S) at position 99;
(aa) serine (S) at position 100;
(bb) phenylalanine (F) at position 101;
(cc) lysine (K), serine (S) or threonine (T) at position 102;
(dd) alanine (A), glutamine (Q), asparagine (N), glycine (G) or threonine (T) at position 103;
(ee) isoleucine at position 104;
(ff) tyrosine (Y), alanine (A), glutamine (Q), asparagine (N), threonine (T), phenylalanine (F), tryptophan (W), histidine (H), glycine (G), valine (V), arginine (R), lysine (K), proline (P), or cysteine (C) at position 105;
(gg) phenylalanine (F), isoleucine (I), valine (V) or serine (S) at position 106;
(hh) proline (P) or serine (S) at position 108;
(ii) asparagine (N) at position 118;
(jj) serine (S) or cysteine (C) at position 103; and
(kk) cysteine at one or more of positions 10 to 15, 51 to 60, 136 to 139 and 168 to 172.

The invention also provides:
a construct comprising two or more covalently attached monomers derived from Msp;
a polynucleotide which encodes a mutant of the invention or a construct of the invention;
a homo-oligomeric pore derived from Msp comprising identical mutant monomers of the invention;
a hetero-oligomeric pore derived from Msp comprising at least one mutant monomer of the invention, wherein at least one of the eight monomers differs from the others;
a method of characterising a target nucleic acid sequence, comprising:
(a) contacting the target sequence with a pore of the invention and a nucleic acid binding protein so that the protein controls the movement of the target sequence through the pore and a proportion of the nucleotides in the target sequence interacts with the pore; and
(b) measuring the current passing through the pore during each interaction and thereby characterising the target sequence;
a kit for sequencing a target nucleic acid sequence comprising (a) a pore of the invention and (b) a nucleic acid handling enzyme;
an apparatus for sequencing target nucleic acid sequences in a sample, comprising (a) a plurality of pores of the invention and (b) a plurality of nucleic acid handling enzymes;
a method of characterising a target nucleic acid sequence, comprising:
(a) contacting the target sequence with a pore derived from Msp and a Phi29 DNA polymerase such that the polymerase controls the movement of the target sequence through the pore and a proportion of the nucleotides in the target sequence interacts with the pore; and
(b) measuring the current passing through the pore during each interaction and thereby characterising the target sequence, wherein steps (a) and (b) are carried out with a voltage applied across the pore;
a method of forming a sensor for characterising a target nucleic acid sequence, comprising:
(a) contacting a pore derived from Msp with a Phi29 DNA polymerase in the presence of the target nucleic acid sequence; and
(b) applying a voltage across the pore to form a complex between the pore and the polymerase; and thereby forming a sensor for characterising the target nucleic acid sequence;
a method of increasing the rate of activity of a Phi29 DNA polymerase, comprising:
(a) contacting the Phi29 DNA polymerase with a pore derived from Msp in the presence of a nucleic acid sequence; and
(b) applying a voltage across the pore to form a complex between the pore and the polymerase; and thereby increasing the rate of activity of a Phi29 DNA polymerase;
a kit for characterising a target nucleic acid sequence comprising (a) a pore derived from Msp and (b) a Phi29 DNA polymerase; and
an apparatus for characterising target nucleic acid sequences in a sample, comprising a plurality of pores derived from Msp and a plurality of Phi29 DNA polymerases.

DESCRIPTION OF THE SEQUENCE LISTING

Figure 1:
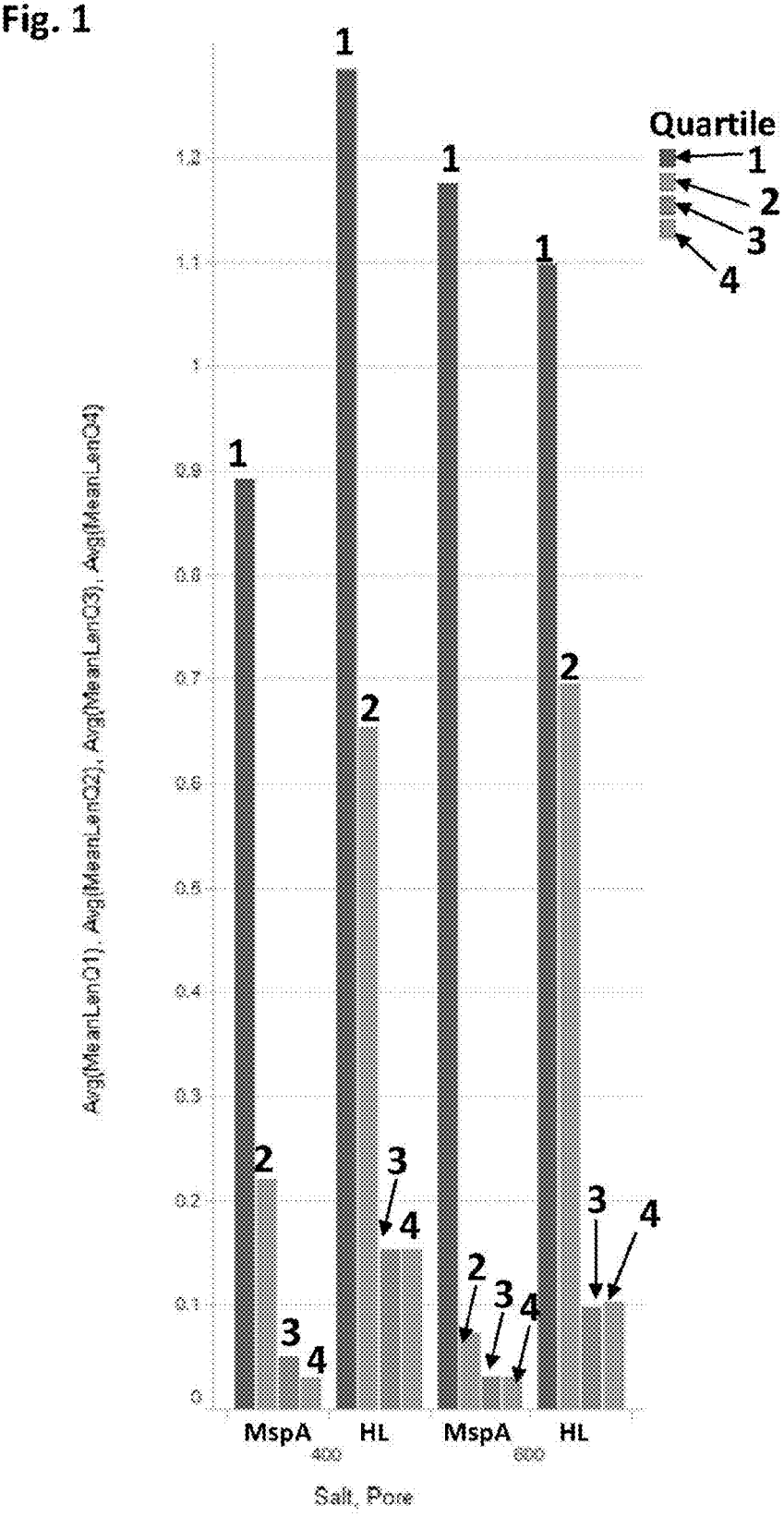
FIG. 1 shows the average dwell time of individual current levels as a single DNA strand translocates the nanopore. The data is collated from a number of single molecules and is split into quartiles by current levels.

SEQ ID NO: 1 shows the polynucleotide sequence encoding the NNN-RRK mutant MspA monomer.

SEQ ID NO: 2 (also referred to as "B1") shows the amino acid sequence of the mature form of the NNN-RRK mutant of the MspA monomer. The mutant lacks the signal sequence and the amino terminal methionine (encoded by the start codon) and includes the following mutations: D90N, D91N, D93N, D118R, D134R and E139K. These mutations allow DNA transition through the MspA pore.

SEQ ID NO: 3 shows the polynucleotide sequence encoding the Phi29 DNA polymerase.

SEQ ID NO: 4 shows the amino acid sequence of the Phi29 DNA polymerase.

SEQ ID NO: 5 shows the codon optimised polynucleotide sequence derived from the sbcB gene from E. coli. It encodes the exonuclease I enzyme (EcoExo I) from E. coli.

SEQ ID NO: 6 shows the amino acid sequence of exonuclease I enzyme (EcoExo I) from E. coli.

SEQ ID NO: 7 shows the codon optimised polynucleotide sequence derived from the xthA gene from E. coli. It encodes the exonuclease III enzyme from E. coli.

SEQ ID NO: 8 shows the amino acid sequence of the exonuclease III enzyme from E. coli. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 9 shows the codon optimised polynucleotide sequence derived from the recJ gene from T. thermophilus. It encodes the RecJ enzyme from T. thermophilus (TthRecJ-cd).

SEQ ID NO: 10 shows the amino acid sequence of the RecJ enzyme from T. thermophilus (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 11 shows the codon optimised polynucleotide sequence derived from the bacteriophage lambda exo (redX) gene. It encodes the bacteriophage lambda exonuclease.

SEQ ID NO: 12 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (www.neb.com/nebecomm/products/productM0262.asp). Enzyme initiation on a strand preferentially requires a 5' overhang of approximately 4 nucleotides with a 5' phosphate.

SEQ ID NOs: 13 to 15 show the sequences used in Example 2.

SEQ ID NOs: 16 to 18 show the amino acid sequences of the mature forms of the MspB, C and D mutants respectively. The mature forms lack the signal sequence.

SEQ ID NOs: 19 and 20 show the sequences used in Examples 9, 12 and 15.

SEQ ID NOs: 21 to 23 show the sequences used in Examples 10 and 11.

SEQ ID NOs: 24 to 27 show the sequences used in Example 13.

SEQ ID NO: 28 shows the DNA sequence of the dimer of the mature form of the NNN-RRK mutant of the MspA monomer used in Example 14.

SEQ ID NO: 29 shows the protein sequence of the dimer of the mature form of the NNN-RRK mutant of the MspA monomer used in Example 14.

SEQ ID NO: 30, 31 and 32 show the sequences used in Example 16.

SEQ ID NO: 33 shows the linker sequence shown used in the construct shown in SEQ ID NO: 29.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a mutant" includes "mutants", reference to "a substitution" includes two or more such substitutions, reference to "a pore" includes two or more such pores, reference to "a nucleic acid sequence" includes two or more such sequences, and the like.

All publications, patents and patent applications cited herein, whether supra or infra, are hereby incorporated by reference in their entirety.

Mutant Msp Monomers

The present invention provides mutant Msp monomers. The mutant Msp monomers may be used to form the pores of the invention. A mutant Msp monomer is a monomer whose sequence varies from that of a wild-type Msp monomer and which retains the ability to form a pore. Methods for confirming the ability of mutant monomers to form pores are well-known in the art and are discussed in more detail below.

The mutant monomers have improved nucleotide reading properties i.e. display improved nucleotide capture and discrimination. In particular, pores constructed from the mutant monomers capture nucleotides and nucleic acids more easily than the wild type. In addition, pores constructed from the mutant monomers display an increased current range, which makes it easier to discriminate between different nucleotides, and a reduced variance of states, which increases the signal-to-noise ratio. In addition, the number of nucleotides contributing to the current as the nucleic acid moves through pores constructed from the mutants is decreased. This makes it easier to identify a direct relationship between the observed current as the nucleic acid moves through the pore and the nucleic acid sequence. The improved nucleotide reading properties of the mutants are achieved via five main mechanisms, namely by changes in the:

sterics (increasing or decreasing the size of amino acid residues);
charge (e.g. introducing +ve charge to interact with the nucleic acid sequence);
hydrogen bonding (e.g. introducing amino acids that can hydrogen bond to the base pairs);
pi stacking (e,g, introducing amino acids that interact through delocalised electron pi systems); and/or
alteration of the structure of the pore (e.g. introducing amino acids that increase the size of the vestibule and/or constriction).

Any one or more of these five mechanisms may be responsible for the improved properties of the pores of the invention. For instance, a pore of the invention may display improved nucleotide reading properties as a result of altered sterics, altered hydrogen bonding and an altered structure.

The introduction of bulky residues, such as phenylalanine (F), tryptophan (W), tyrosine (Y) or histidine (H), increases the sterics of the pore. The introduction of aromatic residues, such as phenylalanine (F), tryptophan (W), tyrosine (Y) or histidine (H), also increases the pi staking in the pore. The introduction of bulky or aromatic residues also alters the structure of the pore, for instance by opening up the pore and increasing the size of the vestibule and/or constriction. This is described in more detail below.

A mutant monomer of the invention comprises a variant of the sequence shown in SEQ ID NO: 2. SEQ ID NO: 2 is the NNN-RRK mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore.

The variant comprises at least one of the following mutations:

(a) asparagine (N), serine (S), glutamine (Q) or threonine (T) at position 88;
(b) serine (S), glutamine (Q) or tyrosine (Y) at position 90;
(c) leucine (L) or serine (S) at position 105;
(d) arginine (R) at position 126;
(e) serine (S) at position 75;
(f) serine (S) at position 77;
(g) arginine (R) at position 59;
(h) glutamine (Q), asparagine (N) or threonine (T) at position 75;
(i) glutamine (Q), asparagine (N) or threonine (T) at position 77;
(j) leucine (L) at position 78;
(k) asparagine (N) at position 81;
(l) asparagine (N) at position 83;
(m) serine (S) or threonine (T) at position 86;
(n) phenylalanine (F), valine (V) or leucine (L) at position 87;
(o) tyrosine (Y), phenylalanine (F), valine (V), arginine (R), alanine (A), glycine (G) or cysteine (C) at position 88;
(p) phenylalanine (F), valine (V) or leucine (L) at position 89;
(q) leucine (L), phenylalanine (F), tryptophan (W), histidine (H), threonine (T), glycine (G), alanine (A), valine (V), arginine (R), lysine (K), asparagine (N) or cysteine (C) at position 90;
(r) serine (S), glutamine (Q), leucine (L), methionine (M), isoleucine (I), alanine (A), valine (V), glycine (G), phenylalanine (F), tryptophan (W), tyrosine (Y), histidine (H), threonine (T), arginine (R), lysine (K), asparagine (N) or cysteine (C) at position 91;
(s) alanine (A) or serine (S) at position 92;
(t) serine (S), alanine (A), threonine (T), glycine (G) at position 93;
(u) leucine (L) at position 94;
(v) valine (V) at position 95;
(w) arginine (R), aspartic acid (D), valine (V), asparagine (N), serine (S) or threonine (T) at position 96;
(x) serine (S) at position 97;
(y) serine (S) at position 98;
(z) serine (S) at position 99;
(aa) serine (S) at position 100;
(bb) phenylalanine (F) at position 101;
(cc) lysine (K), serine (S) or threonine (T) at position 102;
(dd) alanine (A), glutamine (Q), asparagine (N), glycine (G) or threonine (T) at position 103;
(ee) isoleucine at position 104;
(ff) tyrosine (Y), alanine (A), glutamine (Q), asparagine (N), threonine (T), phenylalanine (F), tryptophan (W), histidine (H), glycine (G), valine (V), arginine (R), lysine (K), proline (P), or cysteine (C) at position 105;
(gg) phenylalanine (F), isoleucine (I), valine (V) or serine (S) at position 106;
(hh) proline (P) or serine (S) at position 108;
(ii) asparagine (N) at position 118;
(jj) serine (S) or cysteine (C) at position 103; and
(kk) cysteine at one or more of positions 10 to 15, 51 to 60, 136 to 139 and 168 to 172.

In wild-type MspA, residues 88 and 105 in each monomer form a hydrophobic ring in the inner constriction of the pore. The hydrophobic residues at positions L88 and I105 sit just above the main constriction of the pore, facing into the aqueous channel. Mutation of these residues produces pores that have significantly higher open pore currents to the baseline (SEQ ID NO: 2). The current differences observed when mutations are made at these positions are significantly higher than would be expected from making a single mutation. This surprising result implies that mutations at these positions may have an effect on the structure of the channel rather than just the local environment at these residues. Although the SEQ ID NO: 2 baseline has been reported to exhibit a wide range of pore conductance, the reason for this is not well understood. Mutations to positions L88 and I105 result in the dominant pore current level being significantly higher than the baseline pore. In addition, this higher conductance state is the dominant conformation of the mutant, which is desirable for a large current range and increased signal to noise.

The introduction of N, S, Q or T at position 88 (i.e. mutation (a) above) introduces into the inner constriction of the pore an amino acid that can hydrogen bond to the nucleotides in a nucleic acid.

Residues 90 and 91 in each monomer also form part of the inner constriction of the pore. Residue 118 in each monomer is present within the vestibule of the pore. Residue 134 in each monomer is part of the entrance to the pore.

The introduction of S, Q or Y at position 90 (i.e. mutation (b) above) introduces into the inner constriction of the pore an amino acid that can hydrogen bond to the nucleotides in a nucleic acid.

The variant may include any number of mutations (a) to (kk), such as 1, 2, 3, 4, 5, 6, 7, 8, 9, 10 or more of the mutations. Preferred combinations of mutations are discussed below. The amino acids introduced into the variant may be naturally-occurring or non-naturally occurring derivatives thereof. The amino acids introduced into the variant may be D-amino acids.

Any number of cysteines may be introduced into the variant. Cysteines are preferably introduced at one or more, such as two or all of, positions 90, 91 and 103. These positions may be useful for chemical attachment of a molecular adaptor as discussed in more detail below. Any number of cysteines, such as 2, 3, 4, 5, 6 or more cysteines, may be introduced at positions 10 to 15, 51 to 60, 136 to 139 and 168 to 172. These positions are present in non-conserved loop regions of the pore and so are useful for chemically attaching a nucleic acid binding protein to the pore as discussed in more detail below.

In a preferred embodiment, the variant comprises one or more of the substitutions shown in (A) to (Z) below. The variant may include any number of the substitutions in A to Z, such as 1, 2, 3, 4 or 5.

(A) The introduction of one or more of (i) serine (S) at position 75, (ii) serine (S) at position 77, (iii) asparagine (N) at position 88, (iv) glutamine (Q) at position 90 and (v) arginine (R) at position 126. The variant may include 1, 2, 3, 4 or 5 of these substitutions. The advantages of homo-octameric pores including all four substitutions in each monomer are shown in Table 3 below.

(B) The introduction of one or more of (i) glutamine (Q) at position 90 and (ii) arginine (R) at position 126. The variant may include 1 or 2 of these substitutions. The advantages of homo-octameric pores including both substitutions in each monomer are shown in Table 3 below.

(C) The introduction of one or more of (i) asparagine (N) at position 88, (ii) glutamine (Q) at position 90 and (iii) arginine (R) at position 126. The variant may include 1, 2 or 3 of these substitutions. The advantages of homo-octameric pores including all three of these substitutions in each monomer are shown in Table 3 below.

(D) The introduction of one or more of (i) serine (S) at position 88 and (ii) glutamine (Q) at position 90. The variant may include 1 or 2 of these substitutions. The advantages of homo-octameric pores including both substitutions in each monomer are shown in Table 3 below.

(E) The introduction of one or more of (i) asparagine (N) at position 88 and (ii) glutamine (Q) at position 90. The variant may include 1 or 2 of these substitutions. The advantages of homo-octameric pores including both substitutions in each monomer are shown in Table 3 below.

(F) The introduction of one or more of (i) glutamine (Q) at position 90 and (ii) alanine (A) at position 105. The variant may include 1 or 2 of these substitutions. The advantages of homo-octameric pores including both substitutions in each monomer are shown in Table 2 below.

(G) The introduction of one or more of (i) serine (S) at position 90 and (ii) serine (S) at position 92. The variant may include 1 or 2 of these substitutions. The advantages of homo-octameric pores including both substitutions in each monomer are shown in Table 2 below.

(H) The introduction of one or more of (i) threonine (T) at position 88 and (ii) serine (S) at position 90. The variant may include 1 or 2 of these substitutions. The advantages of homo-octameric pores including both substitutions in each monomer are shown in Table 2 below.

(I) The introduction of one or more of (i) glutamine (Q) at position 87 and (ii) serine (S) at position 90. The variant may include 1 or 2 of these substitutions. The advantages of homo-octameric pores including both substitutions in each monomer are shown in Table 2 below.

(J) The introduction of one or more of (i) tyrosine (Y) at position 89 and (ii) serine (S) at position 90. The variant may include 1 or 2 of these substitutions. The advantages of homo-octameric pores including both substitutions in each monomer are shown in Table 2 below.

(K) The introduction of one or more of (i) asparagine (N) at position 88 and (ii) phenylalanine (F) at position 89. The variant may include 1 or 2 of these substitutions. The advantages of homo-octameric pores including both substitutions in each monomer are shown in Table 2 below.

(L) The introduction of one or more of (i) asparagine (N) at position 88 and (ii) tyrosine (Y) at position 89. The variant may include 1 or 2 of these substitutions. The advantages of homo-octameric pores including both substitutions in each monomer are shown in Table 2 below.

(M) The introduction of one or more of (i) serine (S) at position 90 and (ii) alanine (A) at position 92. The variant may include 1 or 2 of these substitutions. The advantages of homo-octameric pores including both substitutions in each monomer are shown in Table 2 below.

(N) The introduction of one or more of (i) serine (S) at position 90 and (ii) asparagine (N) at position 94. The variant may include 1 or 2 of these substitutions. The advantages of homo-octameric pores including both substitutions in each monomer are shown in Table 2 below.

(O) The introduction of one or more of (i) serine (S) at position 90 and (ii) isoleucine (I) at position 104. The variant may include 1 or 2 of these substitutions. The advantages of homo-octameric pores including both substitutions in each monomer are shown in Table 2 below.

(P) The introduction of one or more of (i) aspartic acid (D) at position 88 and (ii) lysine (K) at position 105. The variant may include 1 or 2 of these substitutions. The advantages of homo-octameric pores including both substitutions in each monomer are shown in Table 2 below.

(Q) The introduction of one or more of (i) asparagine (N) at position 88 and (ii) arginine (R) at position 126. The variant may include 1 or 2 of these substitutions. The advantages of homo-octameric pores including both substitutions in each monomer are shown in Table 2 below.

(R) The one or more of (i) asparagine (N) at position 88, (ii) glutamine (Q) at position 90 and (iii) arginine (R) at position 91. The variant may include 1, 2 or 3 of these substitutions. The advantages of homo-octameric pores including all three substitutions in each monomer are shown in Table 2 below.

(S) The introduction of or more of (i) asparagine (N) at position 88, (ii) glutamine (Q) at position 90 and (iii) serine (S) at position 91. The variant may include 1, 2 or 3 of these substitutions. The advantages of homo-octameric pores including all three substitutions in each monomer are shown in Table 2 below.

(T) The introduction of one or more of (i) asparagine (N) at position 88, (ii) glutamine (Q) at position 90 and (iii) valine (V) at position 105. The variant may include 1, 2 or 3 of these substitutions. The advantages of homo-octameric pores including all three substitutions in each monomer are shown in Table 2 below.

(U) The introduction of one or more of (i) glutamine (Q) at position 90, (ii) serine (S) at position 93 and (iii) alamine (A) at position 105. The variant may include 1, 2 or 3 of these substitutions. The advantages of homo-octameric pores including all three substitutions in each monomer are shown in Table 2 below.

(V) The introduction of one or more of (i) phenylalanine (F), tryptophan (W), tyrosine (Y) or histidine (H) at position 90, (ii) phenylalanine (F), tryptophan (W), tyrosine (Y) or histidine (H) at position 91 and (iii) phenylalanine (F), tryptophan (W), tyrosine (Y) or histidine (H) at position 105. The variant may include 1, 2 or 3 of these substitutions. The introduction of these bulky, aromatic residues increases the sterics and pi stacking in the vestibule and/or constriction of the pore. They also increase the size of the vestibule and/or constriction (i.e. open up the pore).

(W) The introduction of one or more of (i) serine (S), threonine (T), glycine (G), alanine (A) or valine (V) at position 90, (ii) serine (S), threonine (T), glycine (G), alanine (A) or valine (V) at position 91 and (iii) serine (S), threonine (T), glycine (G), alanine (A) or valine (V) at position 105. The variant may include 1, 2 or 3 of these substitutions. The introduction of smaller residues decreases the sterics in the vestibule and/or constriction of the pore.

(X) The introduction of serine (S), arginine (R), lysine (K) or histidine (H) at position 90 and/or serine (S), arginine (R), lysine (K) or histidine (H) at position 91. The introduction of positively-charged residues (R, K or H) increases the interactions between the constriction of the pore and the nucleic acid sequence.

(Y) The introduction of serine (S), threonine (T), asparagine (N), glutamine (Q), tyrosine (Y) or histidine (H) at position 90 and/or serine (S), threonine (T), asparagine (N), glutamine (Q), tyrosine (Y) or histidine (H) at position 91. The introduction of these residues increases the hydrogen bonding that occurs between the constriction of the pore and the nucleic acid sequence. They also increase the size of the vestibule and/or constriction (i.e. open up the pore).

(Z) The introduction of cysteine at one or more of positions 90, 91 and 103. This allows chemical groups to be attached to the pore via cysteine linkage. This is discussed in more detail above and below.

Preferred variants include, but are not limited to, those comprising at least one of the following substitution(s): L88N; L88S; L88Q; L88T; N90S; N90Q; N90Y; I105L; I105S; Q126R; G75S; G77S; G75S, G77S, L88N and Q126R; G75S, G77S, L88N, N90Q and Q126R; N90Q and Q126R; L88N, N90Q and Q126R; L88S and N90Q; L88N and N90Q; E59R; G75Q; G75N; G75S; G75T; G77Q; G77N; G77S; G77T; I78L; S81N; T83N; N86S; N86T; I87F; I87V; I87L; L88N; L88S; L88Y; L88F; L88V; L88Q; L88T; I89F; I89V; I89L; N90S; N90Q; N90L; N90Y; N91S; N91Q; N91L; N91M; N91I; N91A; N91V; N91G; G92A; G92S; N93S; N93A; N93T; I94L; T95V; A96R; A96D; A96V; A96N; A96S; A96T; P97S; P98S; F99S; G100S; L101F; N102K; N102S; N102T; S103A; S103Q; S103N; S103G; S103T; V104I; I105Y; I105L; I105A; I105Q; I105N; I105S; I105T; T106F; T106I; T106V; T106S; N108P; N108S; N90Q and I105A; N90S and G92S; L88T and N90S; I87Q and N90S; I89Y and N90S; L88N and I89F; L88N and I89Y; N90S and G92A; N90S and I94N; N90S and V104I; L88D and I105K; L88N and Q126R; L88N, N90Q and N91R; L88N, N90Q and N91S; L88N, N90Q and I105V; N90Q, N93S and I105A; N91Y; N90Y and N91G; N90G and N91Y; N90G and N91G; I05G; N90R; N91R; N90R and N91R; N90K; N91K; N90K and N91K; N90Q and N91G; N90G and N91Q; N90Q and N91Q; R118N; N91C; N90C; N90W; N91W; N90K; N91K; N90R; N91R; N90S and N91S; N90Y and I105A; N90G and I105A; N90Q and I105A; N90S and I105A; L88A and I105A; L88S and I105S; L88N and I105N; N90G and N93G; N90G; N93G; N90G and N91A; I105K; I105R; I105V; I105P; I105W; L88R; L88A; L88G; L88N; N90R and I105A; N90S and I105A; L88A and I105A; L88S and I105S; L88N and I105N; L88C; S103C; and I105C. A particularly preferred variant comprises I105N. Pores constructed from mutant monomers comprising I105N have a residual current that is increased by approximately 80%. The change in current in relation to different nucleotides is also increased. This reflects a change in structure of pores constructed from mutant monomers comprising I105N. Such pores therefore have an improved ability to discriminate nucleotides.

Preferred single mutants and their advantages when used in homo-octameric pores are shown in Table 1 below.

TABLE 1

| Position | Substitution | Advantage(s) |
|---|---|---|
| E59 | R | Increased DNA capture |
| G75 | Q | Less variance |
| G75 | N | Less variance |
| G75 | S | Less variance |
| G75 | T | Less variance |
| G77 | Q | Less variance |
| G77 | N | Less variance |
| G77 | S | Less variance |
| G77 | T | Less variance |
| I78 | L | Tighter distribution of pore sizes |
| S81 | N | More stable beta barrel |
| T83 | N | More stable beta barrel |
| N86 | S | Larger DNA range |
| N86 | T | Larger DNA range |
| I87 | F | Less variance |
| I87 | V | Less variance |
| I87 | L | Less variance |
| L88 | N | Less variance |
| L88 | S | Less variance |
| L88 | Y | Altered DNA-noise profile |
| L88 | F | Altered DNA-noise profile |
| L88 | V | Less variance |
| L88 | Q | Less variance |
| L88 | T | Larger DNA range<br>Less variance |
| I89 | F | Larger DNA range<br>Altered DNA recognition |
| I89 | V | Tighter distribution of pore sizes |
| I89 | L | Tighter distribution of pore sizes |
| N90 | S | Less variance<br>Altered DNA recognition |
| N90 | Q | Increased pore current<br>Increased DNA range<br>Altered DNA recognition |

TABLE 1-continued

| Position | Substitution | Advantage(s) |
|---|---|---|
| N90 | L | Altered DNA recognition |
| N90 | Y | Altered DNA recognition |
| N91 | S | Altered DNA recognition |
| N91 | Q | Altered DNA recognition |
| N91 | L | Altered DNA recognition |
| N91 | M | Altered DNA recognition |
| N91 | I | Altered DNA recognition |
| N91 | A | Altered DNA recognition |
| N91 | V | Altered DNA recognition |
| N91 | G | Altered DNA recognition |
| G92 | A | Larger DNA range. |
| G92 | S | Stabilises N90S mutations |
| N93 | S | Larger DNA range. |
| N93 | A | Larger DNA range. |
| N93 | T | Larger DNA range<br>Altered DNA discrimination |
| I94 | L | Larger DNA range. |
| T95 | V | Stable open pore current level<br>Altered DNA range |
| A96 | R | Increased DNA capture |
| A96 | D | Altered DNA recognition |
| A96 | V | Good pores<br>Altered pore variance |
| A96 | N | Good pores<br>Altered pore variance |
| A96 | S | Good pores<br>Altered pore variance |
| A96 | T | Good pores<br>Altered pore variance |
| P97 | S | Good pores<br>Altered pore variance |
| P98 | S | Good pores<br>Altered pore variance |
| F99 | S | Good pores<br>Altered pore variance |
| G100 | S | Good pores<br>Altered pore variance |
| L101 | F | Good pores<br>Altered pore variance |
| N102 | K | Increased DNA capture |
| N102 | S | Altered pore variance profil<br>Larger DNA range |
| N102 | T | Altered DNA discrimination. |
| S103 | A | Altered DNA recognition |
| S103 | Q | Larger DNA range<br>Altered DNA recognition |
| S103 | N | Larger DNA range<br>Altered DNA recognition |
| S103 | G | Larger DNA range<br>Altered DNA recognition |
| S103 | T | Altered DNA discrimination. |
| V104 | I | Altered DNA discrimination. |
| I105 | Y | Larger DNA range<br>Altered DNA recognition |
| I105 | L | Larger DNA range<br>Less variance |
| I105 | A | Larger DNA range. |
| I105 | Q | Altered DNA recognition |
| I105 | N | Larger DNA range |
| I105 | S | Altered DNA recognition |
| I105 | T | Altered DNA recognition |
| T106 | F | Stable open pore current level<br>Altered DNA variance |
| T106 | I | Altered DNA recognition |
| T106 | V | Altered DNA recognition |
| T106 | S | Larger DNA range |
| N108 | P | Stable open pore current level<br>Altered DNA variance |
| N108 | S | Stable open pore current level<br>Altered DNA variance |
| Q126 | R | Increased DNA capture |

Preferred multiple mutants and their advantages when used in homo-octameric pores are shown in Table 2 below.

TABLE 2

| Mutant | Advantage(s) |
|---|---|
| N90Q/I105A | Altered DNA recognition |
| N90S/G92S | Altered DNA recognition |
| L88T/N90S | Altered DNA recognition |
| I87Q/N90S | Altered DNA recognition |
| I89Y/N90S | Altered DNA recognition |
| L88N/I89F | Altered DNA recognition. |
| L88N/I89Y | Altered DNA recognition<br>Larger DNA range |
| N90S/G92A | Altered DNA recognition |
| N90S/I94N | Altered DNA recognition |
| N90S/V104I | Altered DNA recognition |
| L88D/I105K | Altered DNA recognition |
| L88N/Q126R | Less variance<br>Increased DNA capture |
| L88N/N90Q/N91R | Altered DNA discrimination<br>Increased DNA capture |
| L88N/N90Q/N91S | Altered DNA discrimination |
| L88N/N90Q/I105V | Altered DNA discrimination |
| N90Q-N93S-I105A | Altered DNA discrimination |

The most preferred mutants and their advantages when used in homo-octameric pores are shown in the Table 3 below.

TABLE 3

Most preferred mutants and their advantages

| Mutant | Advantage(s) |
|---|---|
| G75S/G77S/L88N/Q126R | Stable open pore current<br>Increased DNA capture<br>Less variance |
| G75S/G77S/L88N/N90Q/Q126R | Stable open pore current<br>Increased DNA capture<br>Less variance<br>Altered DNA recognition |
| L88N | Less variance |
| N90Q/Q126R | Increased pore current<br>Increased DNA range<br>Altered DNA recognition<br>Increased DNA capture |
| L88N/N90Q/Q126R | Increased pore current<br>Increased DNA range<br>Altered DNA recognition<br>Increased DNA capture |
| L88S/N90Q | Less variance<br>Altered DNA recognition |
| N90S | Less variance<br>Altered DNA recognition |
| N90Q | Increased pore current<br>Increased DNA range<br>Altered DNA recognition |
| L88S | Less variance |
| L88Q | Less variance |
| L88N/N90Q | Increased pore current<br>Increased DNA range<br>Altered DNA recognition |
| I105L | Less variance. Large DNA range. |
| I105S | Large DNA range. |

In addition to the specific mutations discussed above, the variant may include other mutations. Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

SEQ ID NO: 2 is the NNN-RRK mutant of the MspA monomer. The variant may comprise any of the mutations in the MspB, C or D monomers compared with MspA. The mature forms of MspB, C and D are show in SEQ ID NOs: 16 to 18. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, N91G, A96Q, N102D, S103T, V104I, S136K and G141A. The variant may comprise combinations of one or more of the mutations and substitutions from Msp B, C and D.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 4 below. Where amino acids have similar polarity, this can also be determined by reference to the hydropathy scale for amino acid side chains in Table 5.

TABLE 4

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 5

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores of the invention. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below. A variant may have a methionine at the amino terminal of SEQ ID NO: 2.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The mutant monomers may be modified to assist their identification or purification, for example by the addition of histidine residues (a his tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 Jul.; 4(7):497-505).

The mutant monomer may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

The mutant monomer may be made synthetically or by recombinant means. For example, the pore may be synthesized by in vitro translation and transcription (IVTT). The amino acid sequence of the mutant monomer may be modified to include non-naturally occurring amino acids or to increase the stability of the monomer. When the mutant monomer is produced by synthetic means, such amino acids may be introduced during production. The mutant monomer may also be altered following either synthetic or recombinant production.

The mutant monomer may also be produced using D-amino acids. For instance, the mutant monomer may comprise a mixture of L-amino acids and D-amino acids. This is conventional in the art for producing such proteins or peptides.

The mutant monomer contains one or more specific modifications to facilitate nucleotide discrimination. The mutant monomer may also contain other non-specific modifications as long as they do not interfere with pore formation.

A number of non-specific side chain modifications are known in the art and may be made to the side chains of the mutant monomer. Such modifications include, for example, reductive alkylation of amino acids by reaction with an aldehyde followed by reduction with $NaBH_4$, amidination with methylacetimidate or acylation with acetic anhydride.

The mutant monomer can be produced using standard methods known in the art. Polynucleotide sequences encoding a mutant monomer may be derived and replicated using standard methods in the art. Such sequences are discussed in more detail below. Polynucleotide sequences encoding a mutant monomer may be expressed in a bacterial host cell using standard techniques in the art. The mutant monomer may be produced in a cell by in situ expression of the polypeptide from a recombinant expression vector. The expression vector optionally carries an inducible promoter to control the expression of the polypeptide.

A mutant monomer may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system. The mutant monomer may then be inserted into a naturally occurring or artificial membrane for use in accordance with the invention. Methods for inserting pore into membranes are discussed below.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant monomer may be chemically modified by the attachment of any molecule. For instance, the mutant monomer may be chemically modified by attachment of a dye or a fluorophore.

In some embodiments, the mutant monomer is chemically modified with a molecular adaptor that facilitates the interaction between a pore comprising the monomer and a target nucleotide or target nucleic acid sequence. The presence of the adaptor improves the host-guest chemistry of the pore and the nucleotide or nucleic acid sequence and thereby improves the sequencing ability of pores formed from the mutant monomer. The principles of host-guest chemistry are well-known in the art. The adaptor has an effect on the physical or chemical properties of the pore that improves its interaction with the nucleotide or nucleic acid sequence. The adaptor may alter the charge of the barrel or channel of the pore or specifically interact with or bind to the nucleotide or nucleic acid sequence thereby facilitating its interaction with the pore.

The molecular adaptor is preferably a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor preferably has eight-fold symmetry since Msp typically has eight subunits around a central axis. This is discussed in more detail below.

The adaptor typically interacts with the nucleotide or nucleic acid sequence via host-guest chemistry. The adaptor is typically capable of interacting with the nucleotide or nucleic acid sequence. The adaptor comprises one or more chemical groups that are capable of interacting with the nucleotide or nucleic acid sequence. The one or more chemical groups preferably interact with the nucleotide or nucleic acid sequence by non-covalent interactions, such as hydrophobic interactions, hydrogen bonding, Van der Waal's forces, π-cation interactions and/or electrostatic forces. The one or more chemical groups that are capable of interacting with the nucleotide or nucleic acid sequence are preferably positively charged. The one or more chemical groups that are capable of interacting with the nucleotide or nucleic acid sequence more preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of eight amino groups. A ring of protonated amino groups may interact with negatively charged phosphate groups in the nucleotide or nucleic acid sequence.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, π-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that that facilitates the interaction between the pore and the nucleotide or nucleic acid sequence can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem. Soc.* 116, 6081-6088. The adaptor is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). The guanidino group in $gu_7$-βCD has a much higher pKa than the primary amines in $am_7$-βCD and so it more positively charged. This $gu_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono(2-pyridyl)dithiopropanoyl-β-cyclodextrin ($am_6amPDP_1$-βCD).

More suitable adaptors include γ-cyclodextrins, which comprise 8 sugar units (and therefore have eight-fold symmetry). The γ-cyclodextrin may contain a linker molecule or may be modified to comprise all or more of the modified sugar units used in the β-cyclodextrin examples discussed above.

The molecular adaptor is preferably covalently attached to the mutant monomer. The adaptor can be covalently attached to the pore using any method known in the art. The adaptor is typically attached via chemical linkage. If the molecular adaptor is attached via cysteine linkage, the one or more cysteines have preferably been introduced to the mutant by substitution. The mutant monomers of the invention can of course comprise a cysteine residue at one or more of positions 88, 90, 91, 103 and 105. The mutant monomer may be chemically modified by attachment of a molecular adaptor to one or more, such as 2, 3, 4 or 5, of these cysteines. Alternatively, the mutant monomer may be chemically modified by attachment of a molecule to one or more cysteines introduced at other positions. The molecular adaptor is preferably attached to one or more of positions 90, 91 and 103 of SEQ ID NO: 2.

The reactivity of cysteine residues may be enhanced by modification of the adjacent residues. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the mutant monomer before a linker is attached. The molecule may be attached directly to the mutant monomer. The molecule is preferably attached to the mutant monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and Maleimide-based linkers.

In other embodiment, the monomer may be attached to a nucleic acid binding protein. This forms a modular sequencing system that may be used in the methods of sequencing of the invention. Nucleic acid binding proteins are discussed below.

The nucleic acid binding protein is preferably covalently attached to the mutant monomer. The protein can be covalently attached to the pore using any method known in the art. The monomer and protein may be chemically fused or genetically fused. The monomer and protein are genetically fused if the whole construct is expressed from a single polynucleotide sequence. Genetic fusion of a pore to a nucleic acid binding protein is discussed in International Application No. PCT/GB09/001679 (published as WO 2010/004265).

If the nucleic acid binding protein is attached via cysteine linkage, the one or more cysteines have preferably been introduced to the mutant by substitution. The mutant monomers of the invention can of course comprise cysteine residues at one or more of positions 10 to 15, 51 to 60, 136 to 139 and 168 to 172. These positions are present in loop regions which have low conservation amongst homologues indicating that mutations or insertions may be tolerated.

They are therefore suitable for attaching a nucleic acid binding protein. The reactivity of cysteine residues may be enhanced by modification as described above.

The nucleic acid binding protein may be attached directly to the mutant monomer or via one or more linkers. The molecule may be attached to the mutant monomer using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The mutant monomer may be chemically modified with a molecular adaptor and a nucleic acid binding protein.

Constructs

The invention also provides a construct comprising two or more covalently attached monomers derived from Msp. The construct of the invention retains its ability to form a pore. One or more constructs of the invention may be used to form pores for characterising, such as sequencing, nucleic acids sequences. The construct may comprise 2, 3, 4, 5, 6, 7, 8, 9 or 10 monomers. The two or more monomers may be the same or different.

The monomers do not have to be mutant monomers of the invention. For instance, at least one monomer may comprise the sequence shown in SEQ ID NO: 2. Alternatively, at least one monomer may comprise a variant of SEQ ID NO: 2 which is at least 50% homologous to SEQ ID NO: 2 over its entire sequence based on amino acid identity, but does not include any of the specific mutations required by the mutant monomers of the invention. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. In a preferred embodiment, at least one monomer in the construct is a mutant monomer of the invention. All of the monomers in the construct may be a mutant monomer of the invention. The mutant monomers may be the same or different. In a more preferred embodiment, the construct comprises two monomers and at least one of the monomers is a mutant monomer of the invention.

The monomers are preferably genetically fused. Monomers are genetically fused if the whole construct is expressed from a single polynucleotide sequence. The coding sequences of the monomers may be combined in any way to form a single polynucleotide sequence encoding the construct.

The monomers may be genetically fused in any configuration. The monomers may be fused via their terminal amino acids. For instance, the amino terminus of the one monomer may be fused to the carboxy terminus of another monomer. If the construct is formed from the genetic fusion of two or more monomers each comprising the sequence shown in SEQ ID NO: 2 or a variant thereof, the second and subsequent monomers in the construct (in the amino to carboxy direction) may comprise a methionine at their amino terminal ends (each of which is fused to the carboxy terminus of the previous monomer). For instance, if M is a monomer comprising the sequence shown in SEQ ID NO: 2 or a variant (without an amino terminal methionine) and mM is a monomer comprising the sequence shown in SEQ ID NO: 2 or a variant with an amino terminal methionine, the construct may comprise the sequence M-mM, M-mM-mM or M-mM-mM-mM. The presences of these methionines typically results from the expression of the start codons (i.e. ATGs) at the 5' end of the polynucleotides encoding the second or subsequent monomers within the polynucleotide encoding entire construct. The first monomer in the construct (in the amino to carboxy direction) may also comprise a methionine (e.g. mM-mM, mM-mM-mM or mM-mM-mM-mM).

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed above may be used. The construct preferably comprises the sequence shown in SEQ ID NO: 29 or a variant thereof. Each monomer in SEQ ID NO: 29 comprises the sequence shown in SEQ ID NO: 2 or a variant thereof. The second monomer also comprises a methionine at its amino terminus as described above. The two monomers are linked by a peptide linker. A variant of SEQ ID NO: 29 may vary from SEQ ID NO: 29 in any of the ways discussed above with reference to variants of SEQ ID NO: 2. The linker may also be modified or replaced with a peptide linker discussed above.

In another preferred embodiment, the monomers are chemically fused. A subunit is chemically fused to an enzyme if the two parts are chemically attached, for instance via a chemical crosslinker. Any of the chemical crosslinkers discussed above may be used. The linker may be attached to one or more cysteine residues introduced into a mutant monomer of the invention. Alternatively, the linker may be attached to a terminus of one of the monomers in the construct.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described in International Application No. PCT/GB10/000132 (published as WO 2010/086602).

Polynucleotides

The present invention also provides polynucleotide sequences which encode a mutant monomer of the invention. The mutant monomer may be any of those discussed above. The polynucleotide sequence preferably comprises a sequence at least 50%, 60%, 70%, 80%, 90% or 95% homologous based on nucleotide identity to the sequence of SEQ ID NO: 1 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 1 on the basis of the degeneracy of the genetic code.

The present invention also provides polynucleotide sequences which encode any of the genetically fused constructs of the invention. The polynucleotide preferably comprises two or more sequences as shown in SEQ ID NO: 1 or a variant thereof as described above. The polynucleotide sequence preferably comprises the sequence of SEQ ID NO: 28 or a sequence at least 50%, 60%, 70%, 80%, 90% or 95% homologous based on nucleotide identity to the sequence of SEQ ID NO: 28 over the entire sequence. There may be at least 80%, for example at least 85%, 90% or 95% nucleotide identity over a stretch of 600 or more, for example 750, 900, 1050 or 1200 or more, contiguous nucleotides ("hard homology"). Homology may be calculated as described above. The polynucleotide sequence may comprise a sequence that differs from SEQ ID NO: 28 on the basis of the degeneracy of the genetic code.

Polynucleotide sequences may be derived and replicated using standard methods in the art. Chromosomal DNA encoding wild-type Msp may be extracted from a pore producing organism, such as *Mycobacterium smegmatis*. The gene encoding the pore subunit may be amplified using PCR involving specific primers. The amplified sequence may then undergo site-directed mutagenesis. Suitable methods of site-directed mutagenesis are known in the art and include, for example, combine chain reaction. Polynucleotides encoding a construct of the invention can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct of the invention can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane. Alternatively, the recombinant pore produced in this manner may be removed from the host cell and inserted into another membrane. When producing pores comprising at least two different subunits, the different subunits may be expressed separately in different host cells as described above, removed from the host cells and assembled into a pore in a separate membrane, such as a rabbit cell membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the pore subunit at a high level. Host cells transformed with a polynucleotide sequence will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter. In addition to the conditions listed above any of the methods cited in Proc Natl Acad Sci USA. 2008 Dec. 30; 105(52):20647-52 may be used to express the Msp proteins.

Pores

The invention also provides various pores. The pores of the invention are ideal for characterising, such as sequencing, nucleic acid sequences because they can discriminate between different nucleotides with a high degree of sensitivity. The pores can surprisingly distinguish between the four nucleotides in DNA and RNA. The pores of the invention can even distinguish between methylated and unmethylated nucleotides. The base resolution of pores of the invention is surprisingly high. The pores show almost complete separation of all four DNA nucleotides. The pores further discriminate between deoxycytidine monophosphate (dCMP) and methyl-dCMP based on the dwell time in the pore and the current flowing through the pore.

The pores of the invention can also discriminate between different nucleotides under a range of conditions. In particular, the pores will discriminate between nucleotides under conditions that are favourable to the characterising, such as sequencing, of nucleic acids. The extent to which the pores of the invention can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The pores of the invention may also be used to identify nucleic acid polymers from the interaction with one or more monomers rather than on a nucleotide by nucleotide basis.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it present in a form that comprises less than 10%, less than 5%, less than 2% or less than 1% of other components, such as lipids or other pores. Alternatively, a pore of the invention may be present in a lipid bilayer.

A pore of the invention may be present as an individual or single pore. Alternatively, a pore of the invention may be present in a homologous or heterologous population of two or more pores.

Homo-Oligomeric Pores

The invention also provides a homo-oligomeric pore derived from Msp comprising identical mutant monomers of the invention. The homo-oligomeric pore preferably comprises one of the mutants shown in Tables 1, 2 and 3. The homo-oligomeric pore of the invention is ideal for characterising, such as sequencing, nucleic acids. The homo-oligomeric pore of the invention may have any of the advantages discussed above. The advantages of specific homo-oligomeric pores of the invention are indicated in Tables 1, 2 and 3.

The homo-oligomeric pore may contain any number of mutant monomers. The pore typically comprises 7, 8, 9 or 10 identical mutant monomers. The pore preferably comprises eight identical mutant monomers. One or more, such as 2, 3, 4, 5, 6, 7, 8, 9 or 10, of the mutant monomers is preferably chemically modified as discussed above.

Methods for making pores are discussed in more detail below.

Hetero-Oligomeric Pores

The invention also provides a hetero-oligomeric pore derived from Msp comprising at least one mutant monomer of the invention, wherein at least one of the eight monomers differs from the others. The hetero-oligomeric pore of the invention is ideal for characterising, such as sequencing, nucleic acids. Hetero-oligomeric pores can be made using methods known in the art (e.g. Protein Sci. 2002 Jul.; 11(7):1813-24).

The hetero-oligomeric pore contains sufficient monomers to form the pore. The monomers may be of any type. The pore typically comprises 7, 8, 9 or 10 monomers. The pore preferably comprises eight monomers.

The pore may comprise at least one monomer comprising (a) the sequence shown in SEQ ID NO: 2 or (b) a variant thereof which does not have a mutation required by the mutant monomers of the invention. Suitable variants are discussed above. In this embodiment, the remaining monomers are preferably mutant monomers of the invention. Hence, the pore may comprise 9, 8, 7, 6, 5, 4, 3, 2 or 1 mutant monomers of the invention.

In a preferred embodiment, the pore comprises (a) one mutant monomer and (b) seven identical monomers, wherein the mutant monomer in (a) is different from the identical monomers in (b). The identical monomers in (b) preferably comprise (i) the sequence shown in SEQ ID NO: 2 or (ii) a variant thereof which does not have a mutation present in the mutant monomers of the invention.

Preferred pores include, but are not limited to, any of the following:
(a) Seven monomers comprising the sequence shown in SEQ ID NO: 2 and one mutant monomer comprising the substitution N90R, N90K, N90Y, N90Q, N90W or N90C. These pores have a single steric amino acid (Y or W), a single charged amino acid (K or R) or a single reactive amino acid (C) introduced into the inner constriction.
(b) Seven monomers comprising the sequence shown in SEQ ID NO: 2 and one mutant monomer comprising the substitution N91R, N91K, N91Y, N91Q, N91W or N91C. These pores have a single steric amino acid (Y or W), a single charged amino acid (K or R) or a single reactive amino acid (C) introduced into the inner constriction.
(c) Seven monomers comprising the sequence shown in SEQ ID NO: 2 and one mutant monomer comprising the substitution L88C, S103C or I105C. These pores have a reactive amino acid introduced into the pore.

In another preferred embodiment, all of the monomers (i.e. 10, 9, 8 or 7 of the monomers) are mutant monomers of the invention and at least one of them differs from the others.

In a more preferred embodiment, the pore comprises eight mutant monomers of the invention and at least one of them differs from the others.

In all the embodiments discussed above, one or more, such as 2, 3, 4, 5, 6, 7, 8, 9 or 10, of the mutant monomers is preferably chemically modified as discussed above. Preferred pores (a) to (c) above are preferably chemically modified by attachment of a molecule to one or more of the introduced cysteines.

Methods for making pores are discussed in more detail below.

Construct-Containing Pores

The invention also provides a pore comprising at least one construct of the invention. A construct of the invention comprises two or more covalently attached monomers derived from Msp. In other words, a construct must contain more than one monomer. The pore contains sufficient constructs and, if necessary, monomers to form the pore. For instance, an octameric pore may comprise (a) two constructs each comprising four monomers or (b) one construct comprising two monomers and six monomers that do not form part of a construct. At least two of the monomers in the pore are in the form of a construct of the invention. The monomers may be of any type. The pore typically comprises 7, 8, 9 or 10 monomers in total (at least two of which must be in a construct). The pore preferably comprises eight monomers (at least two of which must be in a construct).

A pore typically contains (a) one construct comprising two monomers and (b) 5, 6, 7 or 8 monomers. The construct may be any of those discussed above. The monomers may be any of those discussed above, including mutant monomers of the invention.

Another typical pore comprises more than one construct of the invention, such as two, three or four constructs of the invention. Such pores further comprise sufficient monomers to form the pore. The monomer may be any of those discussed above. A further pore of the invention comprises only constructs comprising 2 monomers, for example a pore may comprise 4, 5, 6, 7 or 8 constructs comprising 2 monomers. A specific pore according to the inventions comprises four constructs each comprising two monomers. The constructs may oligomerise into a pore with a structure such that only one monomer of a construct contributes to the barrel or vestibule of the pore. Typically the other monomers of the construct will be on the outside of the barrel or vestibule of the pore. For example, pores of the invention may comprise 5, 6, 7 or 8 constructs comprising 2 monomers where the barrel or vestibule comprises 8 monomers.

Mutations can be introduced into the construct as described above. The mutations may be alternating, i.e. the mutations are different for each monomer within a two monomer construct and the constructs are assembled as a homo-oligomer resulting in alternating modifications. In other words, monomers comprising MutA and MutB are fused and assembled to form an A-B:A-B:A-B:A-B pore. Alternatively, the mutations may be neighbouring, i.e. identical mutations are introduced into two monomers in a construct and this is then oligomerised with different mutant monomers. In other words, monomers comprising MutA are fused follow by oligomerisation with MutB-containing monomers to form A-A:B:B:B:B:B:B.

One or more of the monomers of the invention in a construct-containing pore may be chemically-modified as discussed above.

Methods of Identifying an Individual Nucleotide

The present invention also provides methods of characterising an individual nucleotide. The methods comprise contacting the nucleotide with a pore of the invention so that the nucleotide interacts with the pore and measuring the current passing through the pore during the interaction and thereby characterising the nucleotide. The invention therefore involves nanopore sensing of an individual nucleotide. The invention also provides methods of identifying an individual nucleotide comprising measuring the current passing through the pore during the interaction and thereby determining the identity of the nucleotide. Any of the pores of the invention can be used. The pore of the invention is preferably chemically modified with a molecular adaptor as discussed above.

The nucleotide is present if the current flows through the pore in a manner specific for the nucleotide (i.e. if a distinctive current associated with the nucleotide is detected flowing through the pore). The nucleotide is absent if the current does not flow through the pore in a manner specific for the nucleotide.

The invention can be used to differentiate nucleotides of similar structure on the basis of the different effects they have on the current passing through a pore. Individual nucleotides can be identified at the single molecule level from their current amplitude when they interact with the pore. The invention can also be used to determine whether or not a particular nucleotide is present in a sample. The invention can also be used to measure the concentration of a particular nucleotide in a sample.

The methods may be carried out using any suitable membrane/pore system in which a pore of the invention is inserted into a membrane. The methods are typically carried out using (i) an artificial membrane comprising a pore of the invention, (ii) an isolated, naturally occurring membrane comprising a pore of the invention, or (iii) a cell expressing a pore that has been modified in accordance with the invention. The methods are preferably carried out using an artificial membrane. The membrane may comprise other transmembrane and/or intramembrane proteins as well as other molecules in addition to the pore of the invention.

The membrane forms a barrier to the flow of ions, nucleotides and nucleic acids. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphiles may be synthetic or naturally occurring. The amphiphilic layer may be a monolayer or a bilayer. Non-naturally occurring amphiphiles and amphiphiles which form a monolayer are known in the art and include, for example, block copolymers (Gonzalez-Perez et al., Langmuir, 2009, 25, 10447-10450).

The membrane may be a lipid bilayer. Lipid bilayers suitable for use in accordance with the invention can be made using methods known in the art. For example, lipid bilayer membranes can be formed using the method of Montal and Mueller (Proc. Natl. Acad. Sci. USA 1972; 69: 3561-3566). Lipid bilayers can also be formed using the method described in International Application No. PCT/GB08/000563.

The method of the invention may be carried out using lipid bilayers formed from any membrane lipid including, but not limited to, phospholipids, glycolipids, cholesterol, mycolic acid and mixtures thereof. Any of the lipids described in International Application No. PCT/GB08/000563 may be used.

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as Si3N4, Al2O3, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647). An amphiphilic layer may be formed across a solid state pore. This may be described in the art as hybrid pore formation (Hall et al., Nat Nanotechnol., 2010, 5, 874-877).

Methods are known in the art for inserting pores into membranes, such as lipid bilayers. For example, the pore may be suspended in a purified form in a solution containing a lipid bilayer such that it diffuses to the lipid bilayer and is inserted by binding to the lipid bilayer and assembling into a functional state. Alternatively, the pore may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

The methods of the invention are typically carried out in vitro.

Individual Nucleotide

An individual nucleotide is a single nucleotide. An individual nucleotide is one which is not bound to another nucleotide or nucleic acid by a nucleotide bond. A nucleotide bond involves one of the phosphate groups of a nucleotide being bound to the sugar group of another nucleotide. An individual nucleotide is typically one which is not bound by a nucleotide bond to another nucleic acid sequence of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand.

The methods of the invention may be used to identify any nucleotide. The nucleotide can be naturally occurring or artificial. A nucleotide typically contains a nucleobase, a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

Suitable nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotide is preferably AMP, TMP, GMP, UMP, dAMP, dTMP, dGMP or dCMP.

The nucleotide may be derived from the digestion of a nucleic acid sequence such as ribonucleic acid (RNA) or deoxyribonucleic acid. Nucleic acid sequences can be digested using any method known in the art. Suitable methods include, but are not limited to, those using enzymes or catalysts. Catalytic digestion of nucleic acids is disclosed in Deck et al., Inorg. Chem., 2002; 41: 669-677.

Individual nucleotides from a single nucleic acid sequence may be contacted with the pore in a sequential manner in order to sequence the whole or part of the nucleic acid. Sequencing nucleic acids is discussed in more detail below.

The nucleotide is typically unmodified, such as when the nucleotide is derived from the digestion of a nucleic acid sequence. Alternatively, the nucleotide may be modified or damaged. The nucleotide is typically methylated or oxidised. The nucleotide may be labelled with a revealing label. The revealing label may be any suitable label which allows the nucleotide to be detected. Suitable labels include fluorescent molecules, radioisotopes, e.g. $^{125}$I, $^{35}$S, and linkers such as biotin.

The nucleotide is typically present in any suitable biological sample. Suitable biological samples are discussed above.

Interaction Between the Pore and Nucleotide

The nucleotide may be contacted with the pore on either side of the membrane. The nucleotide may be introduced to the pore on either side of the membrane. The nucleotide may be contacted with the side of the membrane that allows the nucleotide to pass through the pore to the other side of the membrane. For example, the nucleotide is contacted with an end of the pore, which in its native environment allows the entry of ions or small molecules, such as nucleotides, into the barrel or channel of the pore such that the nucleotide may pass through the pore. In such cases, the nucleotide interacts with the pore and/or adaptor as it passes across the membrane through the barrel or channel of the pore. Alternatively, the nucleotide may be contacted with the side of the membrane that allows the nucleotide to interact with the pore via or in conjunction with the adaptor, dissociate from the pore and remain on the same side of the membrane. The present invention provides pores in which the position of the adaptor is fixed. As a result, the nucleotide is preferably contacted with the end of the pore which allows the adaptor to interact with the nucleotide.

The nucleotide may interact with the pore in any manner and at any site. As discussed above, the nucleotide preferably reversibly binds to the pore via or in conjunction with the adaptor. The nucleotide most preferably reversibly binds to the pore via or in conjunction with the adaptor as it passes through the pore across the membrane. The nucleotide can also reversibly bind to the barrel or channel of the pore via or in conjunction with the adaptor as it passes through the pore across the membrane.

During the interaction between the nucleotide and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample. The ratio of different nucleotides within a sample can also be calculated. For instance, the ratio of dCMP to methyl-dCMP can be calculated.

Apparatus

The methods may be carried out using any apparatus that is suitable for investigating a membrane/pore system in which a pore of the invention is inserted into a membrane. The method may be carried out using any apparatus that is suitable for nanopore sensing. For example, the apparatus comprises a chamber comprising an aqueous solution and a barrier that separates the chamber into two sections. The barrier has an aperture in which the membrane containing the pore is formed. The nucleotide may be contacted with the pore by introducing the nucleotide into the chamber. The nucleotide may be introduced into either of the two sections of the chamber.

The methods may be carried out using the apparatus described in International Application No. PCT/GB08/000562.

The methods of the invention involve measuring the current passing through the pore during interaction with the nucleotide. Therefore the apparatus also comprises an electrical circuit capable of applying a potential and measuring an electrical signal across the membrane and pore. The methods may be carried out using a patch clamp or a voltage clamp. The methods preferably involve the use of a voltage clamp.

Sample

The nucleotide is present in any suitable sample. The invention is typically carried out on a sample that is known to contain or suspected to contain the nucleotide. The invention may be carried out on a sample that contains one or more nucleotides whose identity is unknown. Alternatively, the invention may be carried out on a sample to confirm the identity of one or more nucleotides whose presence in the sample is known or expected.

The sample may be a biological sample. The invention may be carried out in vitro on a sample obtained from or extracted from any organism or microorganism. The organism or microorganism is typically prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea, coffee.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Conditions

The methods of the invention involve the measuring of a current passing through the pore during interaction with the nucleotide. Suitable conditions for measuring ionic currents through transmembrane protein pores are known in the art and disclosed in the Example. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 160 mV to 240 mV. It is possible to increase discrimination between different nucleotides by a pore of the invention by using an increased applied potential.

The methods are typically carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. The salt concentration is preferably from 150 mM to 1M. High salt concentrations provide a high signal to noise ratio and allow for currents indicative of the presence of a nucleotide to be identified against the background of normal current fluctuations. Lower salt concentrations may be used if nucleotide detection is carried out in the presence of an enzyme, such as when sequencing nucleic acids. This is discussed in more detail below.

The methods are typically carried out in the presence of a buffer. In the exemplary apparatus discussed above, the buffer is present in the aqueous solution in the chamber. Any buffer may be used in the method of the invention. One suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods are typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods may be carried out at room temperature. The methods are preferably carried out at a temperature that supports enzyme function, such as about 37° C.

Methods of Characterising Nucleic Acids

The present invention also provides methods of characterising a target nucleic acid sequence. One or more characteristics of the target nucleic acid sequence may be determined. The method may involve measuring two, three, four or five or more characteristics of the target nucleic acid sequence. The one or more characteristics are preferably selected from (i) the length of the target nucleic acid sequence, (ii) the identity of the target nucleic acid sequence, (iii) the sequence of the target nucleic acid sequence, (iv) the secondary structure of the target nucleic acid sequence and (v) whether or not the target nucleic acid sequence is modified. Any combination of (i) to (v) may be determined in accordance with the invention.

For (i), the length of the nucleic acid sequence may be measured using the number of interactions between the target nucleic acid sequence and the pore.

For (ii), the identity of the nucleic acid sequence may be measured in a number of ways. The identity of the nucleic acid sequence may be measured in conjunction with measurement of the sequence of the target nucleic acid sequence or without measurement of the sequence of the target nucleic acid sequence. The former is straightforward; the nucleic acid is sequenced and thereby identified. The latter may be done in several ways. For instance, the presence of a particular motif in the nucleic acid sequence may be measured (without measuring the remaining sequence of the polynucleotide). Alternatively, the measurement of a particular electrical signal in the method may identify the target nucleic acid sequence as coming from a particular source.

For (iii), the sequence of the nucleic acid sequence can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, the secondary structure may be measured using a change in dwell time or a change in current flowing through the pore.

The invention also provides a method of estimating the sequence of a target nucleic acid sequence. The invention further provides a method of sequencing a target nucleic acid sequence.

A nucleic acid is a macromolecule comprising two or more nucleotides. The nucleotides may be any of those discussed above.

In one embodiment, the method comprises (a) contacting the target sequence with a pore of the invention and a nucleic acid binding protein so that protein controls the movement of the target sequence through the pore and a proportion of the nucleotides in the target sequence interacts with the pore and (b) measuring the current passing through the pore during each interaction and thereby characterising, such as estimating the sequence of or sequencing, the target sequence. Hence, the method involves nanopore sensing of a proportion of the nucleotides in a target nucleic acid sequence as the nucleotides pass through the barrel or channel in order to characterising, such as sequencing, the target sequence.

In another embodiment, the method comprises (a) contacting the target sequence with a pore of the invention and an exonuclease such that the exonuclease digests an individual nucleotide from one end of the target sequence; (b) contacting the nucleotide with the pore so that the nucleotide interacts with the adaptor; (c) measuring the current passing through the pore during the interaction and thereby characterising the nucleotide; and (d) repeating steps (a) to (c) at the same end of the target sequence and thereby characterising of the target sequence. Hence, the method involves nanopore sensing of a proportion of the nucleotides in a target nucleic acid sequence in a successive manner in order to characterise the target sequence. In a preferred embodiment, the method concerns sequencing the target nucleic acid sequence and step (a) comprises determining the identity of the nucleotide. Individual nucleotides are described above.

The pores of the invention are particularly suited to these methods because they display improved nucleotide discrimination. In particular, they display an increased current range, which makes it easier to discriminate between different nucleotides, and a reduced variance of states, which increases the signal-to-noise ratio. In addition, in relation to the former embodiment, the number of nucleotides contributing to the current as the nucleic acid moves through the pore is decreased. This makes it easier to identify a direct relationship between the observed current as the nucleic acid moves through the pore and the nucleic acid sequence. The pores of the invention are preferably chemically modified with (1) a molecular adaptor and/or (2) the nucleic acid binding protein or exonuclease as discussed above.

The whole or only part of the target nucleic acid sequence may be characterised, such as sequenced, using this method. The nucleic acid sequence can be any length. For example, the nucleic acid sequence can be at least 10, at least 50, at least 100, at least 150, at least 200, at least 250, at least 300, at least 400 or at least 500 nucleotides in length. The nucleic acid sequence can be 1000 or more nucleotides or 5000 or more nucleotides in length. The nucleic acid sequence can be naturally occurring or artificial. For instance, the method may be used to verify the sequence of a manufactured oligonucleotide. The methods are typically carried out in vitro.

The methods may be carried out using any suitable membrane/pore system in which a pore is inserted into a membrane. The methods are typically carried out using any of the systems, apparatus or conditions disclosed above.

As mentioned above, good nucleotide discrimination can be achieved at low salt concentrations if the temperature is increased. In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

The target sequence being analysed can be combined with known protecting chemistries to protect the sequence from being acted upon by the binding protein or exonuclease while in the bulk solution. The pore can then be used to remove the protecting chemistry. This can be achieved either by using protecting groups that are unhybridised by the pore, binding protein or enzyme under an applied potential (WO 2008/124107) or by using protecting chemistries that are removed by the binding protein or enzyme when held in close proximity to the pore (J Am Chem Soc. 2010 Dec. 22; 132(50):17961-72).

Strand Sequencing

Strand sequencing involves the controlled and stepwise translocation of nucleic acid polymers through a pore. Pores of the invention can be used in strand sequencing. One method of the invention uses a nucleic acid binding protein to control the movement of the target sequence through the pore. Examples of such proteins include, but are not limited to, nucleic acid handling enzymes, such as nucleases, polymerases, topoisomerases, ligases and helicases, and non-catalytic binding proteins such as those classified by SCOP (Structural Classification of Proteins) under the Nucleic acid-binding protein superfamily (50249). The binding protein may be single strand binding protein (SSB).

A nucleic acid is a macromolecule comprising two or more nucleotides. The nucleic acid bound by the protein may comprise any combination of any nucleotides. The nucleotides may be any of those discussed above. The nucleic acid can be deoxyribonucleic acid (DNA) or ribonucleic acid (RNA). The nucleic acid may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The nucleic acid bound by the protein may be single stranded, such as cDNA, RNA, GNA, TNA or LNA, or double stranded, such as DNA. Proteins that bind single stranded nucleic acids may be used to sequence double stranded DNA as long as the double stranded DNA is dissociated into a single strand before it is bound by the protein.

The nucleic acid binding protein is preferably a nucleic acid handling enzyme. A nucleic acid handling enzyme is a polypeptide that is capable of interacting with and modifying at least one property of a nucleic acid. The enzyme may modify the nucleic acid by cleaving it to form individual nucleotides or shorter chains of nucleotides, such as di- or trinucleotides. The enzyme may modify the nucleic acid by orienting it or moving it to a specific position. The nucleic acid handling enzyme does not need to display enzymatic activity as long as it is capable of binding the target sequence and controlling its movement through the pore. For instance, the enzyme may be modified to remove its enzymatic activity or may be used under conditions which prevent it from acting as an enzyme. Such conditions are discussed in more detail below.

The nucleic acid handling enzyme is preferably derived from a nucleolytic enzyme. The nucleic acid handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 6), exonuclease III enzyme from *E. coli* (SEQ ID NO: 8), RecJ from *T. thermophilus* (SEQ ID NO: 10) and bacteriophage lambda exonuclease (SEQ ID NO: 12) and variants thereof. Three subunits comprising the sequence shown in SEQ ID NO: 10 or a variant thereof interact to form a trimer exonuclease. The enzyme is preferably based on Phi29 DNA polymerase (SEQ ID NO: 4).

A variant of SEQ ID NOs: 4, 6, 8, 10 or 12 is an enzyme that has an amino acid sequence which varies from that of SEQ ID NO: 4, 6, 8, 10 or 12 and which retains nucleic acid binding ability. The variant may include modifications that facilitate binding of the nucleic acid and/or facilitate its activity at high salt concentrations and/or room temperature.

Over the entire length of the amino acid sequence of SEQ ID NO: 4, 6, 8, 10 or 12, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4, 6, 8, 10 or 12 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to SEQ ID NO: 2. The enzyme may be covalently attached to the pore as discussed above.

The enzyme is not required to be in as close a proximity to the pore lumen as for individual nucleotide sequencing as there is no potential for disorder in the series in which nucleotides reach the sensing moiety of the pore.

The two strategies for single strand DNA sequencing are the translocation of the DNA through the nanopore, both cis to trans and trans to cis, either with or against an applied potential. The most advantageous mechanism for strand sequencing is the controlled translocation of single strand DNA through the nanopore under an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Exonuclease-Based Methods

In one embodiment, the method of characterising a target nucleic acid sequence involves contacting the target sequence with an exonuclease enzyme. Any of the exonuclease enzymes discussed above may be used in the method. The exonuclease releases individual nucleotides from one end of the target sequence. The enzyme may be covalently attached to the pore as discussed above.

Exonucleases are enzymes that typically latch onto one end of a nucleic acid sequence and digest the sequence one nucleotide at a time from that end. The exonuclease can digest the nucleic acid in the 5' to 3' direction or 3' to 5' direction. The end of the nucleic acid to which the exonuclease binds is typically determined through the choice of enzyme used and/or using methods known in the art. Hydroxyl groups or cap structures at either end of the nucleic acid sequence may typically be used to prevent or facilitate the binding of the exonuclease to a particular end of the nucleic acid sequence.

The method involves contacting the nucleic acid sequence with the exonuclease so that the nucleotides are digested from the end of the nucleic acid at a rate that allows characterisation or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of the invention involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

Msp and Phi29 DNA Polymerase

In a preferred embodiment, characterisation, such as strand sequencing, is carried out using a pore derived from Msp and a Phi29 DNA polymerase. The method comprises (a) contacting the target sequence with a pore derived from Msp and a Phi29 DNA polymerase such that the polymerase controls the movement of the target sequence through the pore and a proportion of the nucleotides in the target sequence interacts with the pore and (b) measuring the current passing through the pore during each interaction and thereby characterising, such as determining the sequence, of the target sequence, wherein steps (a) and (b) are carried out with a voltage applied across the pore. When the target sequence is contacted with a Phi29 DNA polymerase and a pore derived from Msp, the target sequence firstly forms a complex with the Phi29 DNA polymerase. When the voltage is applied across the pore, the target sequence/Phi29 DNA polymerase complex forms a complex with the pore and controls the movement of the target sequence through the pore.

This embodiment has three unexpected advantages. First, the target sequence moves through the pore at a rate that is commercially viable yet allows effective sequencing. The target sequence moves through the Msp pore more quickly than it does through a hemolysin pore. Second, an increased current range is observed as the nucleic acid moves through the pore allowing the sequence to be determined more easily. Third, a decreased current variance is observed when the specific pore and polymerase are used together thereby increasing the signal-to-noise ratio.

Any nucleic acid sequence described above may be characterised or sequenced. At least a portion of the nucleic acid sequence is preferably double stranded.

The pore may be any of the pores discussed above. The pore is preferably a pore of the invention. The pore may comprise eight monomers comprising the sequence shown in SEQ ID NO: 2, 16, 17 or 18 or a variant thereof. The pore does not have to include any of the mutations of the invention.

Wild-type Phi29 DNA polymerase has polymerase and exonuclease activity. It may also unzip double stranded nucleic acids under the correct conditions. Hence, the enzyme may work in three modes. This is discussed in more detail below.

The Phi29 DNA polymerase may comprise the sequence shown in SEQ ID NO: 4 or a variant thereof. A variant of SEQ ID NOs: 4 is an enzyme that has an amino acid sequence which varies from that of SEQ ID NO: 4 and which retains nucleic acid binding activity. The variant must work in at least one of the three modes discussed below. Preferably, the variant works in all three modes. The variant may include modifications that facilitate handling of the nucleic acid and/or facilitate its activity at high salt concentrations and/or room temperature.

Over the entire length of the amino acid sequence of SEQ ID NO: 4, a variant will preferably be at least 40% homologous to that sequence based on amino acid identity. More preferably, the variant polypeptide may be at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to SEQ ID NO: 2. The enzyme may be covalently attached to the pore as discussed above.

Any of the systems, apparatus or conditions discussed above may be used in accordance with this preferred embodiment. The salt concentration is typically from 0.15M to 0.6M. The salt is preferably KCl.

The method may be carried out in one of three preferred ways based on the three modes of the Phi29 DNA polymerase. Each way includes a method of proof reading the sequence. First, the method is preferably carried out using the Phi29 DNA polymerase as a polymerase. In this embodiment, steps (a) and (b) are carried out in the presence of free nucleotides and an enzyme cofactor such that the polymerase moves the target sequence through the pore against the field resulting from the applied voltage. The target sequence moves in the 5' to 3' direction. The free nucleotides may be one or more of any of the individual nucleotides discussed above. The enzyme cofactor is a factor that allows the Phi29 DNA polymerase to function either as a polymerase or an exonuclease. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$. The method preferably further comprises (c) removing the free nucleotides such that the polymerase moves the target sequence through the pore with the field resulting from the applied voltage (i.e. in the 3' and 5' direction) and a proportion of the nucleotides in the target sequence interacts with the pore and (d) measuring the current passing through the pore during each interaction and thereby proof reading the sequence of the target sequence obtained in step (b), wherein steps (c) and (d) are also carried out with a voltage applied across the pore.

Second, the method is preferably carried out using the Phi29 DNA polymerase as an exonuclease. In this embodiment, wherein steps (a) and (b) are carried out in the absence of free nucleotides and the presence of an enzyme cofactor such that the polymerase moves the target sequence through the pore with the field resulting from the applied voltage. The target sequence moves in the 3' to 5' direction. The method preferably further comprises (c) adding free nucleotides such that the polymerase moves the target sequence through the pore against the field resulting from the applied voltage (i.e. in the 5' to 3' direction) and a proportion of the nucleotides in the target sequence interacts with the pore and (d) measuring the current passing through the pore during each interaction and thereby proof reading the sequence of the target sequence obtained in step (b), wherein steps (c) and (d) are also carried out with a voltage applied across the pore.

Third, the method is preferably carried out using the Phi29 DNA polymerase in unzipping mode. In this embodiment, steps (a) and (b) are carried out in the absence of free nucleotides and the absence of an enzyme cofactor such that the polymerase controls the movement of the target sequence through the pore with the field resulting from the applied voltage (as it is unzipped). In this embodiment, the polymerase acts like a brake preventing the target sequence from moving through the pore too quickly under the influence of the applied voltage. The method preferably further comprises (c) lowering the voltage applied across the pore such that the target sequence moves through the pore in the opposite direction to that in steps (a) and (b) (i.e. as it re-anneals) and a proportion of the nucleotides in the target sequence interacts with the pore and (d) measuring the current passing through the pore during each interaction and thereby proof reading the sequence of the target sequence obtained in step (b), wherein steps (c) and (d) are also carried out with a voltage applied across the pore.

The invention also provides a method of forming a sensor for sequencing a target nucleic acid sequence, comprising (a) contacting a pore derived from Msp with a Phi29 DNA polymerase in the presence of the target nucleic acid sequence and (b) applying a voltage across the pore to form a complex between the pore and the polymerase and thereby forming a sensor for sequencing the target nucleic acid sequence. The invention further provides a method of increasing the rate of activity of a Phi29 DNA polymerase, comprising contacting the Phi29 DNA polymerase with a pore derived from Msp in the presence of a nucleic acid sequence and applying a voltage across the pore to form a complex between the pore and the polymerase and thereby increasing the rate of activity of a Phi29 DNA polymerase.

Kits

The present invention also provides kits for characterising, such as sequencing, a target nucleic acid sequence. One kit comprises (a) a pore of the invention and (b) a nucleic acid handling enzyme. Another kit comprises (a) a pore derived from Msp and (b) a Phi29 DNA polymerase. Any of the embodiments discussed above with reference to the methods of the invention are equally applicable to the kits of the invention.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotide sequences, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising, such as sequencing, target nucleic acid sequences in a sample. The apparatus may comprise (a) a plurality of pores of the invention and (b) a plurality of nucleic acid handling enzymes. Alternatively, the invention may comprise a plurality of pores derived from Msp and a plurality of Phi29 DNA polymerases. The apparatus may be any conventional apparatus for analyte analysis, such as an array or a chip.

The apparatus preferably comprises:
- a sensor device that is capable of supporting the plurality of pores and being operable to perform nucleic acid characterising or sequencing using the pores and enzymes;
- at least one reservoir for holding material for performing the characterising or sequencing;
- a fluidics system configured to controllably supply material from the at least one reservoir to the sensor device; and
- a plurality of containers for receiving respective samples, the fluidics system being configured to supply the samples selectively from the containers to the sensor device. The apparatus may be any of those described in International Application No. PCT/GB10/000789 (published as WO 2010/122293), International Application No. PCT/GB10/002206 (not yet published) or International Application No. PCT/US99/25679 (published as WO 00/28312).

The following Examples illustrate the invention:

Example 1

Homo-oligomers are pores where all the monomer units are identical. As the monomer units will self-assemble, these are the simplest constructs to produce. Our strategies for improving the base reader properties can be split into categories:
- Sterics (increasing or decreasing the size of amino acid residues)
- Charge (introducing +ve charge to interact with DNA)
- Hydrogen bonding (residues that can hydrogen bond to the base pairs)
- Pi Stacking (amino acids that interact through delocalised electron pi systems)

Increase Sterics/Pi Stacking (all NNN-RRK Background):
Sterics—substitution for residues with bulk (e.g. Phenylalanine, Tryptophan, Tyrosine, Histidine)
Pi Stacking—substitution for aromatic residues (e.g. Phenylalanine, Tryptophan, Tyrosine, Histidine)
In all the following tables (6-11), the mutations made to SEQ ID NO: 2 are shown. B1=SEQ ID NO: 2.

TABLE 6

| | |
|---|---|
| MS-(B1-D91Y)$_8$ | Bulky Tyrosine at the constriction. |
| MS-(B1-D90G/D91Y)$_8$ | Bulky Tyrosine at the constriction, reduced barrel. |
| MS-(B1-D90Y/D91G)$_8$ | Bulky Tyrosine at the constriction, reduced barrel. |
| MS-(B1-I05Y)$_8$ | Mutation just above barrel to increase size. |

Decreased Sterics—substitution for residues with smaller size (e.g. Serine, Threonine, Glycine, Alanine, Valine)

TABLE 7

| | |
|---|---|
| MS-(B1-D90G/D91G)$_8$ | Reduction of sterics in the barrel. |
| MS-(B1-I05A)$_8$ | Mutation just above barrel to reduce size. |
| MS-(B1-I05G)$_8$ | Mutation just above barrel to reduce size. |

Charge—substitution for residues with positive charge (e.g. Arginine, Lysine, Histidine)

TABLE 8

| | |
|---|---|
| MS-(B1-D90R)$_8$ | Charged Arginine at the constriction. |
| MS-(B1-D91R)$_8$ | Charged Arginine at the constriction. |
| MS-(B1-D90R/D91R)$_8$ | Double Arginine at the constriction. |
| MS-(B1-D90K)$_8$ | Charged Lysine at the constriction. |
| MS-(B1-D91K)$_8$ | Charged Lysine at the constriction. |
| MS-(B1-D90K/D91K)$_8$ | Double Lysine at the constriction. |

Hydrogen Bonding—substitution for residues with-bonding capacity (e.g. Asparagine, Glutamine, Tyrosine, Histidine)

TABLE 9

| | |
|---|---|
| MS-(B1-D90Q)$_8$ | Glutamine at the constriction. |
| MS-(B1-D91Q)$_8$ | Glutamine at the constriction. |
| MS-(B1-D90Q/D91G)$_8$ | Glutamine at the constriction, size reduction. |
| MS-(B1-D90G/D91Q)$_8$ | Glutamine at the constriction, size reduction. |
| MS-(B1-D90Q/D91Q)$_8$ | Double Glutamine at the constriction. |

TABLE 10

| | |
|---|---|
| MS-(B1-D118N)$_8$ | Removal of the charge in the middle of the lumen. |
| MS-(B1-D118A)$_8$ | Removal of the charge in the middle of the lumen. |

Homo-oligomers can also be modified to contain reactive group, which can then be chemically modified.

TABLE 11

| | |
|---|---|
| MS-(B1-D91C)$_8$ | Addition of Cysteine at the barrel. |
| MS-(B1-D90C) | Addition of Cysteine at the barrel. |

Example 2

Different monomer units can be combined to create novel oligomer pores. When the oligomer contains more than one different subunit (e.g. MS-(MutA)$_6$(MutB)$_1$(MutC)$_1$), the pore is a hetero-oligomer. Hetero-oligomers typically only have one unit modified (e.g. MS-(MutA)$_7$(MutB)$_1$). Other ratios of hetero-oligomers could also be formed (e.g. MS-(MutA)$_6$(MutB)$_2$). Subunits may also include SEQ ID NO: 2.

The advantage of hetero-oligomers is that a single chemical change can be made to the pore (rather than introducing a change to every monomer-unit). This is a less drastic change to the structure than a homo-oligomer and may allow residues to be introduced into the pore at a position which did not work for a homo-oligomer. A single residue interacting with the DNA may be beneficial compared to multiple units (e.g. a single Arg on a hetero-octamer, compared to eight Arg on an octamer). Mutants can also be combine to produce different effects at the same residue, an example of this would be to reduce the size of seven units, while increasing the size of one (e.g. MS-(D90G)$_8$(D90Y)$_1$).

Mutant design rules will be similar to those presented above for homo-oligomers.

Introduction of a Single Steric Residue

TABLE 12

| | |
|---|---|
| MS-(B1)$_7$(B1-D90Y)$_1$ | Addition of single Tyrosine in the barrel. |

TABLE 12-continued

| | |
|---|---|
| MS-(B1)$_7$(B1-D91Y)$_1$ | Addition of single Tyrosine in the barrel. |
| MS-(B1)$_7$(B1-D90W)$_1$ | Addition of single Tryptophan in the barrel. |
| MS-(B1)$_7$(B1-D91W)$_1$ | Addition of single Tryptophan in the barrel. |

Introduction of a Single Charged Residue

TABLE 13

| | |
|---|---|
| MS-(B1)$_7$(B1-D90K)$_1$ | Addition of single Lysine in the barrel. |
| MS-(B1)$_7$(B1-D91K)$_1$ | Addition of single Lysine in the barrel. |
| MS-(B1)$_7$(B1-D90R)$_1$ | Addition of single Arginine in the barrel. |
| MS-(B1)$_7$(B1-D91R)$_1$ | Addition of single Arginine in the barrel. |

Introduction of a Single Reactive Residue

TABLE 14

| | |
|---|---|
| MS-(B1)$_7$(B1-D90C)$_1$ | Addition of single Cysteine in the barrel. |
| MS-(B1)$_7$(B1-D91C)$_1$ | Addition of single Cysteine in the barrel. |

Example 3

Introduction of a Single Reactive Residue for Chemical Modification.

TABLE 15

| | |
|---|---|
| MS-(B1)$_7$(B1-D90C)$_1$ | Addition of single Cysteine in the barrel. |
| MS-(B1)$_7$(B1-D118C)$_1$ | Addition of single Cysteine in the lumen. |
| MS-(B1)$_7$(B1-G54C)$_1$ | Addition of single Cysteine for nucleic acid binding protein attachment. |

Example 4

The following Tables summarize the mutant pores of the invention. The first concerns homo-oligomers and the second concerns hetero-oligomers.

TABLE 16

| Design_type_name | Mutant_Short | Mutant_full |
|---|---|---|
| Mutant (Homo) | MS-(B1)8 | MS-(D90N/D91N/D93N/D118R/D134R/E139K)8 |
| Mutant (Homo) | MS-(B1-D90Y)8 | MS-(D90Y/D91N/D93N/D118R/D134R/E139K)8 |
| Mutant (Homo) | MS-(B1-D90R)8 | MS-(D90R/D91N/D93N/D118R/D134R/E139K)8 |
| Mutant (Homo) | MS-(B1-D90K)8 | MS-(D90K/D91N/D93N/D118R/D134R/E139K)8 |
| Mutant (Homo) | MS-(B1-D118N)8 | MS-(D90N/D91N/D93N/D118N/D134R/E139K)8 |
| Mutant (Homo) | MS-(B1-D90Q)8 | MS-(D90Q/D91N/D93N/D118R/D134R/E139K)8 |
| Mutant (Homo) | MS-(B1-D91Q)8 | MS-(D90N/D91Q/D93N/D118R/D134R/E139K)8 |
| Mutant (Homo) | MS-(B1-D91Y)8 | MS-(D90N/D91Y/D93N/D118R/D134R/E139K)8 |
| Mutant (Homo) | MS-(B1-D90G/D91Y)8 | MS-(D90G/D91Y/D93N/D118R/D134R/E139K)8 |
| Mutant (Homo) | MS-(B1-D91R)8 | MS-(D90N/D91R/D93N/D118R/D134R/E139K)8 |
| Mutant (Homo) | MS-(B1-D90R/D91R)8 | MS-(D90R/D91R/D93N/D118R/D134R/E139K)8 |
| Mutant (Homo) | MS-(B1-D91K)8 | MS-(D90N/D91K/D93N/D118R/D134R/E139K)8 |
| Mutant (Homo) | MS-(B1-D90K/D91K)8 | MS-(D90K/D91K/D93N/D118R/D134R/E139K)8 |
| Mutant (Homo) | MS-(B1-I105A)8 | MS-(D90N/D91N/D93N/I105A/D118R/D134R/E139K)8 |
| Mutant (Homo) | MS-(B1-I105G)8 | MS-(D90N/D91N/D93N/I105G/D118R/D134R/E139K)8 |
| Mutant (Homo) | MS-(B1-I105Y)8 | MS-(D90N/D91N/D93N/I105Y/D118R/D134R/E139K)8 |
| Mutant (Homo) | MS-(B1-I105N)8 | MS-(D90N/D91N/D93N/I105N/D118R/D134R/E139K)8 |
| Chemical (Homo) | MS-(B1-D91C)8 | MS-(D90N/D91C/D93N/D118R/D134R/E139K)8 |
| Chemical (Homo) | MS-(B1-D90C)8 | MS-(D90C/D91N/D93N/D118R/D134R/E139K)8 |
| Mutant (Homo) | MS-(B1-D90Y/D91G)8 | MS-(D90Y/D91G/D93N/D118R/D134R/E139K)8 |
| Mutant (Homo) | MS-(B1-D90G/D91G)8 | MS-(D90G/D91G/D93N/D118R/D134R/E139K)8 |
| Mutant (Homo) | MS-(B1-D90G/D93G)8 | MS-(D90G/D91N/D93G/D118R/D134R/E139K)8 |
| Mutant (Homo) | MS-(B1-D90G)8 | MS-(D90G/D91N/D93N/D118R/D134R/E139K)8 |
| Mutant (Homo) | MS-(B1-D91G)8 | MS-(D90N/D91G/D93N/D118R/D134R/E139K)8 |
| Mutant (Homo) | MS-(B1-D93G)8 | MS-(D90N/D91N/D93G/D118R/D134R/E139K)8 |
| Mutant (Homo) | MS-(B1-D90G/D91A)8 | MS-(D90G/D91A/D93N/D118R/D134R/E139K)8 |
| Mutant (Homo) | MS-(B1-D90S)8 | MS-(D90S/D91N/D93N/D118R/D134R/E139K)8 |
| Mutant (Homo) | MS-(B1-D91S)8 | MS-(D90N/D91S/D93N/D118R/D134R/E139K)8 |
| Mutant (Homo) | MS-(B1-D90S/D91S)8 | MS-(D90S/D91S/D93N/D118R/D134R/E139K)8 |
| Mutant (Homo) | MS-(B1-I105K)8 | MS-(D90N/D91N/D93N/I105K/D118R/D134R/E139K)8 |
| Mutant (Homo) | MS-(B1-I105R)8 | MS-(D90N/D91N/D93N/I105R/D118R/D134R/E139K)8 |
| Mutant (Homo) | MS-(B1-I105V)8 | MS-(D90N/D91N/D93N/I105V/D118R/D134R/E139K)8 |
| Mutant (Homo) | MS-(B1-I105L)8 | MS-(D90N/D91N/D93N/I105L/D118R/D134R/E139K)8 |
| Mutant (Homo) | MS-(B1-I105P)8 | MS-(D90N/D91N/D93N/I105P/D118R/D134R/E139K)8 |
| Mutant (Homo) | MS-(B1-I105W)8 | MS-(D90N/D91N/D93N/I105W/D118R/D134R/E139K)8 |

TABLE 16-continued

| Design_type_name | Mutant_Short | Mutant_full |
|---|---|---|
| Mutant (Homo) | MS-(B1-I105S)8 | MS-(D90N/D91N/D93N/I105S/D118R/D134R/E139K)8 |
| Mutant (Homo) | MS-(B1-I105T)8 | MS-(D90N/D91N/D93N/I105T/D118R/D134R/E139K)8 |
| Mutant (Homo) | MS-(B1-I105Q)8 | MS-(D90N/D91N/D93N/I105Q/D118R/D134R/E139K)8 |
| Mutant (Homo) | MS-(B1-L88R)8 | MS-(L88R/D90N/D91N/D93N/D118R/D134R/E139K)8 |
| Mutant (Homo) | MS-(B1-L88A)8 | MS-(L88A/D90N/D91N/D93N/D118R/D134R/E139K)8 |
| Mutant (Homo) | MS-(B1-L88Y)8 | MS-(L88Y/D90N/D91N/D93N/D118R/D134R/E139K)8 |
| Mutant (Homo) | MS-(B1-L88G)8 | MS-(L88G/D90N/D91N/D93N/D118R/D134R/E139K)8 |
| Mutant (Homo) | MS-(B1-L88N)8 | MS-(L88N/D90N/D91N/D93N/D118R/D134R/E139K)8 |
| Mutant (Homo) | MS-(B1-L88Q)8 | MS-(L88Q/D90N/D91N/D93N/D118R/D134R/E139K)8 |
| Mutant (Homo) | MS-(B1-D90Y/I105A)8 | MS-(D90Y/D91N/D93N/I105A/D118R/D134R/E139K)8 |
| Mutant (Homo) | MS-(B1-D90G/I105A)8 | MS-(D90G/D91N/D93N/I105A/D118R/D134R/E139K)8 |
| Mutant (Homo) | MS-(B1-D90Q/I105A)8 | MS-(D90Q/D91N/D93N/I105A/D118R/D134R/E139K)8 |
| Mutant (Homo) | MS-(B1-D90R/I105A)8 | MS-(D90R/D91N/D93N/I105A/D118R/D134R/E139K)8 |
| Mutant (Homo) | MS-(B1-D90S/I105A)8 | MS-(D90S/D91N/D93N/I105A/D118R/D134R/E139K)8 |
| Mutant (Homo) | MS-(B1-L88A/I105A)8 | MS-(L88A/D90N/D91N/D93N/I105A/D118R/D134R/E139K)8 |
| Mutant (Homo) | MS-(B1-L88S/I105S)8 | MS-(L88S/D90N/D91N/D93N/I105S/D118R/D134R/E139K)8 |
| Mutant (Homo) | MS-(B1-L88N/I105N)8 | MS-(L88N/D90N/D91N/D93N/I105N/D118R/D134R/E139K)8 |

TABLE 17

| Design_type | Mutant_Short | Mutant_full |
|---|---|---|
| Mutant (Hetero) | MS-(B1)7(B1-D90K)1 | MS-(D90N/D91N/D93N/D118R/D134R/E139K)7(D90K/D91N/D93N/D118R/D134R/E139K)1 |
| Mutant (Hetero) | MS-(B1)7(B1-D90R)1 | MS-(D90N/D91N/D93N/D118R/D134R/E139K)7(D90R/D91N/D93N/D118R/D134R/E139K)1 |
| Mutant (Hetero) | MS-(B1)7(B1-D90Y)1 | MS-(D90N/D91N/D93N/D118R/D134R/E139K)7(D90Y/D91N/D93N/D118R/D134R/E139K)1 |
| Mutant (Hetero) | MS-(B1)7(B1-D90Q)1 | MS-(D90N/D91N/D93N/D118R/D134R/E139K)7(D90Q/D91N/D93N/D118R/D134R/E139K)1 |
| Mutant (Hetero) | MS-(B1)7(B1-D91Q)1 | MS-(D90N/D91N/D93N/D118R/D134R/E139K)7(D90N/D91Q/D93N/D118R/D134R/E139K)1 |
| Mutant (Hetero) | MS-(B1)7(B1-D91K)1 | MS-(D90N/D91N/D93N/D118R/D134R/E139K)7(D90N/D91K/D93N/D118R/D134R/E139K)1 |
| Mutant (Hetero) | MS-(B1)7(B1-D91R)1 | MS-(D90N/D91N/D93N/D118R/D134R/E139K)7(D90N/D91R/D93N/D118R/D134R/E139K)1 |
| Mutant (Hetero) | MS-(B1)7(B1-D91Y)1 | MS-(D90N/D91N/D93N/D118R/D134R/E139K)7(D90N/D91Y/D93N/D118R/D134R/E139K)1 |
| Mutant (Hetero) | MS-(B1)7(B1-D90W)1 | MS-(D90N/D91N/D93N/D118R/D134R/E139K)7(D90W/D91N/D93N/D118R/D134R/E139K)1 |
| Mutant (Hetero) | MS-(B1)7(B1-D91W)1 | MS-(D90N/D91N/D93N/D118R/D134R/E139K)7(D90N/D91W/D93N/D118R/D134R/E139K)1 |
| Chemical (Hetero) | MS-(B1)7(B1-D90C)1 | MS-(D90N/D91N/D93N/D118R/D134R/E139K)7(D90C/D91N/D93N/D118R/D134R/E139K)1 |
| Chemical (Hetero) | MS-(B1)7(B1-D91C)1 | MS-(D90N/D91N/D93N/D118R/D134R/E139K)7(D90N/D91C/D93N/D118R/D134R/E139K)1 |
| Chemical (Hetero) | MS-(B1)7(B1-L88C)1 | MS-(D90N/D91N/D93N/D118R/D134R/E139K)7(D90N/D91C/D93N/D118R/D134R/E139K)1 |
| Chemical (Hetero) | MS-(B1)7(B1-S103C)1 | MS-(D90N/D91N/D93N/D118R/D134R/E139K)7(D90N/D91C/D93N/D118R/D134R/E139K)1 |
| Chemical (Hetero) | MS-(B1)7(B1-I105C)1 | MS-(D90N/D91N/D93N/D118R/D134R/E139K)7(D90N/D91C/D93N/D118R/D134R/E139K)1 |

Example 5—MspA Compared with HL

We have combined Phi29 DNA polymerase (DNAP) as a molecular motor with a mutant MspA nanopore to allow controlled movement of a DNA strand through the pore. A voltage was applied across the pore and a current was generated from the movement of ions in a salt solution on either side of the nanopore. As the DNA moved through the pore, the ionic flow through the pore changed with respect to the DNA. This information has been shown to be sequence dependent.

We compared a mutant form of hemolysin with MspA, in particular MS-(B1)$_8$. The current range is higher for MspA compared with hemolysin (HL). In addition, the current range is also larger for MspA when a strand of DNA is threaded into the pore.

We have shown that there are a number of surprising features with MspA that were not anticipated by bringing the MspA and the Phi29 DNAP together. The main differences are:

1. Faster strand movement (Unzipping mode) compared to HL.
2. Increase current range when moving a strand through the pore.
3. Decreased variance of the current levels compared to HL mutants.

Faster Strand Movement

A 134mer ssDNA template (SEQ ID NO: 13) was hybridised to a 84mer ssDNA (SEQ ID NO: 14) to form a 84mer dsDNA template with a 50mer ssDNA 5' overhang. This strand moved through the MS-(B1)$_8$ MspA mutant and the hemolysin mutant using Phi29 DNAP in Unzipping mode. Two runs were acquired; one at 400 mM KCl and the other 600 mM KCl, all at room temperature with 10 mM Hepes, pH 8.0, 1 mM EDTA, 1 mM DTT. The applied potential was optimised for each mutant construct; HL was ran at 220 mV and the MspA at 180 mV.

Current levels were extracted as events from the DNA in the enzyme bound state these events were indexed and the current level, duration and variance of the event recorded.

For all the unzipping runs, the speed of unzipping was not consistent through the strand. This can be shown by calculating the average of the event duration, split by quarters of event index (FIG. 1). The first quarter provided events that had a much longer duration that the following quarters, this was true for both HL and MspA. For the first quarter, the average event length was shortest for MspA at 400 mM KCl and shortest for HL at 600 mM. However, in Q2, Q3 and Q4, the MspA produced shorter events for both salt conditions. Assuming the signal to noise is sufficient, short events are desirable as they indicate a rapid movement of the DNA strand through the pore, thus increasing the experimental throughput.

Increased Current Range and Reduced Variance

In the nanopore experiments described here, the current levels are mainly dependent on the salt concentration, the applied voltage, and temperature. The HL and the MS-(B1)$_8$ MspA mutants were compared in Unzipping mode using Phi29 DNA polymerase with set physical conditions of: 600 mM KCl, 10 mM Hepes, 1 mM EDTA, 1 mM DTT, pH 8.0, +220 mV. The DNA used in this experiment was a 100mer hairpin with a 34mer single stranded 5' overhang (SEQ ID NO: 15). The runs were conducted at room temperature.

Figure 2:
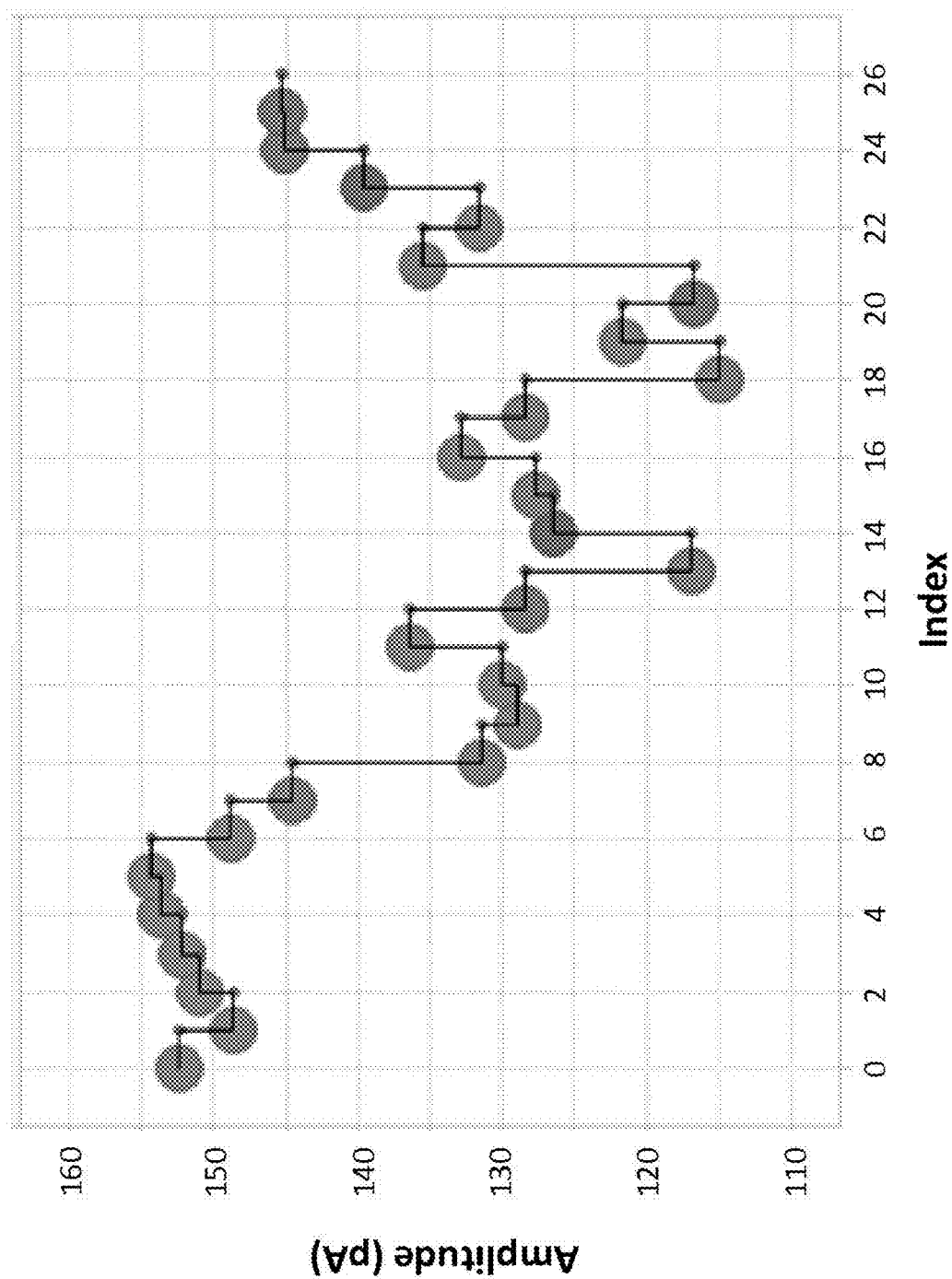
FIG. 2 shows current levels and variance obtained from using Phi29 in Unzipping mode to move a DNA strand (SEQ ID NO: 15) through the MS-(NNNRRK)$_8$ nanopore.
Figure 3:
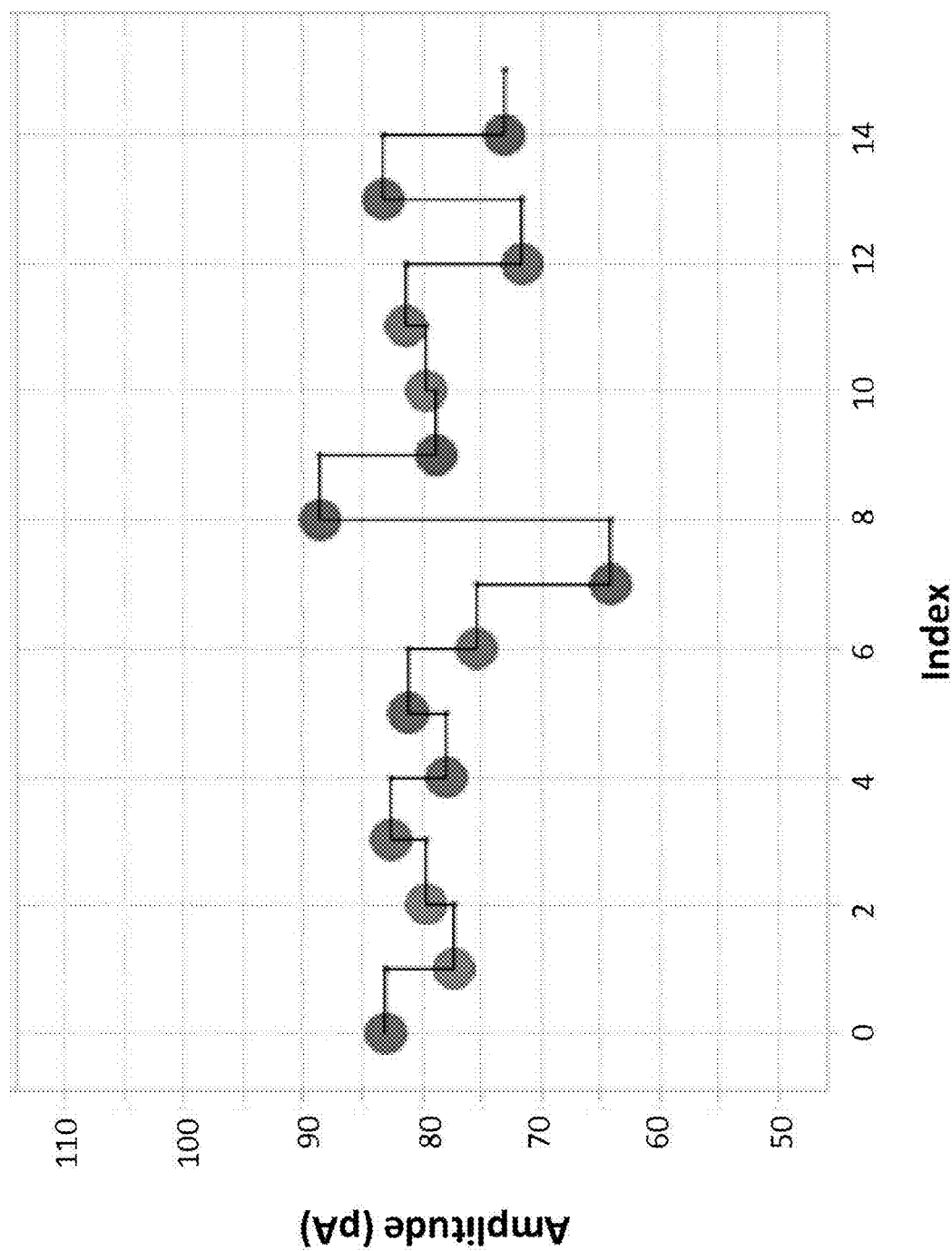
FIG. 3 shows current levels and variance obtained from using Phi29 in Unzipping mode to move a DNA strand (SEQ ID NO: 15) through the HL-(mutant)$_7$ nanopore.

Current levels were extracted as events from the DNA in the enzyme bound state these events were indexed and the current level, duration and variance of the event recorded (FIGS. 2 and 3).

It is clear from these experiments, that the MspA mutant gives a significantly larger current range of approximately 50 pA compared with the HL mutant where the range is approximately 20 pA (FIGS. 2 and 3). A large current range is advantageous as it will provide a greater signal to noise and make it easier to distinguish distinct current states. This is of particular benefit for sequencing applications, when N bases may contribute to the current signal, leading to $4^N$ possible current states.

The variance of the states is also reduced for the MspA mutant compared to the HL. This is shown by the standard deviation of the events in the traces above (FIGS. 2 and 3). For the strands above, the average of the standard deviation across all events for the MspA strand was 3.6 compared to 4.5 for HL. Low variance of states is desirable to allow accurate estimations of the event current level.

Example 6—Open Pore Current Comparison of the MS-(B1)8 Baseline to the MS-(B1-I105)8 Mutants The current levels of MspA pores can be controlled by mutating the I105 position in the protein. We demonstrate that the open pore current can be increased by over 80% as a result of making a single mutation to the MspA monomer.

Figure 4:
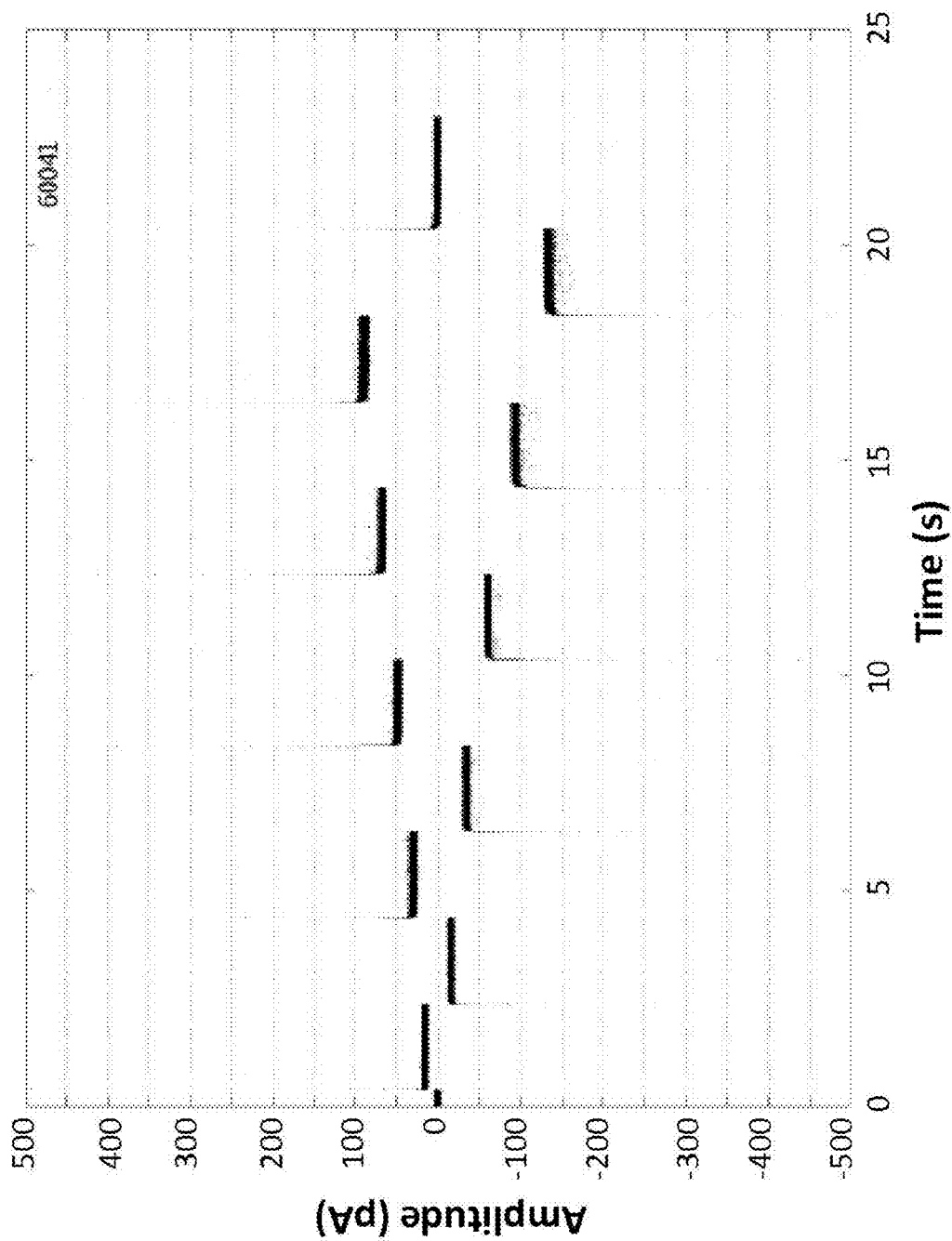
FIG. 4 shows the current levels for a single MspA channel recorded at a range of applied potentials (−200 mV to 200 mV).

Single channels were inserted into a lipid membrane under the following conditions: 400 mM KCl, 10 mM Hepes, pH 8.0, room temperature. The open pore current level was recorded over a range of applied potentials from −200 mV to 200 mV to produce an IV curve. The experiment was repeated for a number of pores to assess the distribution of the sample. An example of the data from an IV curve run can be seen (FIG. 4).

Figure 5:
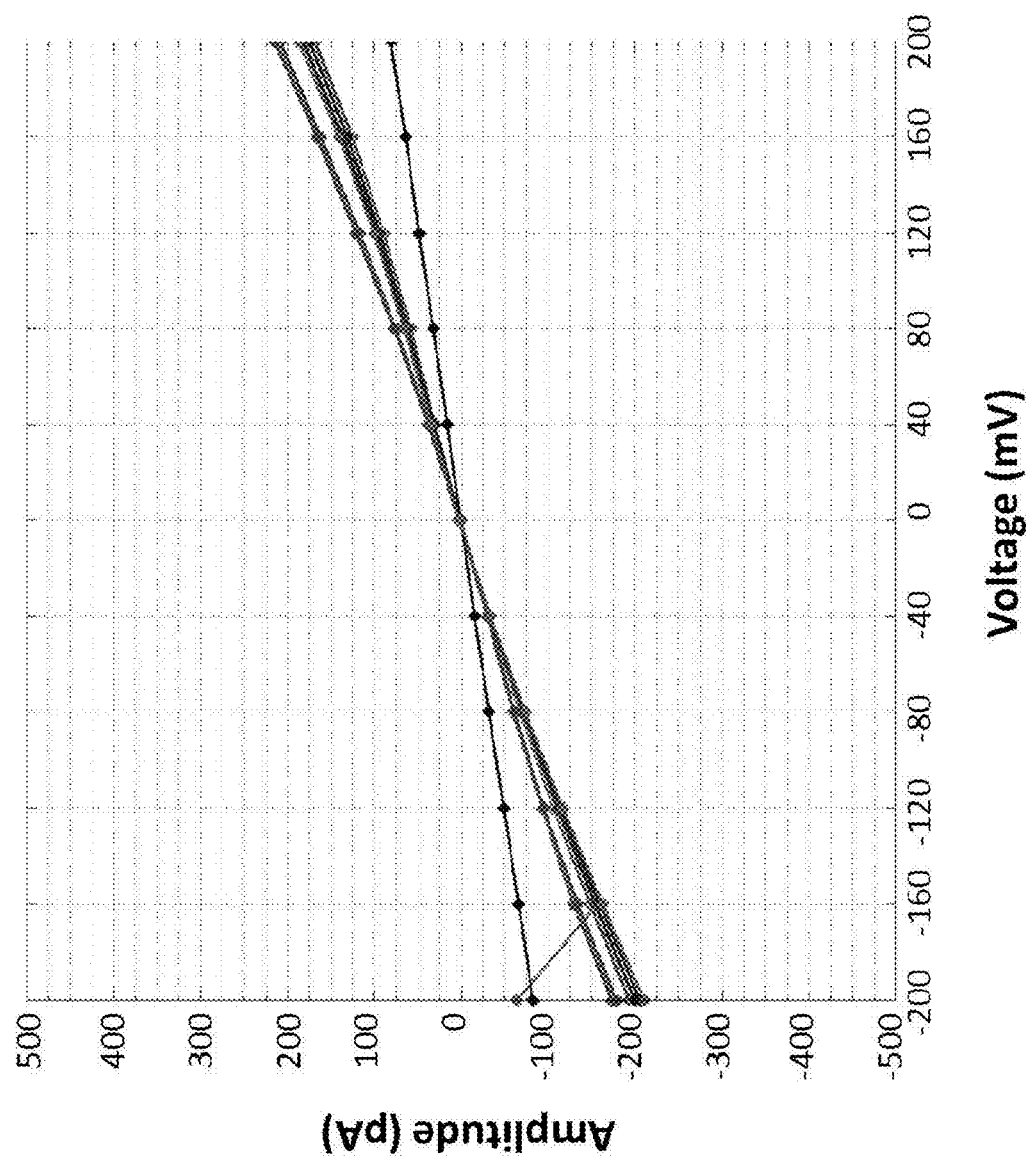
FIG. 5 shows the IV curve of open pore levels for the baseline MspA mutant, MS-(B1)8. Each line represents a single pore.

In our experiments, the baseline MS-(B1)8 mutant produces pore that have an open pore current of approximately 150 pA at +160 mV (FIG. 5).

Figure 6:
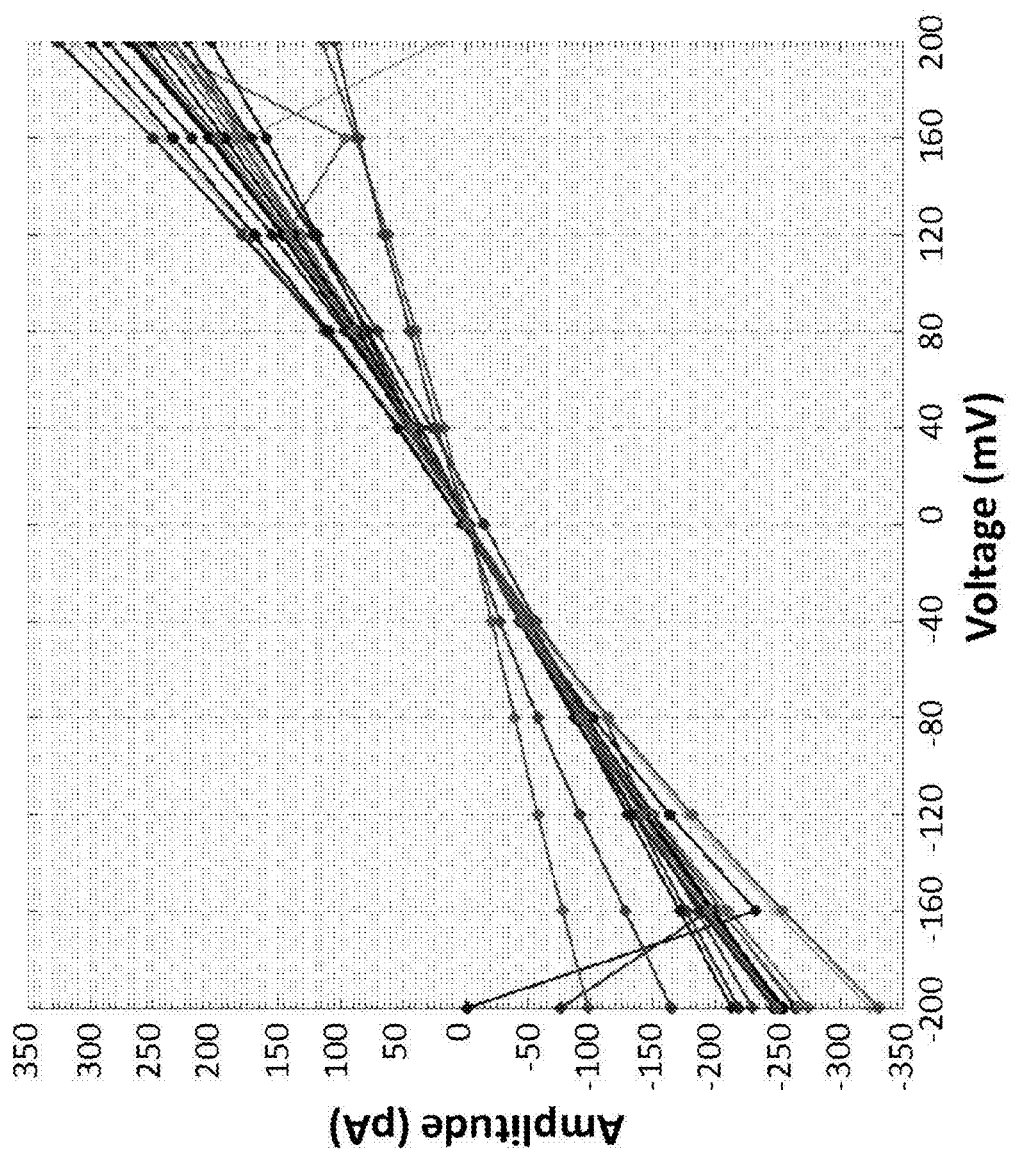
FIG. 6 shows the IV curve of open pore levels for the MspA mutant, MS-(B1-I105Y)8. Each line represents a single pore.

The experiment was repeated with the MS-(B1-I105Y)8 mutant which exhibited a large number of pores with a higher residual current. For these channels, the open pore current was approximately 200 pA at +160 mV (FIG. 6).

Figure 7:
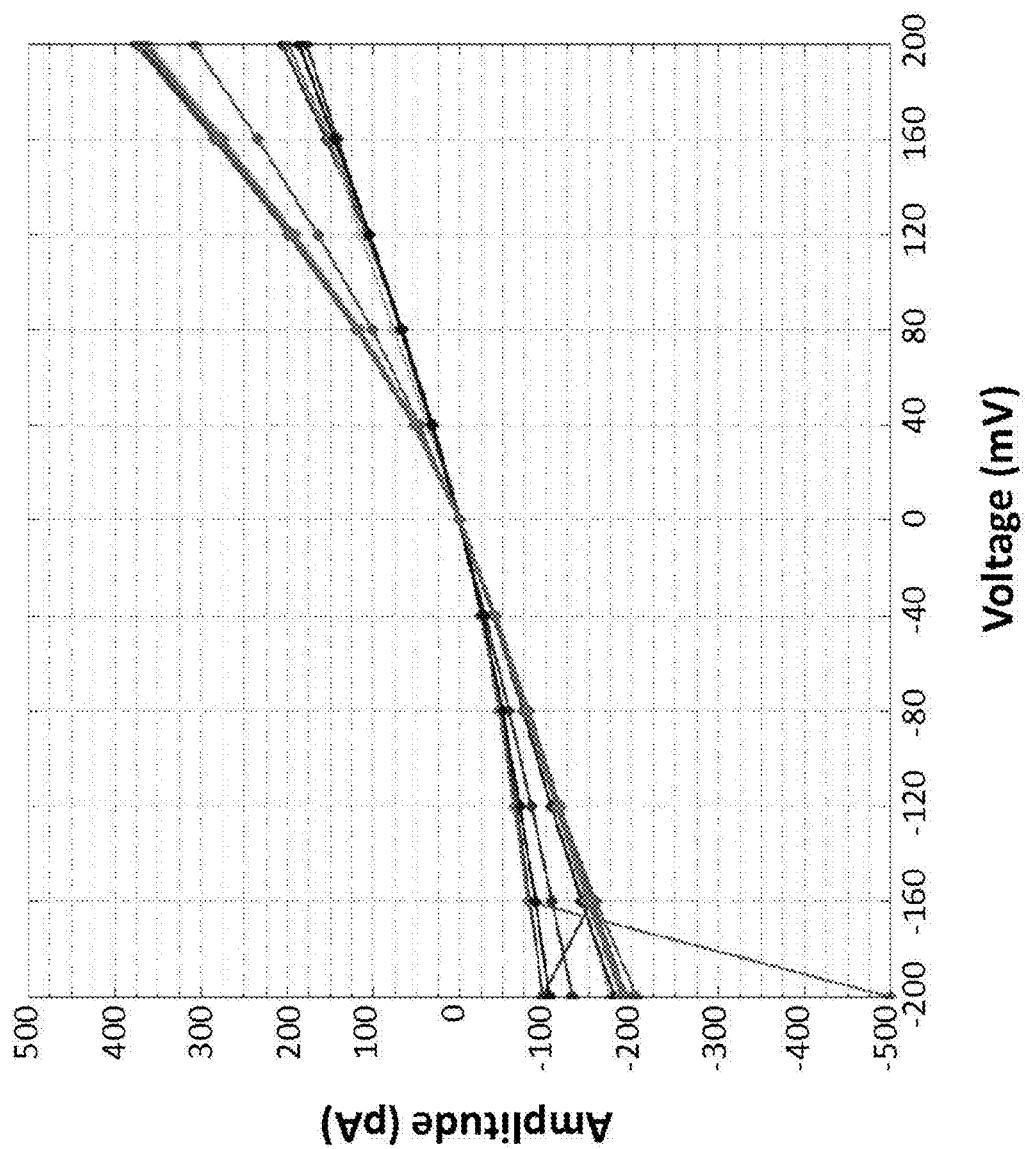
FIG. 7 shows the IV curve of open pore levels for the MspA mutant, MS-(B1-I105N)8. Each line represents a single pore.

The experiment was repeated with the MS-(B1-I105N)8 mutant which exhibited two main distributions of current levels. Ten out of sixteen pores gave a higher residual current in a tight distribution. For these channels, the open pore current was approximately 280 pA at +160 mV (FIG. 7).

Example 7—a MS-(B1-I105A)8 Pore that Spontaneously Changes Conductance

MspA mutant pores have been observed to spontaneously change conductance during electrical recording experiments.

Electrical measurements were acquired as described in example 6, using the MS-(B1-I105A)8 mutant pore.

Figure 8:
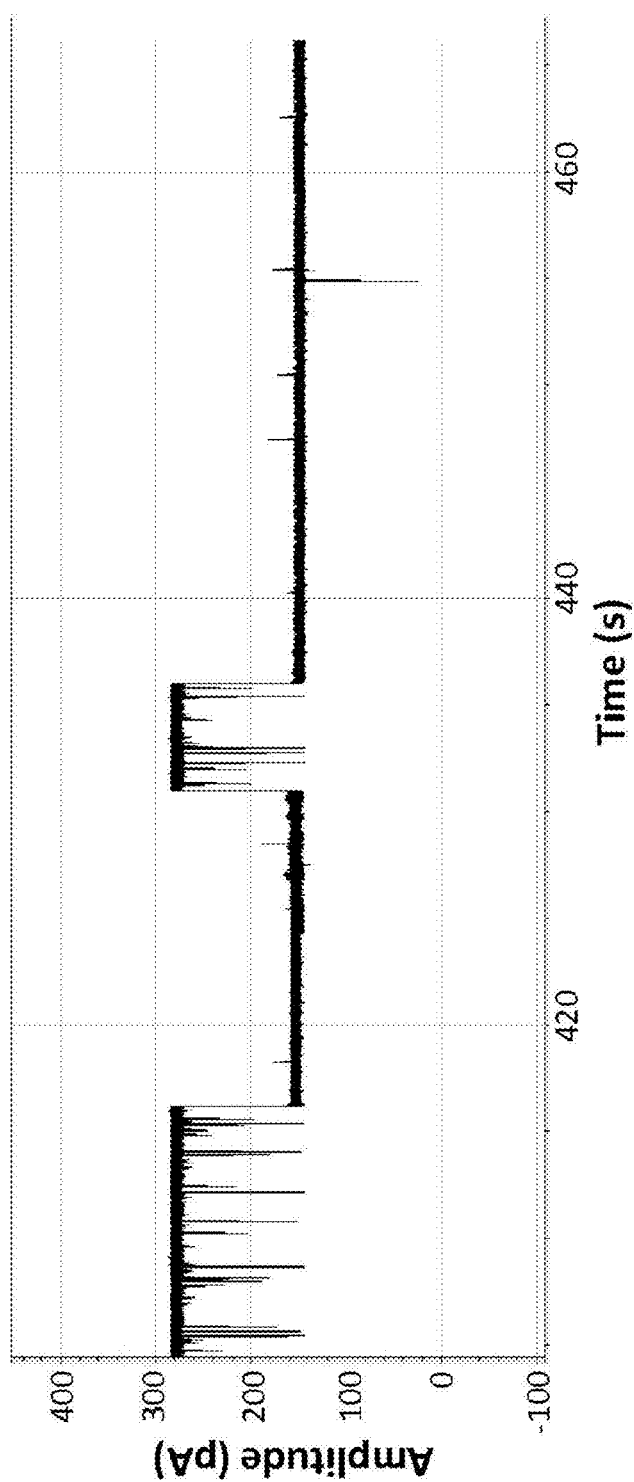
FIG. 8 shows the change in current between a high conductance state (275 pA) and a low conductance state (150 pA) for the MS-(B1-I105A)8 pore at 180 mV.

A single MspA mutant pore is capable of interchanging between high and low conductance states spontaneously (FIG. 8). This suggests that the mutations to the MspA allow conformational changes that are rarely observed in the baseline MS-(B1)8 pore. It is possible that mutations at the I105 position stabilise the high conductance state of the pore.

Example 8—Comparison DNA Currents when Moving DNA Through the Baseline MS-(B1)8 Pores Compared to the MS-(B1-I105A)8 Pores The MS-(B1)$_8$ pore and the MS-(B1-I105N)$_8$ pores were compared in unzipping mode using Phi29 DNA polymerase with set physical conditions of: 400 mM KCl, 10 mM Hepes, 1 mM EDTA, 1 mM DTT, pH 8.0, +180 mV. The DNA used in this experiment was a 100mer hairpin with a 34mer single stranded 5' overhang (SEQ ID NO: 15). The runs were conducted at room temperature.

Current levels were extracted as events from the DNA in the enzyme bound state these events were indexed and the current level, duration and variance of the event recorded.

Figure 9:
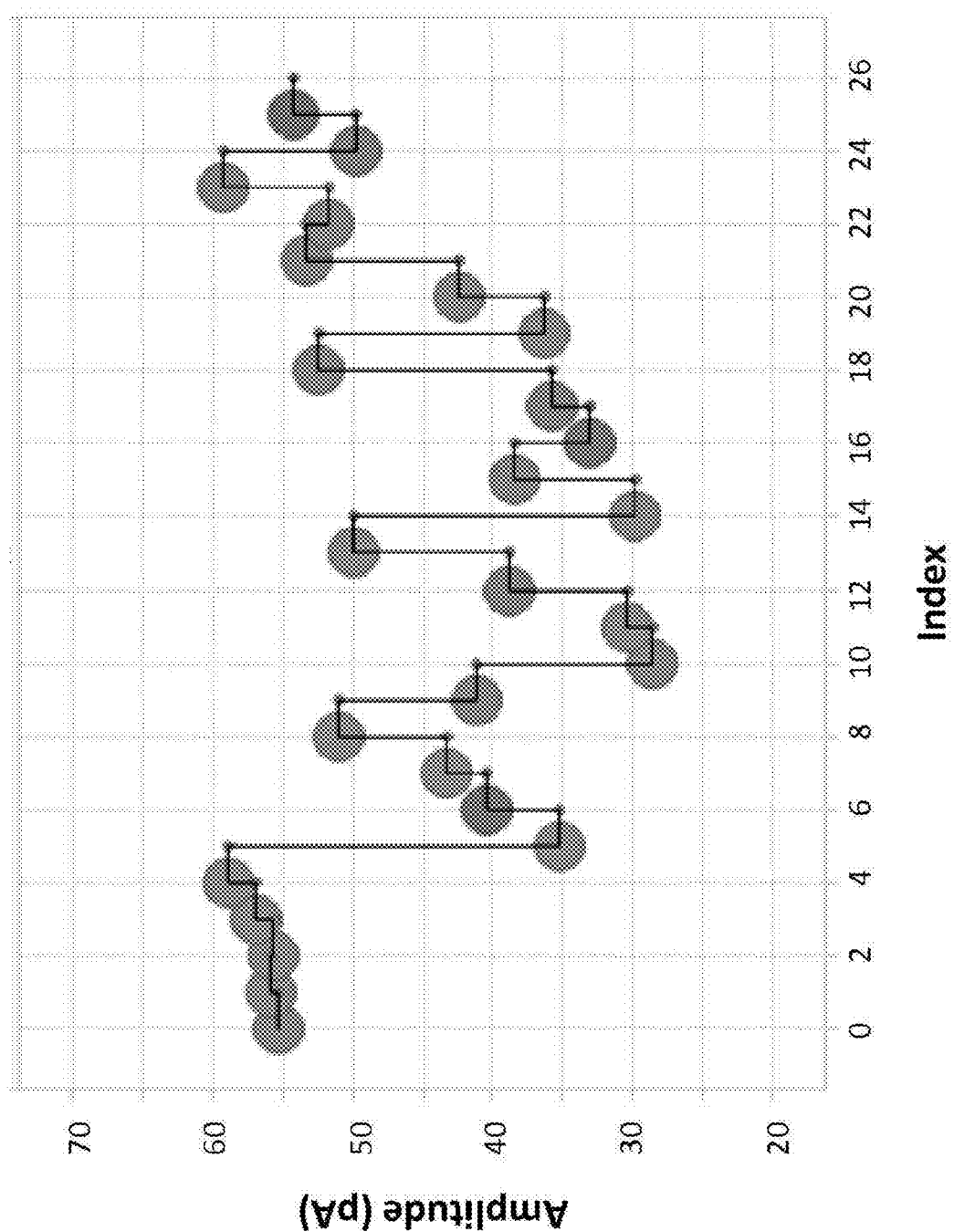
FIG. 9 shows the current levels produced when DNA is unzipped through the baseline MS-(B1)$_8$ pore. Current range for these events is ~30 pA.
Figure 10:
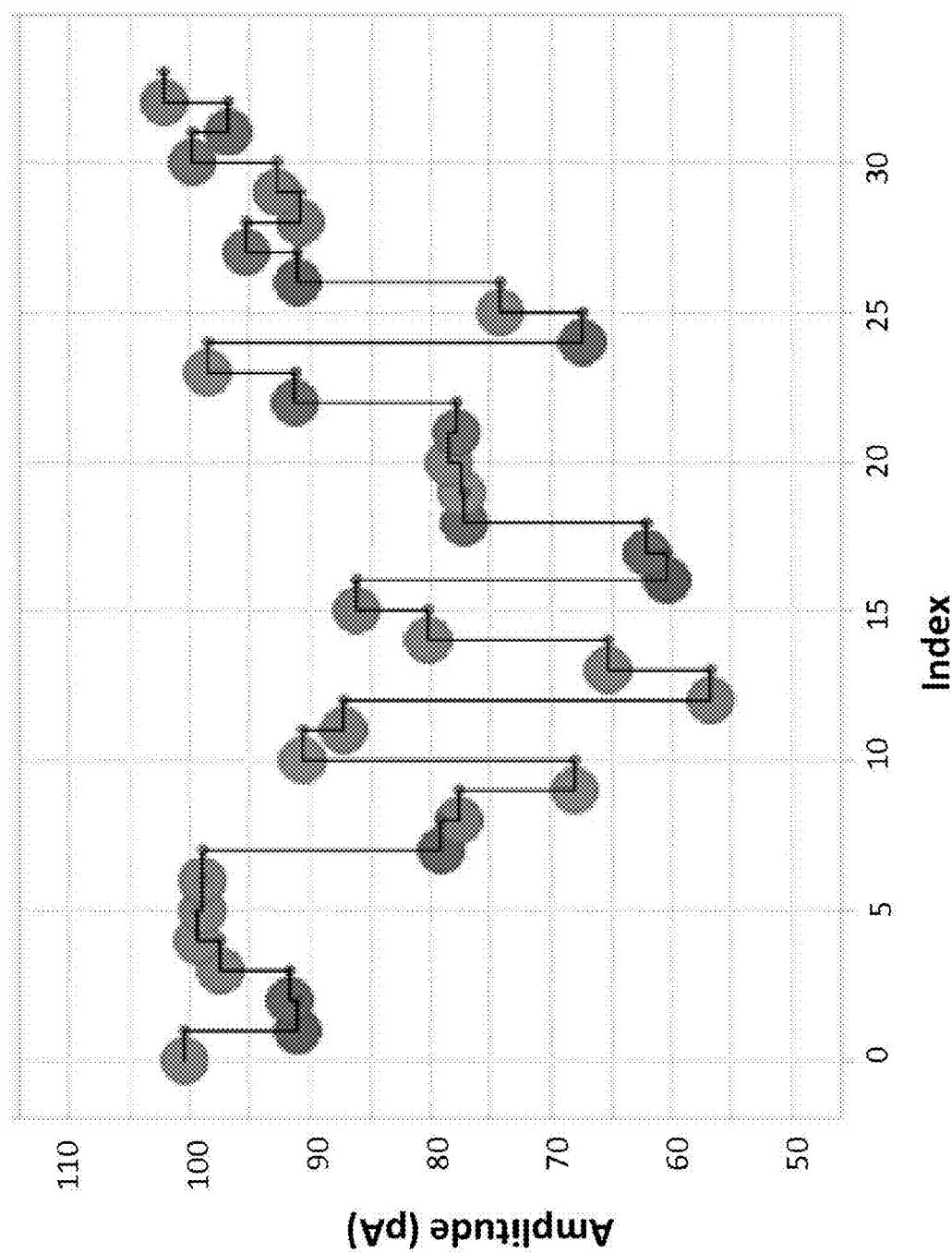
FIG. 10 shows the current levels produced when DNA is unzipped through the baseline MS-(B1-I105A)$_8$ pore. Current range for these events is ~40 pA.

The spread of current levels from the DNA strand moving through the MS-(B1)$_8$ mutant was ~30 pA under these conditions (FIG. 9). The same experiment was repeated using the MS-(B1-I105A)$_8$ mutant, the current levels exhibited a range of ~40 pA for the same DNA strand (FIG. 10). The larger current range of the MS-(I105A)$_8$ mutant is desirable to discriminate combinations of nucleotides within the nanopore.

Example 9—Signal Noise Comparison of the MS-(B1)8 Baseline to the MS-(B1-L88N)8 Mutants The noise levels of MspA pores can be controlled by mutating the L88 position in the MspA monomer sequence. It was demonstrated that the noise level can be reduced by 19% as a result of making a single mutation to the MspA monomer.

This example compares the MS-(B1)8 pore and the MS-(B1-L88N)8 pores in translocating mode, by using a helicase to control the movement of intact DNA strands through a nanopore.

Materials

Primers were designed to amplify a ~400 bp fragment of PhiX174. Each of the 5'-ends of these primers included a 50 nucleotide non-complimentary region, either a homopolymeric stretch or repeating units of 10 nucleotide homopolymeric sections. These serve as identifiers for controlled translocation of the strand through a nanopore, as well as determining the directionality of translocation. In addition, the 5'-end of the forward primer was "capped" to include four 2'-O-Methyl-Uracil (mU) nucleotides and the 5'-end of the reverse primer was chemically phosphorylated. These primer modifications then allow for the controlled digestion of predominantly only the antisense strand, using lambda exonuclease. The mU capping protects the sense strand from nuclease digestion whilst the PO4 at the 5' of the antisense strand promotes it. Therefore after incubation with lambda exonuclease only the sense strand of the duplex remains intact, now as single stranded DNA (ssDNA). The generated ssDNA was then PAGE purified as previously described.

Figure 11:
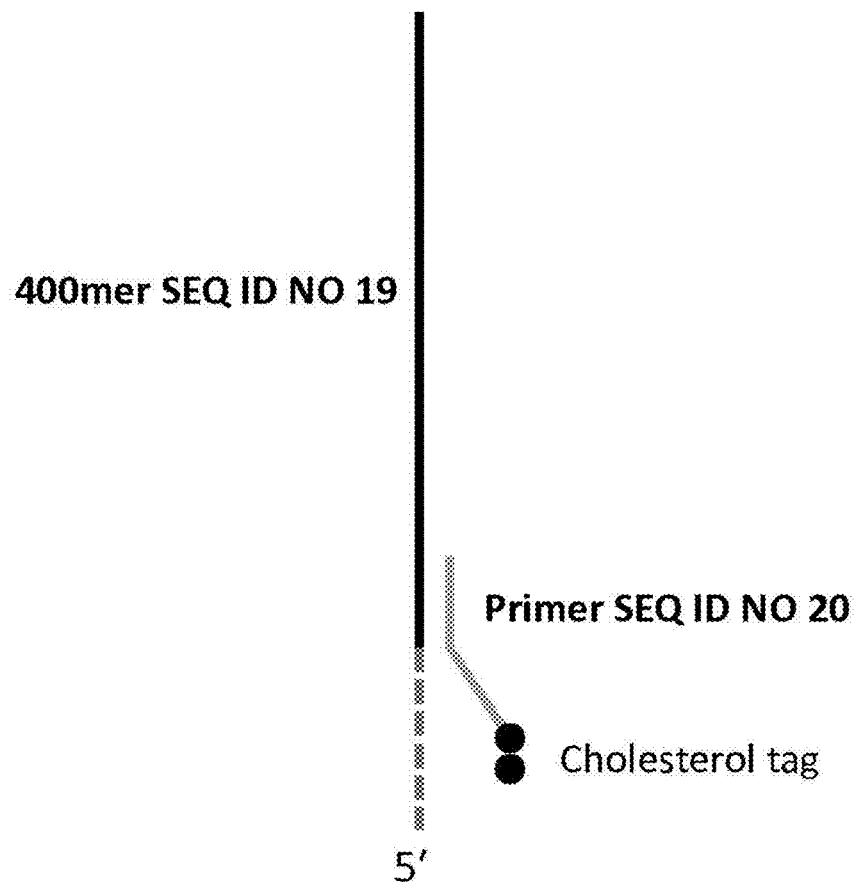
FIG. 11 shows the DNA substrate design used in Examples 9 and 12 and 15.

The DNA substrate design used in this experiment is shown in FIG. 11 (SEQ ID NOs: 19 and 20 (sequences and tags presented below)). The DNA substrate consists of a 400base section of ssDNA from PhiX, with a 50T 5'-leader to aid capture by the nanopore. Annealed to this strand just after the 50T leader is a primer containing a 3' cholesterol tag β' Cholesteryl-TEG) to enrich the DNA on the surface of the bilayer, and thus improve capture efficiency.

```
                                    SEQ ID NO: 19
mUmUmUmUTTTTTTTTTTTTTTTTTTTTTTTTTTTTTTTTTTTT

TTTTTTTTTTTTGGTTGTTTCTGTTGGTGCTGATATTGCTTTTGATGCC

GACCCTAAATTTTTTGCCTGTTTGGTTCGCTTTGAGTCTTCTTCGGTTCC

GACTACCCTCCCGACTGCCTATGATGTTTATCCTTTGAATGGTCGCCATG

ATGGTGGTTATTATACCGTCAAGGACTGTGTGACTATTGACGTCCTTCCC

CGTACGCCGGGCAATAACGTTTATGTTGGTTTCATGGTTTGGTCTAACTT
```

```
                                    -continued
TACCGCTACTAAATGCCGCGGATTGGTTTCGCTGAATCAGGTTATTAAAG

AGATTATTTGTCTCCAGCCACTTAAGTGAGGTGATTTATGTTTGGTGCTA

TTGCTGGCGGTATTGCTTCTGCTCTTGCTGGTGGCGCCATGTCTAAATTG

TTTGGAGGCGGTC
```

```
                                    SEQ ID NO: 20
(plus 3' Cholesteryl-TEG tag)
    GCAATATCAGCACCAACAGAAACAACCTTTTTTTTTTTTTTTT TTTTTTTTTTT/3CholTEG/
```

Experimental Method

Buffered solution: 400 mM NaCl, 10 mM Hepes pH 8.0, 1 mM ATP, 1 mM MgCl$_2$, 1 mM DTT Nanopores: MS(B1)8 MspA; MS(B1-L88N)8 MspA Enzyme: Helicase Electrical measurements were acquired from single MspA nanopores inserted in 1,2-diphytanoyl-glycero-3-phosphocholine lipid (Avanti Polar Lipids) bilayers. Bilayers were formed across ~100 μm diameter apertures in 20 μm thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Ag/AgCl electrodes were connected to the buffered solutions so that the cis compartment (to which both nanopore and enzyme/DNA are added) is connected to the ground of the Axopatch headstage, and the trans compartment is connected to the active electrode of the headstage.

After achieving a single pore of either MS(B1)8 or MS(B1-L88N)8 in the bilayer, DNA polynucleotide (SEQ ID NOs: 19 and 20) and helicase were added to 100 μL of buffer and pre-incubated for 5 mins (DNA=1.5 nM, Enzyme=1 μM). This pre-incubation mix was added to 900 μL of buffer in the cis compartment of the electrophysiology chamber to initiate capture of the helicase-DNA complexes in the MspA nanopore (to give final concentrations of DNA=0.15 nM, Enzyme=0.1 μM). Helicase ATPase activity was initiated as required by the addition of divalent metal (1 mM MgCl$_2$) and NTP (1 mM ATP) to the cis compartment. Experiments were carried out at a constant potential of +140 mV. Current levels were extracted as events from the DNA in the enzyme bound state these events were indexed and the current level, duration and variance of the event recorded.

Using the MspA pore MS-(B1)8, 31.08% of the detected events had a standard deviation >2.0 at an applied potential of +140 mV (additional data summarized in Table 18). The experiment was repeated with the MS-(B1-L88N)8 mutant where only 12.38% of the detected events exhibited a standard deviation of >2.0 at an applied potential of +140 mV (additional data summarized in Table 18). Therefore, the point mutation at L88 in the MspA monomer sequence has reduced the observed noise range by 19%

TABLE 18

| | Pore | |
|---|---|---|
| Property | MS-(B1)8 | MS-(B1-L88N)8 |
| Mean S.D. | 2.30 | 1.79 |
| Median S.D. | 1.57 | 1.48 |
| % of S.D. > 2 | 31.08 | 12.38 |

Example 10—Signal Noise Comparison of the MS-(B1)8 Baseline to the MS-(B1-L88N)8, MS-(B1-L88S)8 and MS-(B1-L88O)8 Mutants The noise levels of MspA pores can be altered by mutating the L88 position in the protein. It was demonstrated that the noise level can be reduced as a result of making a single mutation to the MspA monomer.

Figure 12:
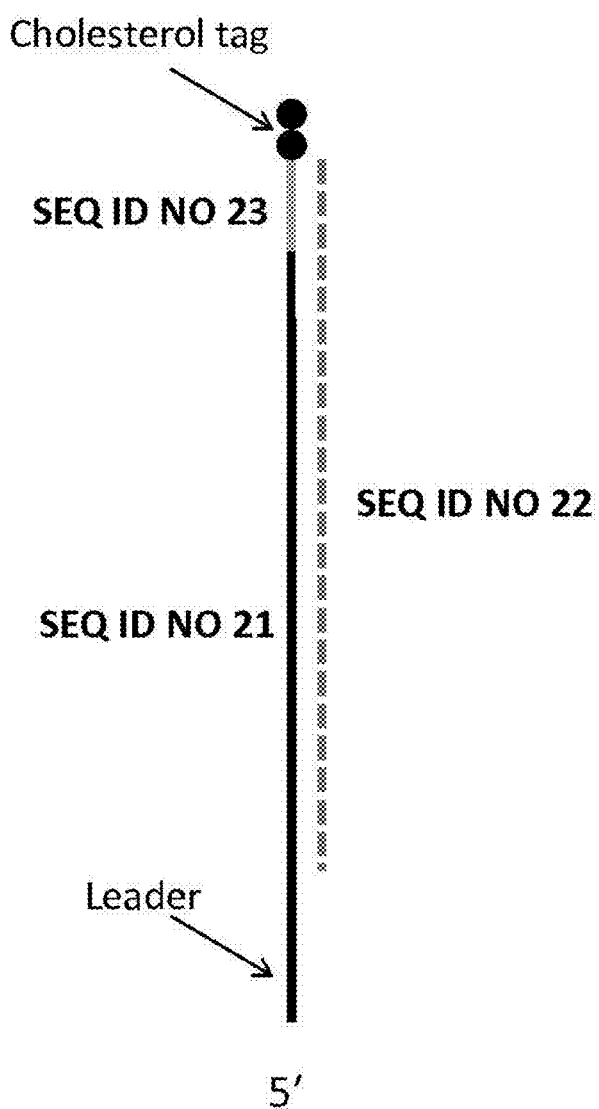
FIG. 12 shows the DNA substrate design used in Examples 10 and 11.

This example compares the MS-(B1)8 pore to the MS-(B1-L88N)8, MS-(B1-L88S)8 and MS-(B1-L88Q)8 pores in unzipping mode, by using Phi29 DNA polymerase to control the movement of DNA strands through a nanopore. The DNA substrate design used in all the experiments described in this example is shown in FIG. 12 (SEQ ID NOs: 21, 22 and 23). SEQ ID NO: 23 was tagged with an IDT Int Spacer 9 (iSp9) and 3' Cholesteryl-TEG (3CholTEG) as shown below. The runs were conducted at room temperature at an applied potential of +180 mV.

```
SEQ ID NO: 23:
CAGCGATGGAGATAC/iSp9//3CholTEG/
```

Experimental Method
Buffered solution: 400 mM KCl, 10 mM Hepes pH 8.0, 1 mM EDTA, 1 mM DTT
Nanopores: MS(B1)8 MspA;
MS(B1-L88N)8 MspA;
MS(B1-L88S)8 MspA;
MS(B1-L88Q)8 MspA;
Enzyme: Phi29 DNA polymerase SEQ ID NO: 4

Electrical measurements were acquired as described in example 9. After achieving a single pore of either MS(B1)8, MS(B1-L88N)8, MS(B1-L88S)8 or MS(B1-L88Q)8 in the bilayer, DNA polynucleotide (SEQ ID NOs: 21, 22 and 23) and Phi29 DNA polymerase were added to 100 μL of buffer and pre-incubated for 5 mins. This pre-incubation mix was added to 900 μL of buffer in the cis compartment of the electrophysiology chamber to initiate capture of the polymerase-DNA complexes in the MspA nanopore (to give final concentrations of DNA=0.5 nM, Enzyme=0.1 μM). Experiments were carried out at a constant potential of +180 mV. Current levels observed when the DNA is in the enzyme bound state were indexed and the current level, its duration and variance were recorded.

In the experiments, the baseline MS-(B1)8 mutant exhibited high levels of noise (76.15% of standard deviations >2.0, see Table 19) at +180 mV. The other three mutants tested, (MS-(B1-L88N)8, MS-(B1-L88S)8 and MS-(B1-L88Q)8) which had a single point mutation at position L88, all observed lower levels of noise (see Table 19) than the baseline pore over the same DNA strand sequence. Therefore, it was possible to reduce signal noise by applying point mutations at position L88 in MspA monomer sequence.

TABLE 19

| Pore | Mean S.D | Median S.D | % of S.D. > 2 |
|---|---|---|---|
| MS-(B1)8 | 3.26 | 2.89 | 76.15 |
| MS-(B1-L88N)8 | 3.22 | 2.60 | 74.18 |
| MS-(B1-L88S)8 | 3.12 | 2.33 | 71.71 |
| MS-(B1-L88Q)8 | 3.30 | 2.46 | 74.19 |

Example 11—Overall Signal Range Comparison of the MS-(B1)8 Baseline to Other MspA Mutants The signal range of MspA pores can be increased by mutating various positions within the MspA protein monomer sequence.

This example compares the MS-(B1)8 pore to the following pores—MS-(B1-D90Q)8, MS-(B1-I105L)8, MS-(B1-I105Y)8, MS-(B1-I89Y-D90S)8, MS-(B1-N86T)8 and MS-(B1-S103G)8—pores in unzipping mode, by using a Phi29 DNA polymerase to control the movement of intact DNA strands through a nanopore. The DNA substrate design, used in all the experiments described in this example, is shown in FIG. 12 (SEQ ID NOs: 21, 22 and 23). SEQ ID NO: 23, tagged with iSp9 and 3CholTEG is shown above. The runs were conducted at room temperature at an applied potential of +180 mV. Current levels observed when the DNA is in the enzyme bound state were indexed and the current level, its duration and variance were recorded.

Experimental Method
Buffered solution: 400 mM KCl, 10 mM Hepes pH 8.0, 1 mM EDTA, 1 mM DTT
Nanopores: MS(B1)8 MspA;
MS(B1-D90Q)8 MspA;
MS-(B1-I105L)8 MspA;
MS-(B1-I105Y)8 MspA;
MS-(B1-I89Y-D90S)8 MspA;
MS-(B1-N86T)8 MspA;
MS-(B1-S103G)8 MspA;
Enzyme: Phi29 DNA polymerase SEQ ID NO: 4

Electrical measurements were acquired as described in example 10. After achieving a single pore of either MS(B1)8, MS(B1-D90Q)8, MS(B1-I105L)8, MS(B1-I105Y)8, MS-(B1-I89Y-D90S)8, MS-(B1-N86T)8 or MS-(B1-S103G)8 in the bilayer, DNA polynucleotide (SEQ ID NOs: 21, 22 and 23) and Phi29 DNA polymerase were added to 100 μL of buffer and pre-incubated for 5 mins. This pre-incubation mix was added to 900 μL of buffer in the cis compartment of the electrophysiology chamber to initiate capture of the polymerase-DNA complexes in the MspA nanopore (to give final concentrations of DNA=0.5 nM, Enzyme=0.1 μM). Experiments were carried out at a constant potential of +180 mV. Current levels observed when the DNA is in the enzyme bound state were indexed and the current level, its duration and variance were recorded.

In the experiments, the baseline MS-(B1)8 mutant exhibited a maximum range of 35 pA at +180 mV (Table 20). The other 6 mutants tested (MS-(B1-D90Q)8, MS-(B1-I105L)8, MS-(B1-I105Y)8, MS-(B1-I89Y-D90S)8, MS-(B1-N86T)8 and MS-(B1-S103G)8) all observed a greater maximum range than the baseline pore (See Table 20) over the same DNA strand sequence. Therefore, it was possible to increase signal range by applying point mutations at various locations in the MspA monomer sequence.

TABLE 20

| Entry No. | Mutant Pore | Range (pA) |
|---|---|---|
| 1 | MS(B1)8 | 34 |
| 2 | MS-(B1-D90Q)8 | 70 |
| 3 | MS-(B1-I105L)8 | 42 |
| 4 | MS-(B1-I105Y)8 | 45 |
| 5 | MS-(B1-I89Y-D90S)8 | 67 |
| 6 | MS-(B1-N86T)8 | 58 |
| 7 | MS-(B1-S103G)8 | 54 |

Example 12—Overall Sequencing Profile Comparison of the MS-(B1)8 Baseline to Other MspA Mutants The sequencing profile of MspA pores can be controlled by mutating a variety of positions in the MspA protein monomer sequence.

This example compares the MS-(B1)8 pore to MS-(B1-D90Q-D93S-I105A)8, MS-(B1-D90Q-Q126R)8, MS-(B1-L88N-D90Q-D91M)8, MS-(B1-L88N-D90Q-D91S)8 and MS-(B1-G75S-G77S-L88N-Q126R)8 pores in translocating mode, by using a helicase to control the movement of intact DNA strands through a nanopore.
Experimental Method
Buffered solution: 400 mM NaCl, 10 mM Hepes pH 8.0, 1 mM ATP, 1 mM MgCl$_2$, 1 mM DTT
Nanopores: MS(B1)8 MspA;
MS(B1-D90Q-D93S-I105A)8 MspA;
MS(B1-D90Q-Q126R)8 MspA;
MS(B1-L88N-D90Q-D91M)8 MspA;
MS(B1-L88N-D90Q-D91S)8 MspA;
MS(B1-G75S-G77S-L88N-Q126R)8 MspA;
Enzyme: Helicase The experimental set-up was carried out as described in Example 9. After achieving a single pore of either MS-(B1)8, MS-(B1-D90Q-D93S105A)8, MS-(B1-D90Q-Q126R), MS-(B1-L88N-D90Q-D91M)8, MS-(B1-L88N-D90Q-D91S)8 or MS-(B1-G75S-G77S-L88N-Q126R)8 in the bilayer, DNA polynucleotide (SEQ ID NOs: 19 and 20 (sequence and tags shown above)) and helicase were added to 100 L of buffer and pre-incubated for 5 mins (DNA=1.5 nM, Enzyme=1 µM). This pre-incubation mix was added to 900 µL of buffer in the cis compartment of the electrophysiology chamber to initiate capture of the helicase-DNA complexes in the MspA nanopore (to give final concentrations of DNA=0.15 nM, Enzyme=0.1 µM). Helicase ATPase activity was initiated as required by the addition of divalent metal (1 mM MgCl$_2$) and NTP (1 mM ATP) to the cis compartment. Experiments were carried out at a constant potential of +140 mV. Current levels observed when the DNA is in the enzyme bound state were indexed and the current level, its duration and variance were recorded.

Figure 13:
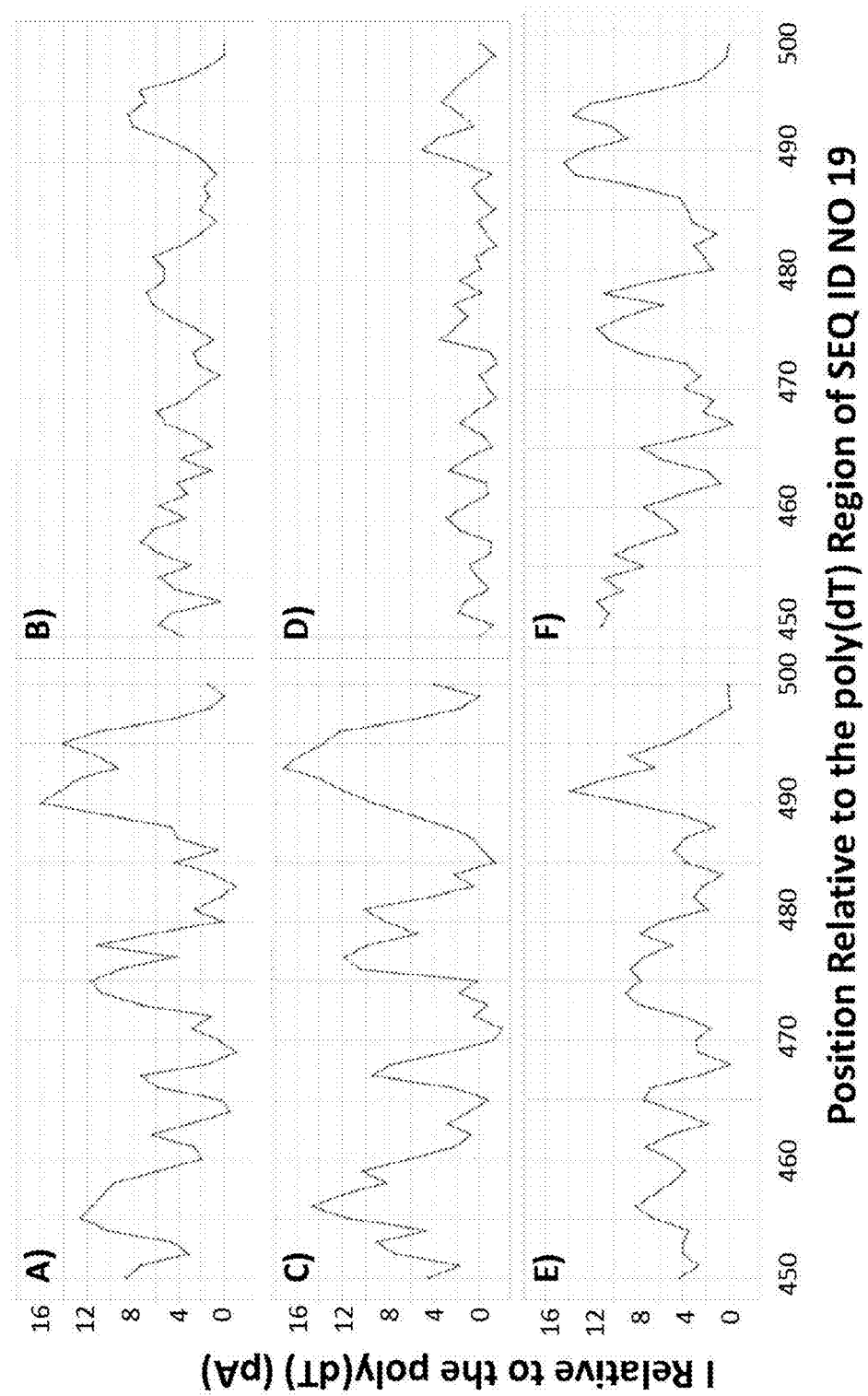
FIG. 13 shows how the sequencing profile changes, for the same DNA sequence, when point mutations are made in the MspA monomer sequence. These plots show the average of the profile of the levels obtained from multiple polynucleotides. A) This graph shows the sequencing profile for the MS-(B1)8 pore. B) This graph shows the sequencing profile for the MS-(B1-D90Q-D93S-I105A)8 pore. C) This graph shows the sequencing profile for the MS-(B1-D90Q-Q126R)8 pore. D) This graph shows the sequencing profile for the MS-(B1-L88N-D90Q-D91M)8 pore. E) This graph shows the sequencing profile for the MS-(B1-L88N-D90Q-D91S)8 pore. F) This graph shows the sequencing profile for the MS-(B1-G75S-G77S-L88N-Q126R)8 pore.

In the experiments, the baseline MS-(B1)8 mutant produced the sequencing profile shown in FIG. 13a. The experiment was repeated with the following mutants MS-(B1-D90Q-D93S-I105A)8, MS-(B1-D90Q-Q126R), MS-(B1-L88N-D90Q-D91M)8, MS-(B1-L88N-D90Q-D91S)8 and MS-(B1-G75S-G77S-L88N-Q126R)8, which exhibited a variety of different sequencing profiles (see FIG. 13 b-f). Therefore, by making point mutations at a variety of positions within MspA monomer sequence it is possible to alter the sequencing profile that is detected.

Example 13—Analysis of an RNA Strand Sequence Using the MS-(B1)8 Baseline Pore

This example describes how the MspA baseline pore MS-(B1)8 combined with the Phi29 DNA polymerase can be used to sequence a strand of RNA.

Figure 14:
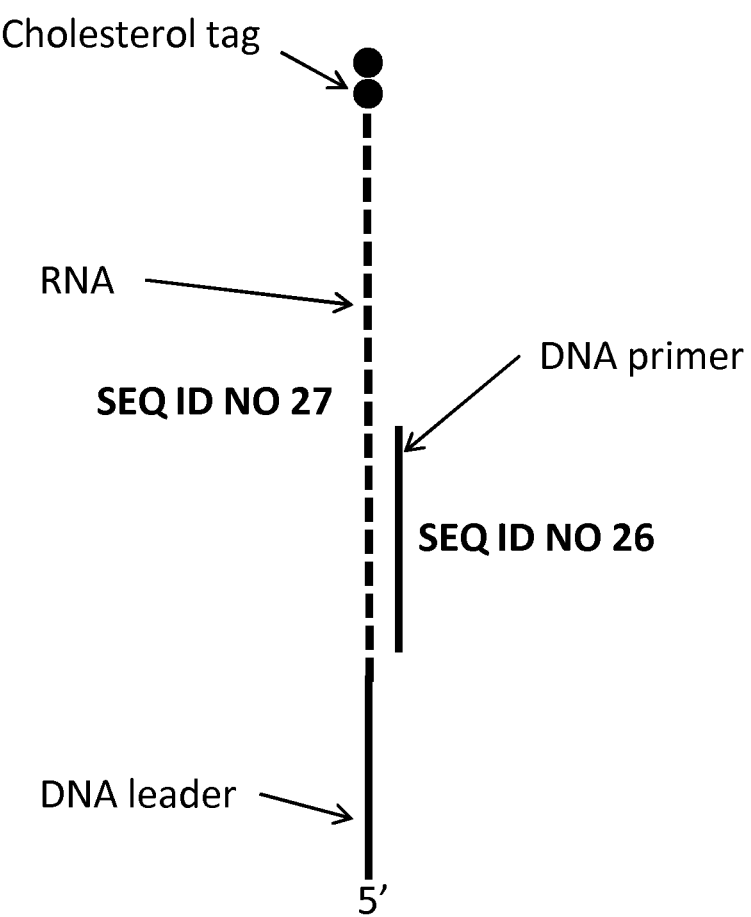
FIG. 14 shows the DNA substrate design used in Example 13.

This example uses the MS-(B1)8 pore in unzipping mode, by using a Phi29 DNA polymerase to control the movement of intact RNA strands through a nanopore. The RNA/DNA hybrid substrate design used in this experiment is shown in FIG. 14 (SEQ ID NOs: 24 and 25). SEQ ID NOs: 24 and 25 are presented below (RNA in bold). The runs were conducted at room temperature at an applied potential of +180 mV.

SEQ ID NO: 24:
5'OH-
CCCCCCCCCCCCCCACCCCCCCCCCCCCCCCCCCUAUUCUGUUUAUGUU

UCUUGUUUGU- 3'OH

SEQ ID NO: 25 (plus cholesterol tag):
5'Phos-

UAUUCUGUUUAUGUUUCUUGUUUGUUAGCCCCCUUUGAUAAGACAAAUA

CAAAGAACAAA-3'Chol

Materials
In order to synthesize the RNA/DNA hybrid strand (120 mer in length), it was necessary to ligate SEQ ID NOs: 24 and 25 together. This was achieved by using the complementary DNA adapter strand SEQ ID NO: 26 to bring the two strands into close proximity, where they were subsequently ligated together forming the 120mer DNA/RNA hybrid SEQ ID NO: 27.

SEQ NO: 27 (plus cholesterol tag; RNA in bold):
5'OH-

CCCCCCCCCCCCCCACCCCCCCCCCCCCCCCCCUAUUCUGUUUAUGUU

UCUUGUUUGUUAUUCUGUUUAUGUUUCUUGUUUGUUAGCCCCCUUUGAUA

AGACAAAUACAAAGAACAAA-3'Chol

Experimental Method
Buffered solution: 400 mM KCl, 10 mM Hepes pH 8.0, 1 mM EDTA, 1 mM DTT
Nanopore: MS(B1)8 MspA;
Enzyme: Phi29 DNA polymerase SEQ ID NO: 4

Electrical measurements were acquired as described in example 10. After achieving a single pore of MS(B1)8 in the bilayer, DNA polynucleotide (SEQ ID NOs: 24 and 25) and Phi29 DNA polymerase were added to 100 µL of buffer and pre-incubated for 5 mins. This pre-incubation mix was added to 900 µL of buffer in the cis compartment of the electrophysiology chamber to initiate capture of the polymerase-DNA complexes in the MspA nanopore (to give final concentrations of DNA=0.2 nM, Enzyme=0.2 µM). Experiments were carried out at a constant potential of +180 mV. Current levels were extracted as events from the DNA in the enzyme bound state these events were indexed and the current level, duration and variance of the event recorded.

Figure 15:
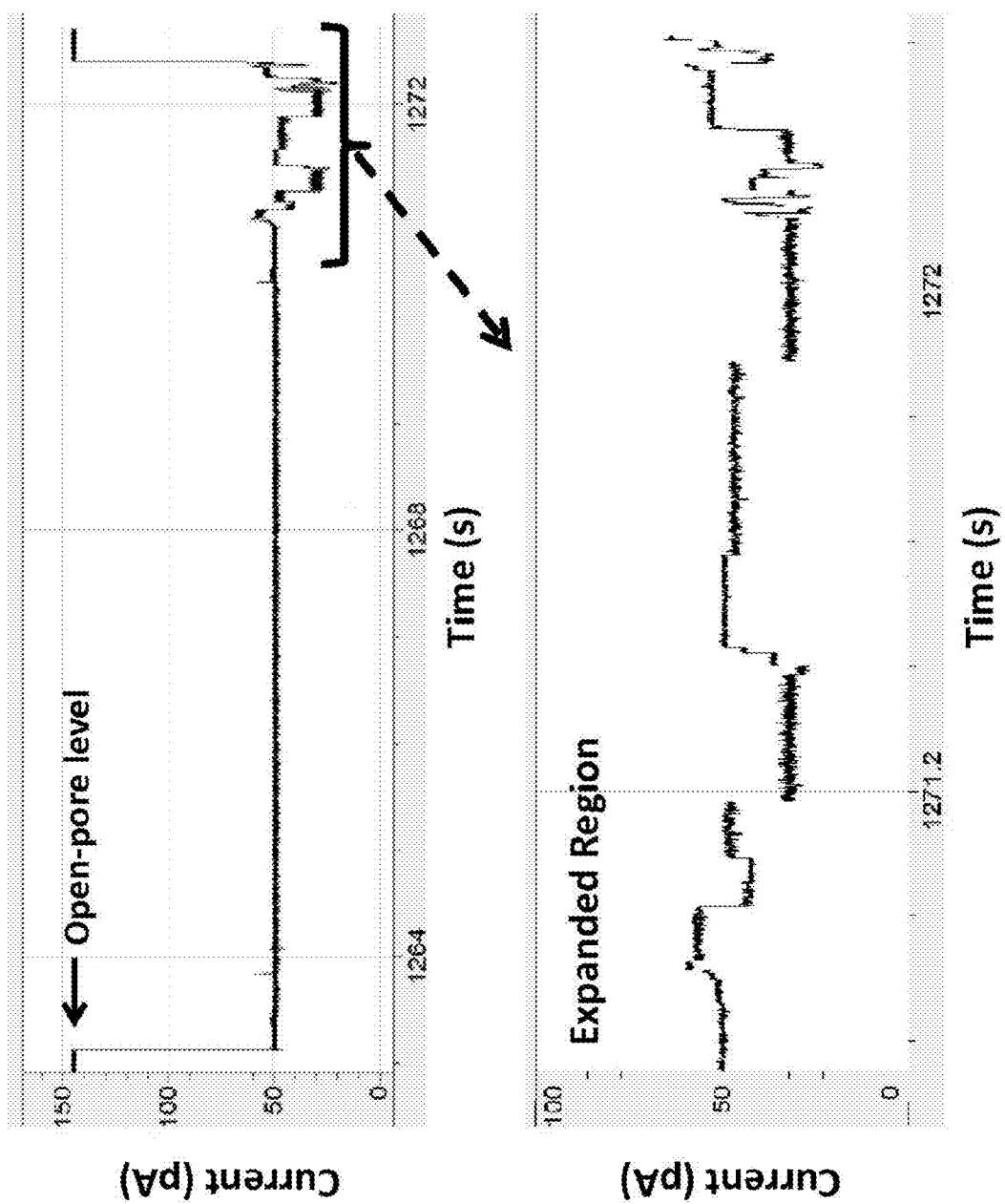
FIG. 15 shows an example event trace for the controlled translocation of RNA, mediated by Phi29 DNA polymerase, through the MspA mutant pore MS-(B1)8. An expanded view, of the region highlighted in the upper trace, is shown below.

In the experiments, the baseline MS-(B1)8 mutant, combined with Phi29 DNA polymerase as a molecular motor, was observed to detect distinct current levels as the RNA strand was threaded through the pore. These current signals were then used to determine the sequence of the target. Typical RNA translocation events, in Phi29 DNA polymerase unzipping mode, are shown in FIG. 15.

Example 14—MspA Dimer and Oligomerisation to Form Pores

This example describes the preparation and oligomerisation of the MspA dimer.
Preparation of Dimer
MspA NNNRRK monomeric protein consists of 184 amino acid residues. A single polypeptide was designed to make a dimeric version of MspA-NNNRRK protein.

DNA sequence encoding the 184 residue MspA-NNNRRK polypeptide was linked to a second DNA sequence encoding the identical polypeptide chain via a short DNA linker sequence. The linker DNA sequence encodes SGSGSGDDDDDDDDSGSGSS (SEQ ID NO: 33; shown as -(SG)$_3$-D$_8$-(SG)$_2$(SS)-). An initiator codon (ATG) was added just before the first base and a DNA encoding two stop codons (TAATAG) was added after the last base. Therefore, the entire DNA sequence encoding MspA-NNNRRK-(SG)$_3$-D$_8$-(SG)$_2$(SS)-MspA-NNNRRK is shown in SEQ ID NO: 28.

The DNA was synthesised at GenScript USA Inc and cloned into a pT7 vector for expression purposes.

Protein was generated by coupled in vitro transcription and translation (IVTT) by using an *E. coli* T7-S30 extract system for circular DNA (Promega).

The complete 1 mM amino acid mixture minus cysteine and the complete 1 mM amino acid mixture minus methionine were mixed in equal volumes to obtain the working amino acid solution required to generate high concentrations of the proteins. The amino acid mix (2.5.0 µL), premix solution (10 µL), [35S]L-methionine (0.5 µL) and rifampicin (2 µL, 50 mg/mL) were mixed with plasmid DNA (4 µL, 400 ng/mL) and T7 S30 extract (7.5 µL). Synthesis was carried out for 90 min at 37° C. to generate 25 µL of IVTT proteins for MspA-NNNRRK monomer and dimer. After the reaction, samples were centrifuged at 25,000 g for 10 mins and the supernatant was discarded. The pellet was washed with 100 µL MBSA (10 mM MOPS, 150 mM NaCl, pH 7.4 containing 1 mg/mL BSA) and resuspended in 25 µL Lamellae sample buffer. Samples were subjected to SDS-PAGE on a 10% gel. The gel was dried at 80° C. for 45 mins and exposed to X-ray film for 2 hours. The gel showed 2 distinct bands, one corresponding to the MspA dimer and one to the MspA monomer.

Oligomerisation of Monomer and Dimer

Expression of the dimer and, separately, the monomer was carried out in the presence of synthetic lipid vesicles to facilitate oligomerisation. A five component lipid mixture was used (PS:SM:PE:PC:Cholesterol in 10:10:20:30:30 ratio, 25 mg/mL). 50 µL of lipid mixture was centrifuged at 25,000 g for 10 mins in a 1.5 mL eppendorf tube and the supernatant was discarded. The complete 1 mM amino acid mixture minus cysteine and the complete 1 mM amino acid mixture minus methionine were mixed in equal volumes to obtain the working amino acid solution required to generate high concentrations of the proteins. The membrane pellet was resuspended with amino acid mix (10.0 µL), premix solution (40 µL), [35S]L-methionine and rifampicin (2 µL, 50 mg/mL). Plasmid DNA (16 µL, 400 ng/mL) and T7 S30 extract (30.0 µL) were added to initiate synthesis. Synthesis was carried out for 90 min at 37° C. to generate 100 µL of IVTT protein. IVTT reaction sample was centrifuged (25,000 g, 10 mins) and the resulting membrane pellet was washed with MBSA and subjected to SDS—polyacrylamide gel electrophoresis in a 7.5% gel. The gel was dried on a watman 3M paper at 50° C. for 3 hours and exposed to X-ray film for 2 hours. The gel showed 8 distinct bands for the oligomerised MspA dimer, all of which migrated more slowly in SDS PAGE than the oligomerised monomer.

Protein Purification for Bilayer Experiments

Three protein bands from the dimer oligomerisation experiment were excised from the gel and purified. Using the autoradiogram as the template, bands were cut and rehydrated in buffer (150 to 200 µL of 25 mM Tris.HCl, pH 8.0). The paper was removed and the gel piece was crushed using a pestle. The slurry was filtered through a QIAshredder column (Qiagen) by centrifugation at 25,000× g for 10 min. The resulting protein from the third band from the monomer level was then used in the electrophysiology experiments described in Example 15.

Example 15—Comparison of the MS-(B1)8 Oligomerised from the Monomer with the MS-(B1-B1)4 Oligomerised from the Dimer This example compares the MS-(B1)8 pore oligomerised from the monomer (SEQ ID NO: 2) with the MS-(B1-B1)4 pore oligomerised from the dimer (SEQ ID NO: 29) in translocating mode, by using a helicase to control the movement of intact DNA strands (SEQ ID NOs: 19 and 20 (sequence and tags shown above)) through a nanopore.

Experimental Method

Buffered solution: 400 mM NaCl, 10 mM Hepes pH 8.0, 1 mM ATP, 1 mM MgCl$_2$, 1 mM DTT Nanopores: MS-(B1)8;
MS-(B1-B1)4

Enzyme: Helicase

Electrical measurements were acquired using 128 well silicon chips (format 75 µm diameter, 20 µm depth and 250 µm pitch) which were silver plated (WO 2009/077734). Chips were initially washed with 20 mL ethanol, then 20 mL dH$_2$O, then 20 mL ethanol prior to CF4 plasma treatment. The chips used were then pre-treated by dip-coating, vacuum-sealed and stored at 4° C. Prior to use the chips were allowed to warm to room temperature for at least 20 minutes.

Bilayers were formed by passing a series of slugs of 3.6 mg/mL 1,2-diphytanoyl-glycero-3-phosphocholine lipid (DPhPC, Avanti Polar Lipids, AL, USA) dissolved in 1 M KCl, 10 mM Tris, pH 7.5, at 0.45 µL/s across the chip. Initially a lipid slug (250 µL) was flowed across the chip, followed by a 100 µL slug of air. Two further slugs of 155 µL and 150 µL of lipid solution, each separated by a 100 µL slug of air were then passed over the chip. After bilayer formation the chamber was flushed with 3 mL of buffer at a flow rate of 3 µl/s. Electrical recording of the bilayer formation was carried out at 10 kHz with an integration capacitance of 1.0 pF.

A solution of the biological nanopore was prepared using either the MS-(B1)8 pore oligomerised from the monomer or the MS-(B1-B1)4 pore oligomerised from the dimer in 10 mM Tris, 1 mM EDTA, pH 8.0. A holding potential of +180 mV was applied and the solution flowed over the chip and pores were allowed to enter bilayers. The sampling rate and the integration capacitance were then maintained at 10 kHz and 1.0 pF respectively and the applied potential reduced to zero.

A control program, which applied a holding potential of +180 mV, was run. DNA polynucleotide (SEQ ID NOs: 19 and 20) and helicase were pre-incubated for 5 mins. This pre-incubation mix (which included MgCl$_2$ and ATP) was then flowed over the chip to initiate capture of the helicase-DNA complexes in the MspA nanopore (to give final concentrations of DNA=1.5 nM, Enzyme=10 nM). Experiments were carried out at a constant potential of +180 mV. Current levels were extracted as events from the DNA in the enzyme bound state. These events were indexed and the current level, duration and variance of the event recorded.

Figure 16:
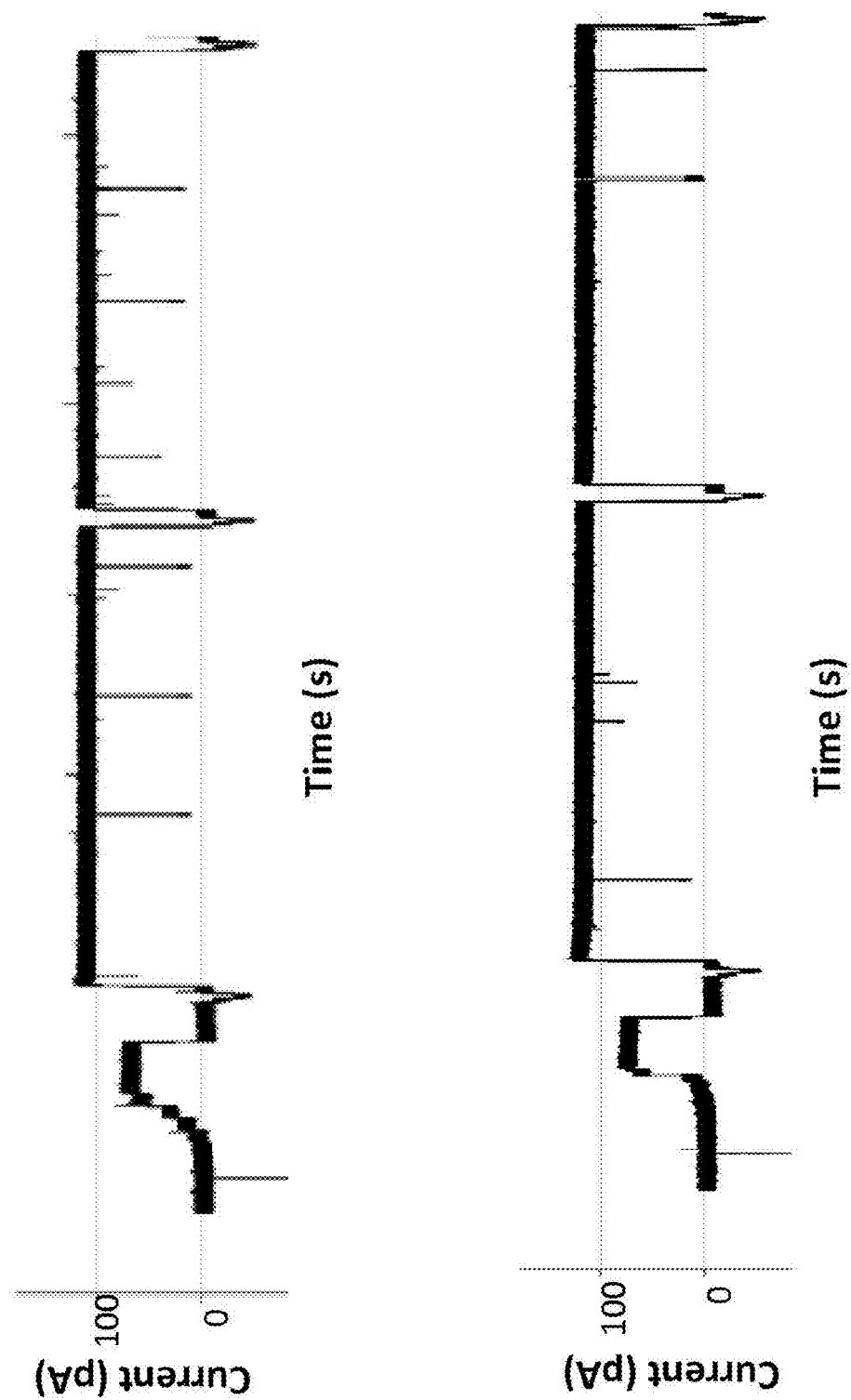
FIG. 16 shows pore insertion into the lipid bilayer. A) Shows pore insertion of the MS-(B1)8 oligomerised from the monomer. B) Shows pore insertion of the MS-(B1-B1)4 oligomerised from the dimer.
Figure 17:
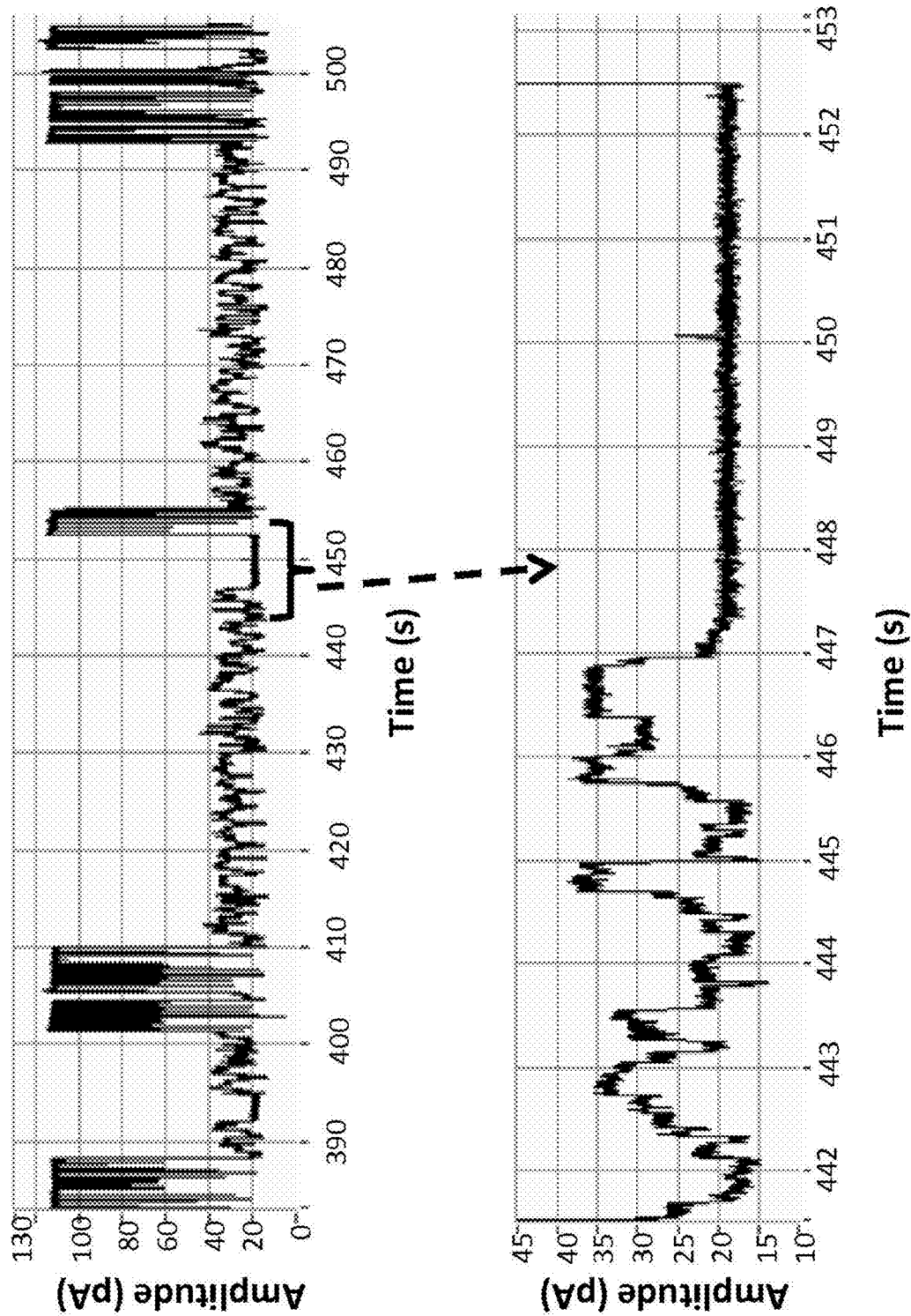
FIG. 17 shows an example event trace for the controlled translocation of DNA, mediated by a helicase, through the MS-(B1)8 mutant pore which was produced by oligomerisation of the monomer. An expanded view, of the region highlighted in the upper trace, is shown below.
Figure 18:
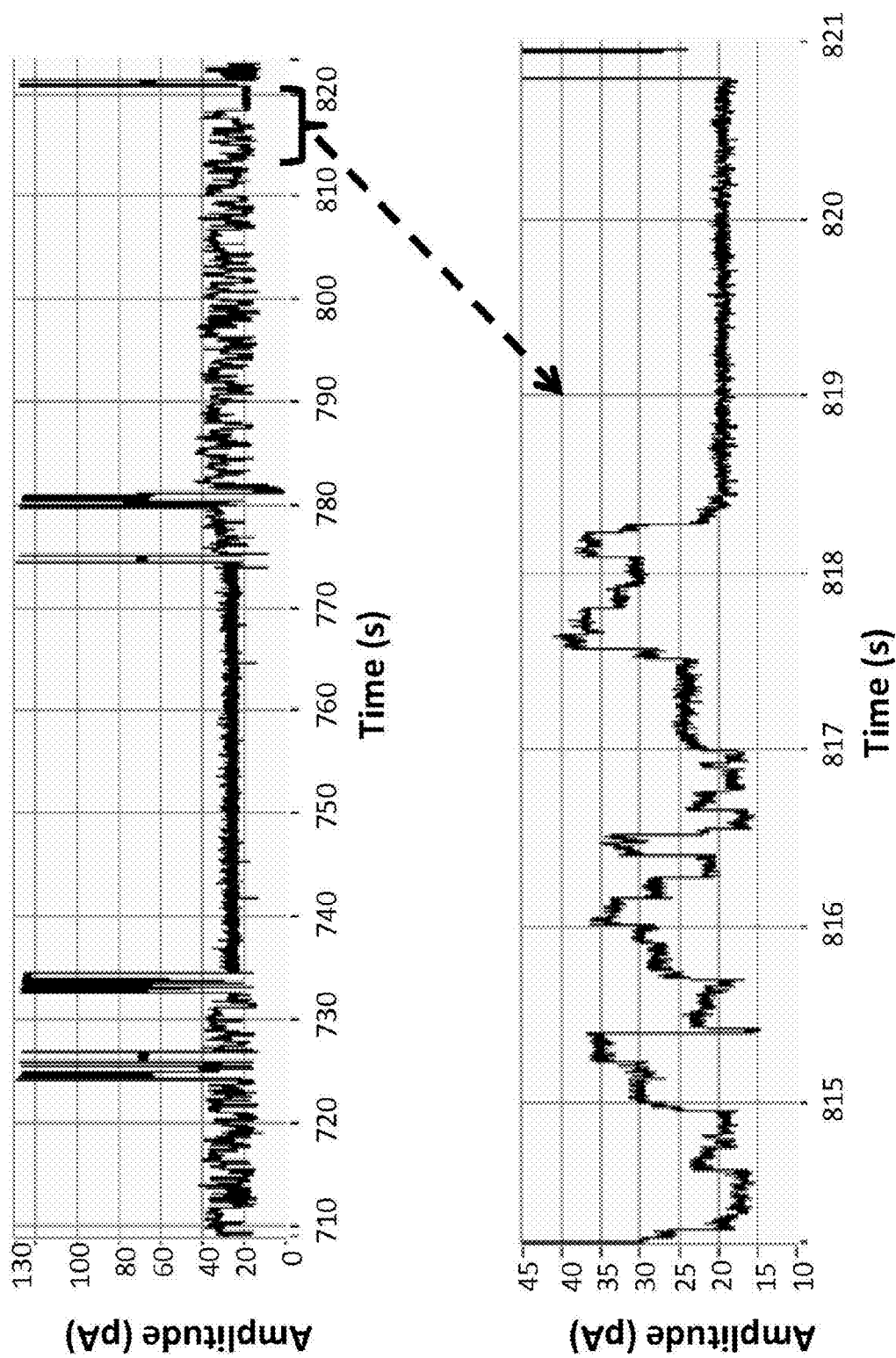
FIG. 18 shows an example event trace for the controlled translocation of DNA, mediated by a helicase, through the MS-(B1-B1)4 mutant pore which was produced by oligomerisation of the dimer. An expanded view, of the region highlighted in the upper trace, is shown below.

In the experiments, the baseline MS-(B1-B1)4 mutant pore formed from oligomerisation of the dimer inserted into lipid bilayers as effectively as the MS(B1)8 pore formed from oligomerisation of the monomer (see FIG. 16 showing pore insertion for the MS(B1)8 and MS-(B1-B1)4). When the monomer and dimer oligomerised pores were combined with a helicase as a molecular motor, it was possible to detect distinct current levels as the DNA strand was threaded through the pore. Typical DNA translocation events, in helicase translocating mode, are shown in FIG. 17 for the MS-(B1)8 pore formed from oligomerisation of the monomer and FIG. 18 for the MS-(B1-B1)4 pore formed from oligomerisation from the dimer. Therefore, the MS-(B1-B1)4 pore mutant oligomerised from the dimer unit was found to be as good a pore as the MS-(B1)8 pore mutant oligomerised from the monomer unit.

Figure 19:
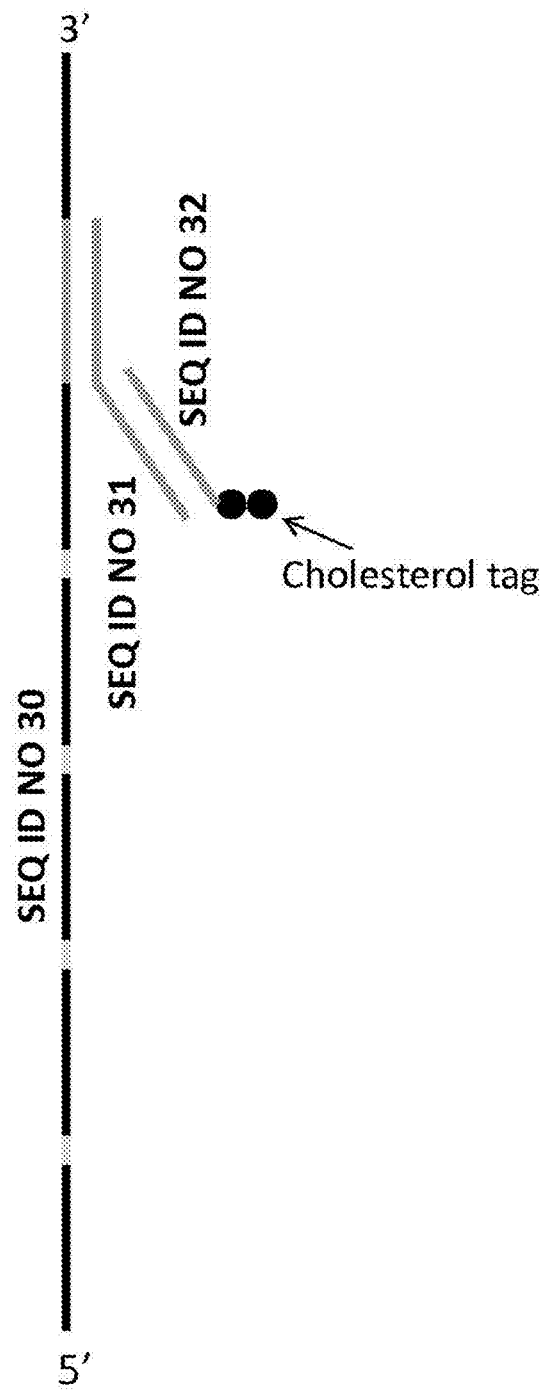
FIG. 19 shows the DNA substrate design used in Example 16.

Example 16—Use of the MS-(B1-L88N)8 Mutant MspA Pore to Distinguish 5-Methylcytosine from Cytosine This example describes how the MS-(B1-L88N)8 mutant pore of MspA can be used to distinguish cytosine from its epigenetically modified base 5-methylcytosine. The DNA substrate designs used in this experiment are shown in FIG. 19 and have the following sequences:
TTTTTTTTT/idSp/TTTTTTTTm-CTTTTTTTTCTTTTTTTTmCGTTTTTTTTCGTTT TTTTTGTATCTCCATCGCTGCCCCCTTTTTC-CCCCTTTTT (which is SEQ ID NO: 30 with 9 T nucleotidesand an IDT Int d Spacer (idSp) at the 5' end). mC represents 5-methylcytosine
GGCAGCGATGGAGATACTTGAGGCGAGCGGT-CAA (SEQ ID NO: 31) and
5CholTEG/TTGACCGCTCGCCTC (SEQ ID NO: 32 with a 5' Cholesteryl-TEG tag).

Materials

In order to form the DNA strand construct shown in FIG. 19 it was necessary to hybridise SEQ ID NO: 30, 31 and 32 together. This was carried out by pre-incubating all three strands at the same time.

Experimental Method

Buffered solution: 1 M KCl, 10 mM Hepes pH 8.0, 1 mM ATP, 1 mM $MgCl_2$, 1 mM DTT Nanopores: MS(B1-L88N)8 MspA Enzyme: Helicase The experimental set-up was carried out as described in Example 9. After achieving a single pore of MS-(B1-L88N) 8, in the bilayer, DNA polynucleotide (SEQ ID NOs: 30, 31 and 32) and helicase were added to 50 µL of buffer and pre-incubated for 5 mins (DNA=5 nM, Enzyme=100 nM). This pre-incubation mix was added to 950 µL of buffer in the cis compartment of the electrophysiology chamber to initiate capture of the helicase-DNA complexes in the MspA nanopore (to give final concentrations of DNA=5 nM, Enzyme=100 nM). Helicase ATPase activity was initiated as required by the addition of divalent metal (1 mM $MgCl_2$) and NTP (1 mM ATP) to the cis compartment. Experiments were carried out at a constant potential of +120 mV. Current levels were extracted as events from the DNA in the enzyme bound state. These events were indexed and the current level, duration and variance of the event recorded.

Figure 20:
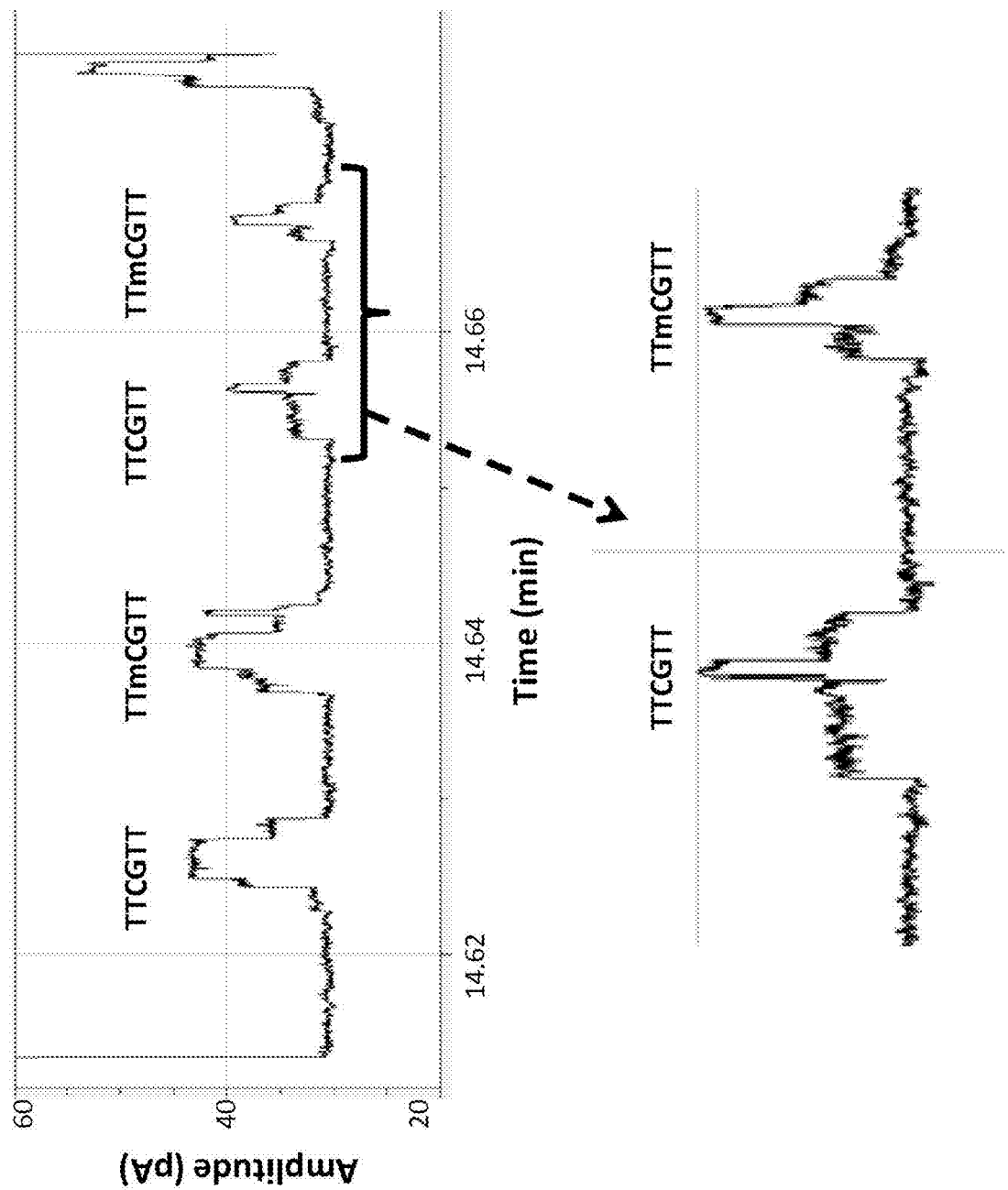
FIG. 20 shows an example event trace for the controlled translocation of DNA containing both cytosine and 5-methylcytosine, mediated by a helicase, through the MS-(B1-L88N)8 mutant pore. An expanded view of the region highlighted in the upper trace is shown below.

In the experiments it was observed that cytosine and 5-methylcytosine produced different current levels when translocated through the MS-(B1-L88N)8 pore under the control of a helicase (see FIG. 20). Therefore, using this mutated form of MspA it was possible to distinguish cytosine from its epigenetically modified base 5-methylcytosine.

The invention claimed is:

1. A mutant Msp monomer comprising a variant of the sequence shown in SEQ ID NO: 2, wherein the variant comprises a mutation at least one of the following positions of SEQ ID NO: 2: position 75, position 77, position 88 and position 126.

2. A mutant Msp monomer according to claim 1, wherein the variant comprises at least one of the following substitutions: G75S, G77S, L88N and Q126R.

3. A mutant Msp monomer according to claim 2, wherein the variant comprises the following substitutions: G75S, G77S and Q126R.

4. A mutant Msp monomer according to claim 3, wherein the variant further comprises a mutation at position 88.

5. A mutant according to claim 4, wherein the mutation at position 88 is L88N.

6. A mutant Msp monomer according to claim 1, wherein the variant further comprises at least one of the following mutations:
 (a) serine (S), glutamine (Q) or tyrosine (Y) at position 90;
 (b) leucine (L) or serine (S) at position 105;
 (c) arginine (R) at position 59;
 (d) leucine (L) at position 78;
 (e) asparagine (N) at position 81;
 (f) asparagine (N) at position 83;
 (g) serine (S) or threonine (T) at position 86;
 (h) phenylalanine (F), valine (V) or leucine (L) at position 87;
 (i) phenylalanine (F), valine (V) or leucine (L) at position 89;
 (j) leucine (L), phenylalanine (F), tryptophan (W), histidine (H), threonine (T), glycine (G), alanine (A), valine (V), arginine (R), lysine (K), asparagine (N) or cysteine (C) at position 90;
 (k) serine (S), glutamine (Q), leucine (L), methionine (M), isoleucine (I), alanine (A), valine (V), glycine (G), phenylalanine (F), tryptophan (W), tyrosine (Y), histidine (H), threonine (T), arginine (R), lysine (K), asparagine (N) or cysteine (C) at position 91;
 (l) alanine (A) or serine (S) at position 92;
 (m) serine (S), alanine (A), threonine (T), glycine (G) at position 93;
 (n) leucine (L) at position 94;
 (o) valine (V) at position 95;
 (p) arginine (R), aspartic acid (D), valine (V), asparagine (N), serine (S) or threonine (T) at position 96;
 (q) serine (S) at position 97;
 (r) serine (S) at position 98;
 (s) serine (S) at position 99;
 (t) serine (S) at position 100;
 (u) phenylalanine (F) at position 101;
 (v) lysine (K), serine (S) or threonine (T) at position 102;
 (w) alanine (A), glutamine (Q), asparagine (N), glycine (G) or threonine (T) at position 103;
 (x) isoleucine at position 104;
 (y) tyrosine (Y), alanine (A), glutamine (Q), asparagine (N), threonine (T), phenylalanine (F), tryptophan (W), histidine (H), glycine (G), valine (V), arginine (R), lysine (K), proline (P), or cysteine (C) at position 105;
 (z) phenylalanine (F), isoleucine (I), valine (V) or serine (S) at position 106;
 (aa) proline (P) or serine (S) at position 108;
 (bb) asparagine (N) at position 118;
 (cc) serine (S) or cysteine (C) at position 103; and
 (dd) cysteine at one or more of positions 10 to 15, 51 to 60, 136 to 139 and 168 to 172.

7. A mutant according to claim 1, wherein the variant further comprises one or more of the following substitutions at the other positions:
 (a) serine (S) at position 75, serine (S) at position 77, asparagine (N) at position 88, glutamine (Q) at position 90 and arginine (R) at position 126;
 (b) one or more of (i) glutamine (Q) at position 90 and (ii) alanine (A) at position 105;

(c) one or more of (i) serine (S) at position 90 and (ii) serine (S) at position 92;
(d) one or more of (i) glutamine (Q) at position 87 and (ii) serine (S) at position 90;
(e) one or more of (i) tyrosine (Y) at position 89 and (ii) serine (S) at position 90;
(f) one or more of (i) serine (S) at position 90 and (ii) alanine (A) at position 92;
(g) one or more of (i) serine (S) at position 90 and (ii) asparagine (N) at position 94;
(h) one or more of (i) serine (S) at position 90 and (ii) isoleucine (I) at position 104;
(i) one or more of (i) glutamine (Q) at position 90, (ii) serine (S) at position 93 and (iii) alanine (A) at position 105;
(j) one or more of (i) phenylalanine (F), tryptophan (W), tyrosine (Y) or histidine (H) at position 90, (ii) phenylalanine (F), tryptophan (W), tyrosine (Y) or histidine (H) at position 91 and (iii) phenylalanine (F), tryptophan (W), tyrosine (Y) or histidine (H) at position 105;
(k) one or more of (i) serine (S), threonine (T), glycine (G), alanine (A) or valine (V) at position 90, (ii) serine (S), threonine (T), glycine (G), alanine (A) or valine (V) at position 91 and (iii) serine (S), threonine (T), glycine (G), alanine (A) or valine (V) at position 105;
(l) serine (S), arginine (R), lysine (K) or histidine (H) at position 90 and/or serine (S), arginine (R), lysine (K) or histidine (H) at position 91;
(m) serine (S), threonine (T), asparagine (N), glutamine (Q), tyrosine (Y) or histidine (H) at position 90 and/or serine (S), threonine (T), asparagine (N), glutamine (Q), tyrosine (Y) or histidine (H) at position 91; and
(n) cysteine at one or more of positions 90, 91 and 103.

8. A mutant according to claim 1, wherein the variant further comprises at least one of the following substitution(s) at the other positions:

| | |
|---|---|
| (i) | D90S; |
| (ii) | D90Q; |
| (iii) | D90Y; |
| (iv) | I105L; |
| (v) | I105S; |
| (vi) | G75S, G77S, L88N, D90Q and Q126R; |
| (vii) | E59R; |
| (viii) | I78L; |
| (ix) | S81N; |
| (x) | T83N; |
| (xi) | N86S; |
| (xii) | N86T; |
| (xiii) | I87F; |
| (xiv) | I87V; |
| (xv) | I87L; |
| (xvi) | I89F; |
| (xvii) | I89V; |
| (xviii) | I89L; |
| (xix) | N90S; |
| (xx) | N90Q; |
| (xxi) | N90L; |
| (xxii) | N90Y; |
| (xxiii) | N91S; |
| (xxiv) | N91Q; |
| (xxv) | N91L; |
| (xxvi) | N91M; |
| (xxvii) | N91I; |
| (xxviii) | N91A; |
| (xxix) | N91V; |
| (xxx) | N91G; |
| (xxxi) | G92A; |
| (xxxii) | G92S; |
| (xxxiii) | N93S; |
| (xxxiv) | N93A; |
| (xxxv) | N93T; |
| (xxxvi) | I94L; |
| (xxxvii) | T95V; |
| (xxxviii) | A96R; |
| (xxxix) | A96D; |
| (xl) | A96V; |
| (xli) | A96N; |
| (xlii) | A96S; |
| (xliii) | A96T; |
| (xliv) | P97S; |
| (xlv) | P98S; |
| (xlvi) | F99S; |
| (xlvii) | G100S; |
| (xlviii) | L101F; |
| (xlix) | N102K; |
| (l) | N102S; |
| (li) | N102T; |
| (lii) | S103A; |
| (liii) | S103Q; |
| (liv) | S103N; |
| (lv) | S103G; |
| (lvi) | S103T; |
| (lvii) | V104I; |
| (lviii) | I105Y; |
| (lix) | I105L; |
| (lx) | I105A; |
| (lxi) | I105Q; |
| (lxii) | I105N; |
| (lxiii) | I105S; |
| (lxiv) | I105T; |
| (lxv) | T106F; |
| (lxvi) | T106I; |
| (lxvii) | T106V; |
| (lxviii) | T106S; |
| (lxix) | N108P; |
| (lxx) | N108S; |
| (lxxi) | D90Q and I105A; |
| (lxxii) | D90S and G92S; |
| (lxxiii) | I87Q and D90S; |
| (lxxiv) | I89Y and D90S; |
| (lxxv) | D90S and G92A; |
| (lxxvi) | D90S and I94N; |
| (lxxvii) | D90S and V104I; |
| (lxxviii) | D90Q, D93S and I105A; |
| (lxxix) | N91Y; |
| (lxxx) | N90Y and N91G; |
| (lxxxi) | N90G and N91Y; |
| (lxxxii) | N90G and N91G; |
| (lxxxiii) | I05G; |
| (lxxxiv) | N90R; |
| (lxxxv) | N91R; |
| (lxxxvi) | N90R and N91R; |
| (lxxxvii) | N90K; |
| (lxxxviii) | N91K; |
| (lxxxix) | N90K and N91K; |
| (xc) | N90Q and N91G; |
| (xci) | N90G and N91Q; |
| (xcii) | N90Q and N91Q; |

-continued

| | |
|---|---|
| (xciii) | R118N; |
| (xciv) | N91C; |
| (xcv) | N90C; |
| (xcvi) | N90W; |
| (xcvii) | N91W; |
| (xcviii) | N90K; |
| (xcix) | N91K; |
| (c) | N90R; |
| (ci) | N91R; |
| (cii) | N90S and N91S; |
| (ciii) | N90Y and I105A; |
| (civ) | N90G and I105A; |
| (cv) | N90Q and I105A; |
| (cvi) | N90S and I105A; |
| (cvii) | N90G and N93G; |
| (cviii) | N90G; |
| (cix) | N93G; |
| (cx) | N90G and N91A; |
| (cxi) | I105K; |
| (cxii) | I105R; |
| (cxiii) | I105V; |
| (cxiv) | I105P; |
| (cxv) | I105W; |
| (cxvi) | N90R and I105A; |
| (cxvii) | N90S and I105A; |
| (cxviii) | S103C; and |
| (cxix) | I105C. |

9. A mutant according to claim 1, wherein the mutant is chemically modified.

10. A mutant according to claim 9, wherein (i) the mutant is chemically modified by attachment of a molecule to one or more cysteines, attachment of a molecule to one or more lysines, attachment of a molecule to one or more non-natural amino acids, enzyme modification of an epitope or modification of a terminus; (ii) the mutant is chemically modified by attachment of a molecule to one or more cysteines and the one or more cysteines have been introduced to the mutant by substitution; (iii) the mutant is chemically modified by attachment of a molecule to one or more cysteines, attachment of a molecule to one or more lysines or attachment of a molecule to one or more non-natural amino acids and the molecule is (a) a molecular adaptor that facilitates the interaction between a pore comprising the monomer and a target nucleotide or target nucleic acid sequence or (b) a nucleic acid binding protein; (iv) the mutant is chemically modified by attachment of a molecule to one or more cysteines, attachment of a molecule to one or more lysines or attachment of a molecule to one or more non-natural amino acids and the attachment is via a linker or (v) the mutant is chemically modified by attachment of a molecule to one or more cysteines, attachment of a molecule to one or more lysines or attachment of a molecule to one or more non-natural amino acids and the molecule is attached to one or more of positions 90, 91 and 103 of SEQ ID NO: 2.

11. A construct comprising two or more covalently attached Msp monomers.

12. A construct comprising two or more covalently attached Msp monomers, wherein (a) the two or more monomers are the same or different; (b) at least one monomer comprises the sequence shown in SEQ ID NO: 2; (c) at least one of the monomers is a mutant monomer as defined in claim 1; (d) the construct comprises two monomers and at least one of the monomers is a mutant as defined in claim 1; (e) the monomers are genetically fused; or (f) the monomers are attached via a linker.

13. A polynucleotide which encodes a mutant according to claim 1 or a construct according to claim 11.

14. A homo-oligomeric Msp pore comprising identical mutant monomers according to claim 1.

15. A homo-oligomeric Msp pore comprising eight identical mutant monomers according to claim 1.

16. A hetero-oligomeric Msp pore comprising at least one mutant monomer according to claim 1, wherein at least one of the eight monomers differs from the others.

17. A hetero-oligomeric Msp pore, wherein
   (i) the pore comprises eight mutant monomers according to claim 1 and at least one of them differs from the others;
   (ii) the pore comprises at least one monomer comprising the sequence shown in SEQ ID NO: 2;
   (iii) the pore comprises (a) one mutant monomer and (b) seven identical monomers, wherein the mutant monomer in (a) is different from the identical monomers in (b); or
   (iv) the pore comprises (a) seven monomers comprising the sequence shown in SEQ ID NO: 2 and one mutant monomer according to claim 1 comprising the substitution N90R, N90K, N90Y, N9OQ, N90W or N90C, (b) seven monomers comprising the sequence shown in SEQ ID NO: 2 and one mutant monomer according to claim 1 comprising the substitution N91R, N91K, N91Y, N91Q, N91W or N91C or (c) seven monomers comprising the sequence shown in SEQ ID NO: 2 and one mutant monomer according to claim 1 comprising the substitution L88C, S103C or I105C.

18. A pore according to claim 15, wherein at least one of the mutant monomers is chemically-modified.

19. A pore according to claim 17, wherein at least one of the mutant monomers is chemically-modified.

20. A pore comprising at least one construct according to claim 11.

21. A pore comprising two or more covalently attached Msp monomers, further comprising:
   four constructs each comprising two monomers and at least one of the monomers is a mutant as defined in claim 1; or
   one construct comprising a mutant monomer as defined in claim 1 and six monomers each comprising (i) the sequence shown in SEQ ID NO: 2 or (ii) a variant of SEQ ID NO: 2 as defined in claim 1.

22. A pore according to claim 20, wherein at least one of the constructs is chemically-modified.

23. A method of characterising a target nucleic acid sequence, comprising:
   (a) contacting the target nucleic acid sequence with a pore according to claim 14, 16 or 20 and a nucleic acid binding protein so that the nucleic acid binding protein controls the movement of the target nucleic acid sequence through the pore, wherein the nucleic acid binding protein is selected from the group consisting of nucleases, polymerases, topoisomerases, ligases, helicases, and single strand binding proteins (SSB); and
   (b) measuring, upon application of a potential across the pore, a current passing through the pore as the target nucleic acid sequence moves through the pore, wherein the current flow through the pore is distinctive for nucleotides of the target nucleic acid and thereby characterising the target nucleic acid sequence based on the current measurements.

24. A kit for characterising a target nucleic acid sequence comprising (a) a pore according to claim 14, 16 or 20 and (b) a nucleic acid handling enzyme, wherein the nucleic acid handling enzyme is selected from the group consisting of nucleases, polymerases, topoisomerases, ligases, helicases, and single strand binding proteins (SSB).

25. An apparatus for characterising target nucleic acid sequences in a sample, comprising (a) a plurality of pores according to claim 14, 16 or 20 and (b) a plurality of nucleic acid handling enzymes, wherein the nucleic acid handling enzyme is selected from the group consisting of nucleases, polymerases, topoisomerases, ligases, helicases, and single strand binding proteins (SSB).

26. An apparatus according to claim 25, wherein the apparatus comprises:
   a sensor device that is capable of supporting the plurality of pores and being operable to perform nucleic acid characterisation using the pores and enzymes;
   at least one reservoir for holding material for performing the characterisation;
   a fluidics system configured to controllably supply material from the at least one reservoir to the sensor device; and
   a plurality of containers for receiving respective samples, the fluidics system being configured to supply the samples selectively from the containers to the sensor device.

* * * * *

UNITED STATES PATENT AND TRADEMARK OFFICE
CERTIFICATE OF CORRECTION

PATENT NO. : 9,751,915 B2
APPLICATION NO. : 13/984628
DATED : September 5, 2017
INVENTOR(S) : James Clarke et al.

It is certified that error appears in the above-identified patent and that said Letters Patent is hereby corrected as shown below:

In the Claims

Claim 1, at Column 87, Line 33:
"comprises a mutation at least one of the following positions"
Should read:
--comprises a mutation at at least one of the following positions--

Claim 8, at Column 89, Line 40:
"(i) D90S;"
Should read:
--(i) N90S;--

Claim 8, at Column 89, Line 41:
"(ii) D90Q;"
Should read:
--(ii) N90Q;--

Claim 8, at Column 89, Line 42:
"(iii) D90Y;"
Should read:
--(iii) N90Y;--

Claim 8, at Column 89, Lines 44-45:
"(vi) G75S, G77S, L88N, D90Q"
Should read:
--(vi) G75S, G77S, L88N, N90Q--

Signed and Sealed this
Eighth Day of May, 2018

Andrei Iancu
*Director of the United States Patent and Trademark Office*

Claim 8, at Column 90, Line 34:
"(lxxi) D90Q and"
Should read:
--(lxxi) N90Q and--

Claim 8, at Column 90, Line 36:
"(lxxii) D90S and"
Should read:
--(lxxii) N90S and--

Claim 8, at Column 90, Lines 37-38:
"(lxxiii) I87Q and D90S;"
Should read:
--(lxxiii) I87Q and N90S;--

Claim 8, at Column 90, Lines 39-40:
"(lxxiv) I89Y and D90S;"
Should read:
--(lxxiv) I89Y and N90S;--

Claim 8, at Column 90, Line 41:
"(lxxv) D90S and"
Should read:
--(lxxv) N90S and--

Claim 8, at Column 90, Line 42:
"(lxxvi) D90S and"
Should read:
--(lxxvi) N90S and--

Claim 8, at Column 90, Line 44:
"(lxxvii) D90S and"
Should read:
--(lxxvii) N90S and--

Claim 8, at Column 90, Lines 46-47:
"(lxxviii) D90Q, D93S and"
Should read:
--(lxxviii) N90Q, N93S and--